(12) United States Patent
Sharei et al.

(10) Patent No.: US 10,696,944 B2
(45) Date of Patent: *Jun. 30, 2020

(54) INTRACELLULAR DELIVERY

(71) Applicants: Massachusetts Institute of Technology, Cambridge, MA (US); Armon R. Sharei, Watertown, MA (US); Andrea Adamo, Cambridge, MA (US); Robert S. Langer, Newton, MA (US); Klavs F. Jensen, Lexington, MA (US)

(72) Inventors: Armon R. Sharei, Watertown, MA (US); Andrea Adamo, Cambridge, MA (US); Robert S. Langer, Newton, MA (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 385 days.

This patent is subject to a terminal disclaimer.

(21) Appl. No.: 14/352,354

(22) PCT Filed: Oct. 17, 2012

(86) PCT No.: PCT/US2012/060646
§ 371 (c)(1),
(2) Date: Apr. 17, 2014

(87) PCT Pub. No.: WO2013/059343
PCT Pub. Date: Apr. 25, 2013

(65) Prior Publication Data
US 2014/0287509 A1    Sep. 25, 2014

Related U.S. Application Data

(60) Provisional application No. 61/684,301, filed on Aug. 17, 2012, provisional application No. 61/548,013, filed on Oct. 17, 2011.

(51) Int. Cl.
*C12N 5/071* (2010.01)
*C12M 1/42* (2006.01)
(Continued)

(52) U.S. Cl.
CPC .......... *C12N 5/0602* (2013.01); *C12M 23/16* (2013.01); *C12M 35/02* (2013.01); *C12M 35/04* (2013.01); *C12N 15/87* (2013.01); *B82Y 5/00* (2013.01)

(58) Field of Classification Search
None
See application file for complete search history.

(56) References Cited

U.S. PATENT DOCUMENTS 4,055,799 A    10/1977   Coster
4,835,457 A     5/1989   Hanss
(Continued)

FOREIGN PATENT DOCUMENTS

CN    106244543 A   12/2016
EP      0882448 B1   12/1998
(Continued)

OTHER PUBLICATIONS

ATCC (2012, Thawing, Propagating, and Cryopreserving Protocol, NCI-PBCF-HTB81 (DU 145) Prostate Carcinoma (ATCC® HTB-81), Version 1.6.*

(Continued)

*Primary Examiner* — Sharmila G Landau
*Assistant Examiner* — Stephanie A McNeil
(74) *Attorney, Agent, or Firm* — Wolf, Greenfield & Sacks, P.C.

(57) ABSTRACT

A microfluidic system for causing perturbations in a cell membrane, the system including a microfluidic channel defining a lumen and being configured such that a cell suspended in a buffer can pass therethrough, wherein the (Continued)

microfluidic channel includes a cell-deforming constriction, wherein a diameter of the constriction is a function of the diameter of the cell.

67 Claims, 41 Drawing Sheets

(51) Int. Cl.
*C12M 3/06* (2006.01)
*C12N 15/87* (2006.01)
*B82Y 5/00* (2011.01)

(56) References Cited

U.S. PATENT DOCUMENTS

| | | | |
|---|---|---|---|
| 5,023,054 | A | 6/1991 | Sato |
| 5,643,577 | A | 7/1997 | Pang et al. |
| 5,658,892 | A | 8/1997 | Flotte |
| 5,842,787 | A | 12/1998 | Kopf-Sill |
| 5,951,976 | A | 9/1999 | Segal |
| 6,156,181 | A | 12/2000 | Parce |
| 6,186,660 | B1 | 2/2001 | Kopf-Sill |
| 6,218,166 | B1 | 4/2001 | Ravindranath et al. |
| 6,410,329 | B1 | 6/2002 | Hansen et al. |
| 6,461,867 | B1 | 10/2002 | Cai et al. |
| 6,562,616 | B1 | 5/2003 | Toner |
| 7,109,034 | B2 † | 9/2006 | Orwar |
| 7,704,743 | B2 | 4/2010 | Fedorov et al. |
| 7,993,821 | B2 | 8/2011 | Chiu |
| 8,211,656 | B2 | 7/2012 | Hyde et al. |
| 8,669,044 | B2 | 3/2014 | Chiu |
| 8,697,359 | B1 | 4/2014 | Zhang |
| 8,844,570 | B2 | 9/2014 | Glick et al. |
| 9,005,579 | B2 | 4/2015 | Nowinski et al. |
| 9,017,991 | B2 | 4/2015 | Diefenbach |
| 9,157,550 | B2 | 10/2015 | Wheeler |
| 9,255,245 | B2 | 2/2016 | Bernick et al. |
| 9,364,504 | B2 | 6/2016 | Godfrin et al. |
| 9,950,049 | B2 | 4/2018 | Godfrin et al. |
| 10,124,336 | B2 | 11/2018 | Sharei et al. |
| 10,526,573 | B2 | 1/2020 | Ding et al. |
| 2003/0133922 | A1 | 7/2003 | Kasha, Jr. |
| 2004/0176282 | A1 | 9/2004 | Dalby et al. |
| 2004/0197898 | A1 | 10/2004 | Nakatani |
| 2005/0026283 | A1 † | 2/2005 | Ormar |
| 2006/0134067 | A1 * | 6/2006 | Liu ............... A61K 39/0011 |
| | | | 424/93.2 |
| 2006/0134772 | A1 * | 6/2006 | Miles ............. B01L 3/502761 |
| | | | 435/283.1 |
| 2006/0223185 | A1 | 10/2006 | Fedorov |
| 2007/0243523 | A1 | 10/2007 | Ionescu-Zanetti et al. |
| 2007/0249038 | A1 | 10/2007 | Adamo et al. |
| 2008/0311140 | A1 | 12/2008 | Lee et al. |
| 2008/0318324 | A1 | 12/2008 | Chiu et al. |
| 2009/0209039 | A1 | 9/2009 | Adamo |
| 2009/0280518 | A1 | 11/2009 | Adamo et al. |
| 2010/0203068 | A1 | 8/2010 | Betz et al. |
| 2010/0249621 | A1 | 9/2010 | Ichitani |
| 2010/0323388 | A1 | 12/2010 | Chiu et al. |
| 2011/0030808 | A1 | 2/2011 | Chiou et al. |
| 2011/0091973 | A1 | 4/2011 | Glaser et al. |
| 2011/0300205 | A1 | 12/2011 | Geall et al. |
| 2012/0064505 | A1 | 3/2012 | Suresh et al. |
| 2012/0107925 | A1 | 5/2012 | Li et al. |
| 2012/0207745 | A1 | 8/2012 | Godfrin et al. |
| 2013/0023051 | A1 | 1/2013 | Bundock et al. |
| 2013/0045211 | A1 | 2/2013 | Nowinski |
| 2013/0065314 | A1 | 3/2013 | MacMillan |
| 2014/0011226 | A1 | 1/2014 | Bernick |
| 2014/0273229 | A1 | 9/2014 | Meacham et al. |
| 2014/0287509 | A1 | 9/2014 | Sharei et al. |
| 2015/0184127 | A1 | 7/2015 | White et al. |
| 2015/0196913 | A1 | 7/2015 | Liu |
| 2016/0017340 | A1 | 1/2016 | Wu |
| 2016/0193605 | A1 | 7/2016 | Sharei et al. |
| 2016/0199837 | A1 | 7/2016 | Breinlinger |
| 2017/0020926 | A1 | 1/2017 | Mata-Fink et al. |
| 2017/0326213 | A1 | 11/2017 | Jajosky et al. |
| 2018/0003696 | A1 | 1/2018 | Sharei et al. |
| 2018/0016539 | A1 | 1/2018 | Ding et al. |
| 2018/0085402 | A1 | 3/2018 | Kahvejian et al. |
| 2018/0142198 | A1 | 5/2018 | Sharei et al. |
| 2018/0201889 | A1 | 7/2018 | Sharei et al. |
| 2018/0245089 | A1 | 8/2018 | Sharei et al. |
| 2019/0030536 | A1 | 1/2019 | Sharei et al. |
| 2019/0093073 | A1 | 3/2019 | Sharei et al. |

FOREIGN PATENT DOCUMENTS

| | | |
|---|---|---|
| EP | 1 225 228 A2 | 7/2002 |
| EP | 2169070 | 3/2010 |
| JP | H01196566 | 8/1989 |
| JP | H03257366 | 11/1991 |
| JP | 2010-02582 A | 2/2010 |
| JP | 2010025852 A | 2/2010 |
| JP | 2011-163830 A | 8/2011 |
| JP | 6235085 B2 | 11/2017 |
| KR | 2014-0115560 A | 10/2014 |
| WO | WO 1985/000748 A1 | 2/1985 |
| WO | WO 1997/020570 A1 | 6/1997 |
| WO | WO 00/07630 A1 | 2/2000 |
| WO | WO 02/067863 A2 | 9/2002 |
| WO | WO 03/020039 A1 | 3/2003 |
| WO | WO 2004/001424 A1 | 12/2003 |
| WO | WO 2006/010521 A1 | 2/2006 |
| WO | WO 2006/095330 A2 | 9/2006 |
| WO | 2006105251 A2 † | 10/2006 |
| WO | WO 2006/105251 A2 | 10/2006 |
| WO | WO 2007/067032 A1 | 6/2007 |
| WO | WO 2007/097934 A2 | 8/2007 |
| WO | 2008021465 A2 | 2/2008 |
| WO | WO 2009/056332 A1 | 5/2009 |
| WO | WO 2010/010513 A2 | 1/2010 |
| WO | WO-10016800 A1 | 2/2010 |
| WO | WO 2010/077290 A1 | 7/2010 |
| WO | WO 2010/105135 A1 | 9/2010 |
| WO | WO 2010/129671 A2 | 11/2010 |
| WO | WO 2010/145849 A2 | 12/2010 |
| WO | WO 2011/051346 A1 | 5/2011 |
| WO | WO-2011/119492 A2 | 9/2011 |
| WO | WO 2012/097450 A1 | 7/2012 |
| WO | WO 2012/106536 A2 | 8/2012 |
| WO | WO 2012/118799 | 9/2012 |
| WO | WO 2012/162779 A1 | 12/2012 |
| WO | WO 2013/059343 A1 | 4/2013 |
| WO | WO 2013/185032 A1 | 12/2013 |
| WO | WO 2014/106629 A1 | 7/2014 |
| WO | WO 2014/106631 A1 | 7/2014 |
| WO | WO 2014/120956 A1 | 8/2014 |
| WO | WO 2014/165707 A2 | 10/2014 |
| WO | WO 2015/023982 A1 | 2/2015 |
| WO | WO 2015/061458 | 4/2015 |
| WO | WO 2015/061458 A1 | 4/2015 |
| WO | WO 2015/153102 A1 | 10/2015 |
| WO | WO 2015/161276 A2 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 | 7/2016 |
| WO | WO 2016/115179 | 7/2016 |
| WO | WO 2016/183482 A1 | 11/2016 |
| WO | WO 2017/005700 A1 | 1/2017 |
| WO | WO 2017/008063 A1 | 1/2017 |
| WO | WO-2017/041050 A1 | 3/2017 |
| WO | WO-2017/041051 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |
| WO | WO 2017/123663 A1 | 7/2017 |
| WO | WO 2017/192785 A1 | 11/2017 |

(56) References Cited

FOREIGN PATENT DOCUMENTS

| WO | WO 2017/192786 A1 | 11/2017 |
|---|---|---|
| WO | WO 2018/089497 A1 | 5/2018 |

OTHER PUBLICATIONS

Hosokawa et al, Size-Selective Microcavity Array for Rapid and Efficient Detection of Circulating Tumor Cells, 2010, Anal. Chem., 82, 6629-6635 (Year: 2010).*

Shelby et al. "A Microfluidic Model for Single-Cell Capillary Obstruction by *Plasmodium falciparum*—Infected Erythrocytes." *PNAS.* 100.25(2003):14618-14622.

Adamo, Andrea et al., "Microfluidics-Based Assessment of Cell Deformability," Analytical Chemistry, vol. 84:6438-6443 (2012).

Hallow, Daniel M. et al., "Shear-Induced Intracellular Loading of Cells With Molecules by ControlledMicrofluidics," Biotechnology and Bioengineering, vol. 99(4):846-854 (2008).

Liu, Yan et al., "Spatially selective reagent delivery into cancer cells using a two-layer microfluidic culture system," Analytica Chimica Acta, vol. 743:125-130 (2012).

Sharei, Armon et al., "A vector-free microfluidic platform for intracellular delivery," PNAS, vol. 110(6):2082-2087 (2013).

Sharei, Armon et al., "Cell Squeezing as a Robust, Microfluidic Intracellular Delivery Platform," J. Vis. Exp., vol. 81: e50980, doi:10.3791/50980, 9 pages (2014).

Sharei, A. et al., "Microfluidic Cell Deformation as a Robust, Vector-Free Method for Cytosolic Delivery of Macromolecules," AIChE, Conference Proceedings, 2012 Annual Meeting, retrieved online at: http:www.3.aiche.org/proceedings/Abstract.aspx?PaperID=266712, Abstract No. 483d, 7 pages (2012).

Office Action dated Jun. 14, 2016 from European Application No. 12841329.1, 4 pp.

American Type Culture Collection, "Thawing, Propagating, and Cryopreserving Protocol," Version 1.6, Physical Sciences—Oncology Center Network Bioresource Core Facility, 23 pp, Feb. 27, 2012.

Office Action dated Jul. 7, 2016 from Japanese Application No. 2014-537184, 7 pp.

BD Bioscience FITC-labeled anti-CD45 antibody, 2 pages.

BD Bioscience PE-labeled anti-EpCAM antibody, 2 pages.

Boohaker, et al., "The Use of Therapeutic Peptides to Target and to Kill Cancer Cells," Curr. Med. Chem., 19(22), 26 pages, 2012.

Cancer Facts & Figures 2012. Published by the American Cancer Society in Atlanta, 68 pages.

Downs, C. A. et al. (May 14, 2011). "Cell Culture Models Using Rat Primary Alveolar type 1 Cells", Pulmonary Pharm. & Therapeutics 24(5)577-586.

Extended European Search Report for EP 14836593.5, dated Feb. 23, 2017, 9 pages.

Gasteiger, et al., "Protein Identification and Analysis Tools on the ExPASy Server," The Proteomics Handbook, Chapter 52, pp. 571-607, 2005.

Hoskin, et al., "Studies on anticancer activitied of antimicrobial peptides," Biochimica et Biophysica Acta, v.1778, pp. 357-375, 2008.

Hosokawa, et al., "Size-Selective Microacvity Array for Rapid and Efficient Detection of Circulation Tumor Cells," Anal. Chem, 85:6629-6635, 2010.

Howarth, M. et al. (May 2008). "Monovalent, Reduced-Size Quantum Dots for Imaging Receptors on Living Cells," Nature Methods 5(5):397-399.

International Preliminary Report on Pattentability, PCT/US2012/060646, dated Apr. 22, 2014, 7 pages.

International Preliminary Report on Pattentability, PCT/US2015/058489, dated May 2, 2017, 12 pages.

International Preliminary Report on Pattentability, PCT/US2015/060689, dated May 16, 2017, 10 pages.

Janeway CA Jr, et al., "The structure of a typical antibody molecule," Immunobiology: The Immune System in Heath and Disease, 5th edition (2001), 5 pages.

Kim, D., et al., "Microengineered Platforms for Cell Mechanobiology," Annual Review of Biomedical Engineering, 2009, vol. 11, pp. 203-233.

Liu, W. et al. (Jan. 20, 2010). "Compact Biocompatible Quantum Dots Via RAFT-Mediated Synthesis of Imidazole-Based Random Copolymer Ligand," JACS 132(2):472-483.

Matthews, B.D., et al., "Cellular adaptation to mechanical stress: role of integrins, Rho, cytoskeletal tension and mechanosensitive ion channels," Journal of Cell Science, vol. 119, pp. 508-518, 2006.

Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.

Swaminathan, et al., "Mechanical Stiffness Grades Metastatic Potential in Patient Tumor Cells and in Cancer Cell Lines," Cancer Research, 71(15):5075-5080, 2011.

Williams, A.R. et al. (Nov. 5, 1999). "Filtroporation: A Simple, Reliable Technique for Transfection and Macromolecular Loading of Cells", Biotechnology and Bioengineering 65(3)341-346.

Banz, A. et al., "Tumor Growth Control Using Red Blood Cells as the Antigen Delivery System and Poly(I:C)," J Immunother 2012, 35(5), pp. 409-417.

Certificate of Grant dated Jan. 11, 2018 for Chinese Application No. 201280060689.6.

Chaw, K. C. et al., "Multi-step microfluidic device for studying cancer metastasis," Lab Chip (2007), vol. 7, pp. 1041-1047.

Cremel, L. et al., "Innovative approach in Pompe disease therapy: Induction of immune tolerance by antigen-encapsulated red blood cells," Int J Pharm. Aug. 1, 2015;491(1-2), pp. 69-77.

Cremel, L. et al., "Red blood cells as innovative antigen carrier to induce specific immune tolerance," Int J Pharm. Feb. 25, 2013;443(1-2), pp. 39-49.

Eixarch, H. et al. "Tolerance induction in experimental autoimmune encephalomyelitis using non-myeloablative hematopoietic gene therapy with autoantigen." Molecular Therapy 17.5 (2009): 897-905.

Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).

Examination Report No. 1 dated Dec. 1, 2016 from Australian Application No. 2012326203, 10 pages.

Examination Report No. 2 dated Jul. 26, 2017 from Australian Application No. 2012326203, 6 pages.

Extended European Search Report for EP 16737769.6, dated May 3, 2018, 11 pages.

Grimm, A. J. et al., "Memory of tolerance and induction of regulatory T cells by erythrocyte-targeted antigens," Sci Rep. Oct. 29, 2015;5:15907, 11 pages.

Hao, Y. et al., "Delivery technologies for genome editing," Nature Reviews (2017), vol. 16, No. 6, pp. 387-399.

Hoeppener et al., "Immunomagnetic Separation Technologies," In: Ignatiadis M., Soritiou C., Pantel K. (eds.), Minimal Residual Disease and Circulating Tumor Cells in Breast Cancer. Recent Results in Cancer Research, vol. 195, pp. 43-58 (2012).

International Search Report and Written Opinion dated Jan. 12, 2016 from International Application No. PCT/US2016/050288, 14 pages.

International Search Report and Written Opinion dated Jan. 3, 2017 from International Application No. PCT/US2016/050287, 13 pages.

International Search Report and Written Opinion dated Jul. 21, 2017 from International Application No. PCT/US2017/030933, 20 pages.

International Search Report and Written Opinion dated Sep. 19, 2017 from International Application No. PCT/US2017/030932, 18 pages.

Lorenz, K. M. et al., "Engineered binding to erythrocytes induces immunological tolerance to *E. coli* asparaginase," Sci Adv. Jul. 17, 2015;1(6):e1500112, 11 pages.

Mali, P. et al., "RNA-guided human Genome Engineering via Cas9," Science (2013), vol. 339, No. 6121, pp. 823-826.

(56) References Cited

OTHER PUBLICATIONS

Milo, R. "What is the total number of protein molecules per cell volume? A call to rethink some published values." Bioessays 35.12 (2013): 1050-1055.
Notice of Grant dated Jan. 11, 2018 for Chinese Patent Application No. 201280060689.6.
Notice of Reasons for Rejection dated Jun. 4, 2018 from Japanese Application No. 2016-534877, with English language translation, 6 pages.
Office Action dated Dec. 1, 2016 from Chinese Application No. 201280060689.6, 4 pages.
Office Action dated Dec. 17, 2014 from Chinese Office Action No. 201280060689.6, 9 pages.
Office Action dated Jun. 23, 2017 from Chinese Application No. 201280060689.6, 4 pages.
Office Action dated Oct. 11, 2017 from European Application No. 12 841 329, 4 pages.
Office Action dated Sep. 6, 2015 from Chinese Office Action No. 201280060689.6, 8 pages.
Office Action dated Aug. 15, 2017 from U.S. Appl. No. 14/912,001, 32 pages.
Office Action dated Jul. 5, 2017 from Chinese Application No. 201480056295.2, 13 pages.
Office Action dated Jul. 7, 2016 from Japanese Application No. 2014-537184, w/English language translation, 14 pages.
Office Action dated Mar. 16, 2017 from U.S. Appl. No. 14/912,001, 29 pages.
Office Action dated Mar. 23, 2017 from Russian Application No. 2014119926/10(031699), w/English language translation, 10 pages.
Office Action dated May 1, 2017 from Japanese Application No. 2014-537184, with English language translation, 13 pages.
Office Action dated Oct. 26, 2016 from Russian Application No. 2014119926/10(031699), w/English language translation, 10 pages.
Official Action dated Jun. 22, 2018 from European Application No. 12841329.1, 3 pages.
Partial Supplementary European Search Report dated May 30, 2018 for European Application No. 15855640.7, 19 pages.
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Ravilla et al., "Erythrocytes as Carrier for Drugs, Enzymes and Peptides," Journal of Applied Pharmaceutical Science, vol. 2, No. 2, pp. 166-176 (2012).
Restriction Requirement dated May 15, 2018 from U.S. Appl. No. 15/523,142, 12 pages.
Rughetti, A. et al., "Transfected human dendritic cells to induce antitumor immunity," Gene Therapy, vol. 7, pp. 1458-1466 (2000).
Rutella et al., "Tolerogenic dendritic cells: cytokine modulation comes of age," Blood, vol. 108, No. 5, pp. 1435-1440 (2006).
Steinman et al., "Tolerogenic dendritic cells," Annual Review of Immunology, vol. 21, pp. 685-711 (2003).
Stewart et al., "In vitro and ex vivo strategies for intracellular delivery," Nature, vol. 538, No. 7624, pp. 183-192 (2016).
Szeto et al., "Microfluidic squeezing for intracellular antigen loading in polyclonal B-cells as cellular vaccines," Scientific Reports, vol. 5, 10276 (May 2015), 13 pages.
Third-Party Submission dated Oct. 16, 2015 from U.S. Appl. No. 14/352,354, 21 pages.
International Search Report and Written Opinion for PCT/US16/41653 dated Oct. 4, 2016.
International Preliminary Report on Patentability for PCT/US16/41653 dated Jan. 18, 2018 (Chapter I).
International Preliminary Report on Patentability for PCT/US2016/013113 dated Jul. 27, 2017 (Chapter I).
Partial Supplementary European Search Report for EP App. No. 15859824.3 dated Jun. 11, 2018.

Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.
Ding, X. et al., "High-throughput nuclear delivery and rapid expression of DNA via mechanical and electrical cell-membrane disruption," Nature Biomedical Engineering (2017), vol. 1, No. 3, 7 pages.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Kiani et al., Cas9 gRNA engineering for genome editing, activation and repression. Nature Methods. 2015;12:1051-4.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Maratou et al., Glucose transporter expression on the plasma membrane of resting and activated while blood cells. European Journal of Clinical Investigation. 2007;37:282-90.
Rossi, L. et al., "Erythrocyte-mediated delivery of phenylalanine ammonia lyase for the treatment of phenylketonuria in BTBR-Pah. sup.enu2 mice," Journal of Controlled Release 194; 37-44 (2014).
Stevenson, D. J. et al., "Single cell optical transfection," IEEE Transactions on Ultrasonics, Ferroelectrics and Frequency Control, vol. 53, No. 1, 863-871 (2010).
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Wright et al., Rational design of a split-Cas9 enzyme complex. PNAS. Mar. 2015;112(10):2984-9.
Zdobnova et al., Self-Assembling Complexes of Quantum Dots and scFv Antibodies for Cancer Cell Targeting and Imaging. PLoS One. 2012;7(10):e48248. 8 pages.
Extended European Search Report for EP App. No. 16822078.8 dated Jan. 30, 2019.
Extended European Search Report for EP App. No. 15859824.3 dated Sep. 11, 2018.
Extended European Search Report for EP App. No. 15855640.7 dated Sep. 5, 2018.
Ditommaso et al., Cell engineering with microfluidic squeezing preserves functionality of primary immune cells in vivo. PNAS. Oct. 2018;115(46):E10907-14.
Gossett et al., Hydrodynamic stretching of single cells for large population mechanical phenotyping. PNAS. May 2012;109(20):7630-5.
Nic An Tsaoir et al., Scalable Antibody Production from CHO Cell Line of Choice Using Flow Electroporation. MaxCyte. Jun. 2016. 1 page.
Stevenson, D. J. et al., "Single cell optical transfection," J. R. Soc. Interface, vol. 7, 863-871 (2010).
Weaver et al., A brief overview of electroporation pulse strength-duration space: A region where additional intracellular effects are expected. Bioelectrochemistry. Oct. 2012;87:236-43.
EP 19187758.8, Nov. 21, 2019, Extended European Search Report.
Extended European Search Report dated Nov. 21, 2019 for Application No. EP 19187758.8.
Sharei et al., "A vector-free microfluidic platform for intracellular delivery," Proc. Natl. Acad. Sci. USA (Feb. 5, 2013), vol. 110, No. 6, Supporting Information. 10 pages.
Adamo, Andrea et al., "Microfluidics-Based Assessment of Cell Deformability," *Analytical Chemistry* (Aug. 7, 2012), vol. 84, No. 15, pp. 6438-6443.
Cross et al., "Nanomechanical analysis of cells from cancer patients," *Nature Nanotechnology* (Dec. 2007), vol. 2, pp. 780-783.
European Search Opinion dated Apr. 30, 2015 from European Application No. 12 841 329, 2 pp.
Griesbeck et al., "Sex Differences in Plasmacytoid Dendritic Cell Levels of IRF5 Drive higher IFN-alpha production in Women," *The Journal of Immunology* (Dec. 2015), vol. 195(11):5327-5336.
Han, X. et al., "CRISPR-Cas9 delivery to hard-to-transfect cells via membrane deformation," *Sci. Adv.*, Aug. 14, 2015, e1500454, 8 pp.

(56) References Cited

OTHER PUBLICATIONS

Hillerdal et al., "Systemic treatment with CAR-engineered T cells against PSCA delays subcutaneous tumor growth and prolongs survival of mice," *BMC Cancer* (Jan. 18, 2014), vol. 14, No. 30, pp. 1-9.
International Preliminary Report on Patentability dated Feb. 16, 2016 from International Application No. PCT/US2014/051343.
International Search Report and Written Opinion dated Feb. 1, 2016 from International Application No. PCT/US15/60689.
International Search Report and Written Opinion dated Mar. 11, 2016 from International Application No. PCT/US15/584489.
International Search Report and Written Opinion dated Mar. 21, 2016 from International Application No. PCT/US2016/013113.
International Search Report and Written Opinion dated Dec. 18, 2014 from International Application No. PCT/US2014/051343.
Lee et al., "Nonendocytic delivery of functional engineered nanoparticles into the cytoplasm of live cells using a novel, high-throughput microfluidic device," *Nano Letters* (2012), vol. 12, pp. 6322-6327.
Lin et al., "Highly selective biomechanical separation of cancer cells from leukocytes using microfluidic and hydrodynamic concentrator," *Biomicrofluidics* (Jun. 26, 2013), vol. 7, No. 3, pp. 34114-1-11.
Liu et al., "Molecular imaging in tracking tumor-specific cytotoxic T lymphocytes (CTLs)," *Theranostics* (Jul. 28, 2014), vol. 4, No. 10, pp. 990-1001.
Office Action dated Jun. 14, 2016 from European Application No. 12 841 329, 4 pp.
Office Action dated May 13, 2016 from Chinese Application No. 201280060689.6, 4 pp.
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "Plasma membrane recovery kinetics of a microfluidic intracellular delivery platform," *Integrative Biology* (2014), vol. 6, pp. 470-475.
Supplementary European Search Report dated Apr. 30, 2015 from European Application No. 12 841 329, 3 pp.
Third-Party Submission dated Oct. 23, 2015 from U.S. Appl. No. 14/352,354, 21 pp.
Zarnitsyn et al., "Electrosonic ejector microarray for drug and gene delivery," *Biomed Microdevices* (2008) 10:299-308.
International Search Report and Written Opinion dated Feb. 25, 2013 from International Application No. PCT/US12/060646.

\* cited by examiner
† cited by third party

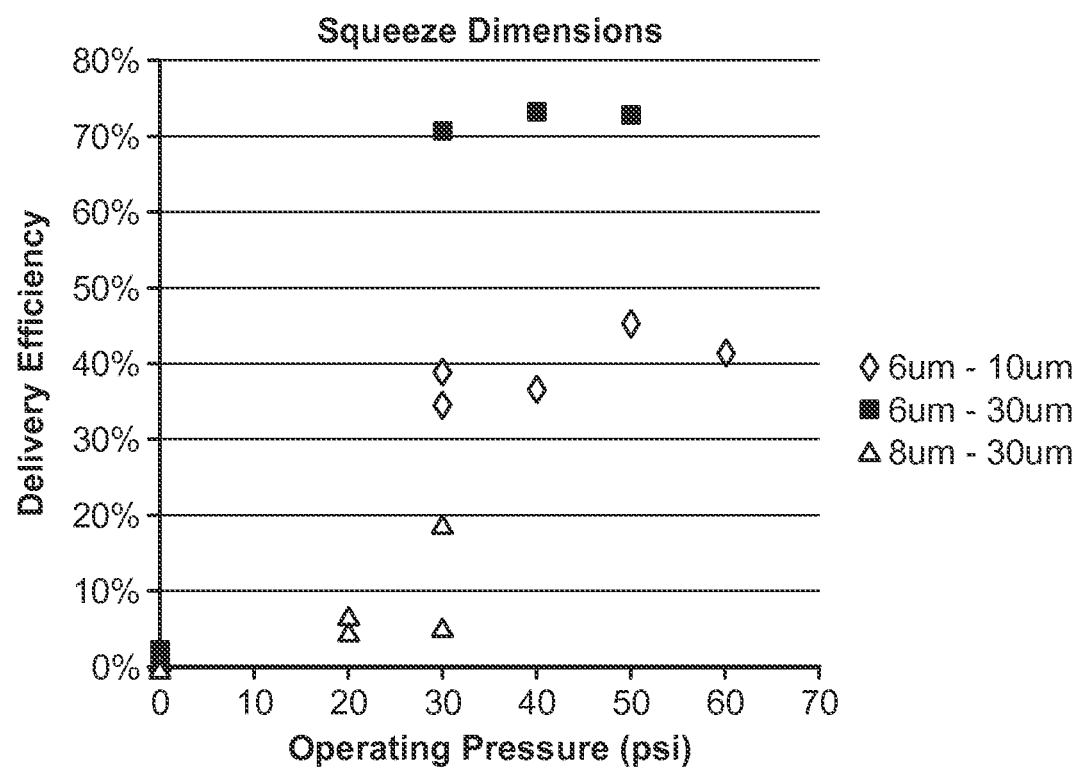
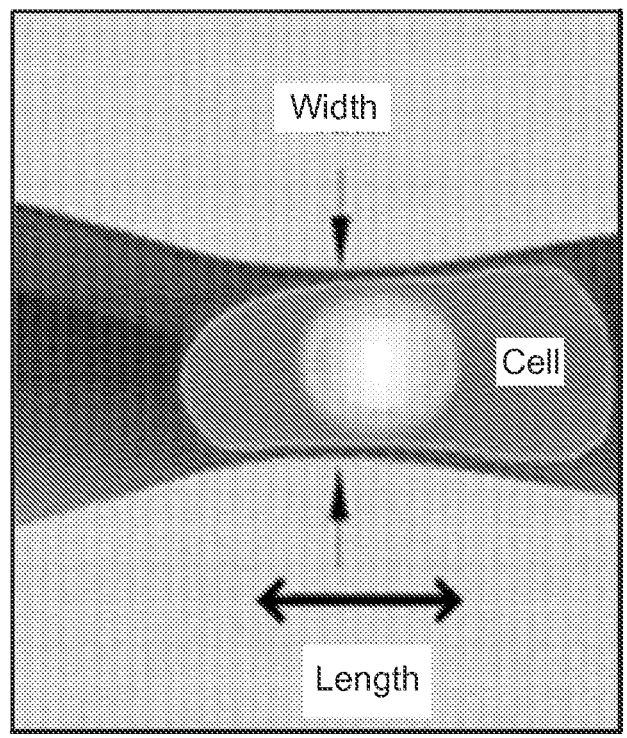
FIG. 13

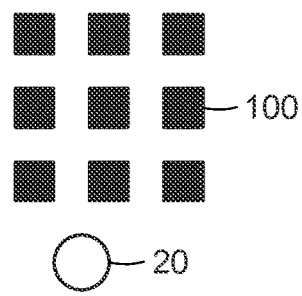
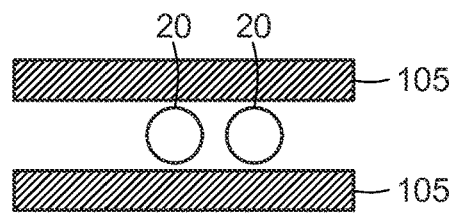
FIG. 16A  FIG. 16B
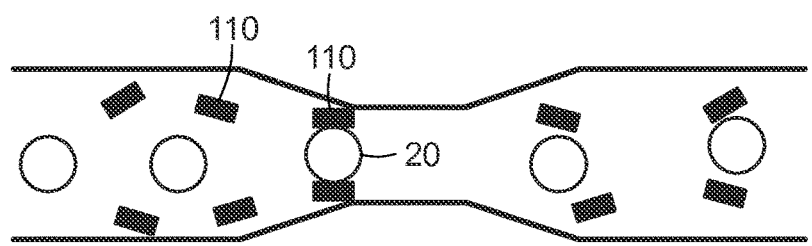
FIG. 16C
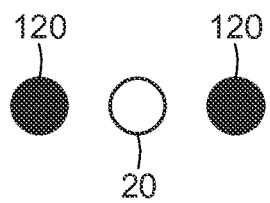 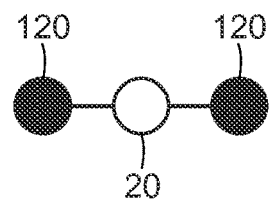
FIG. 16D  FIG. 16E
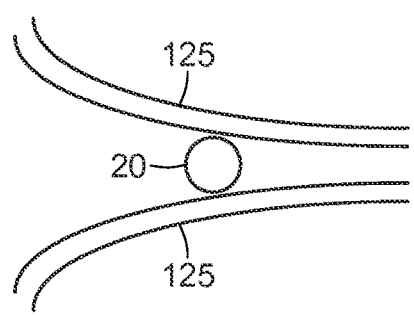
FIG. 16F

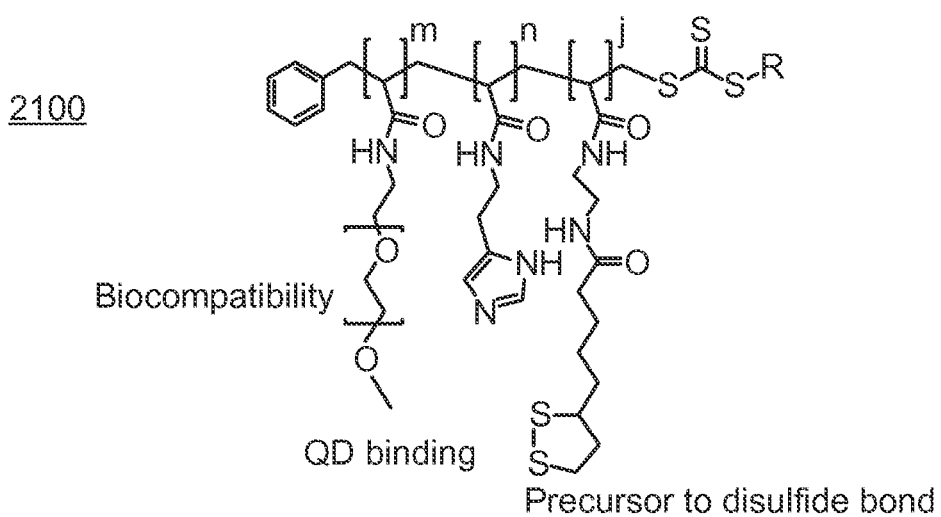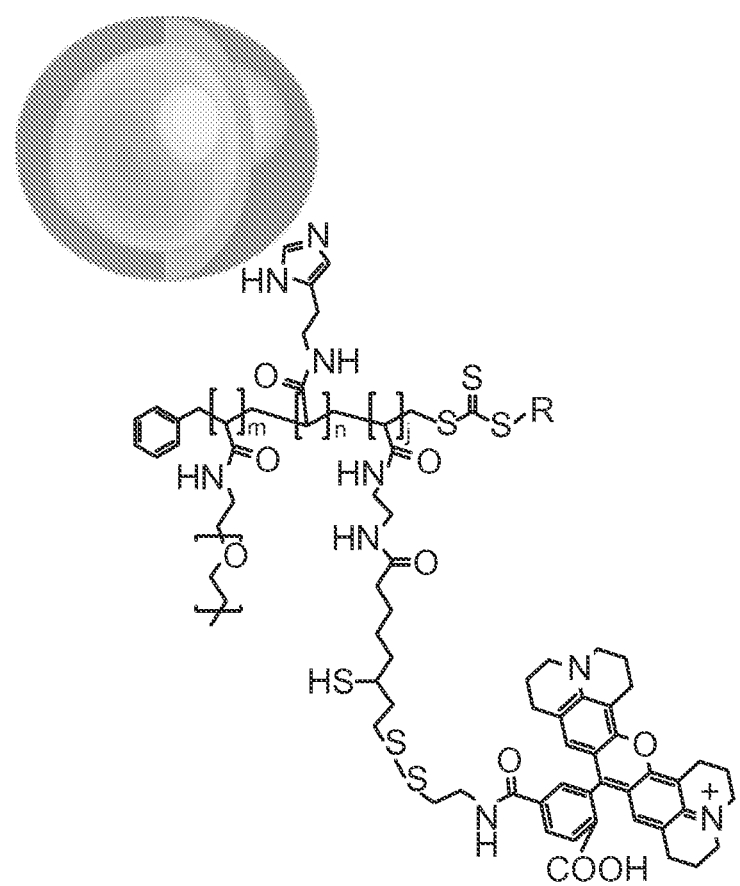
FIG. 21A

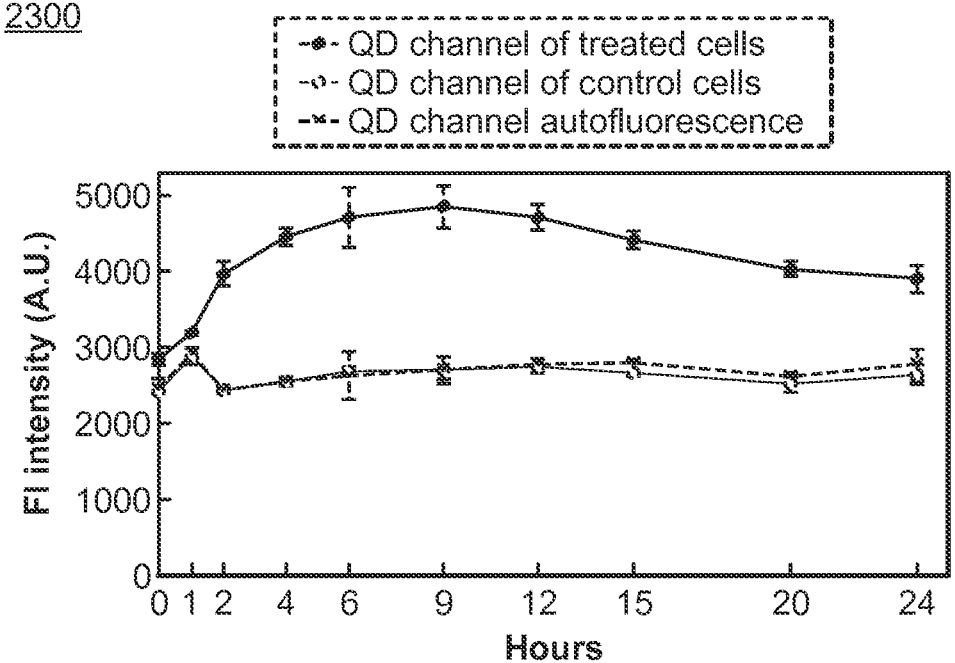
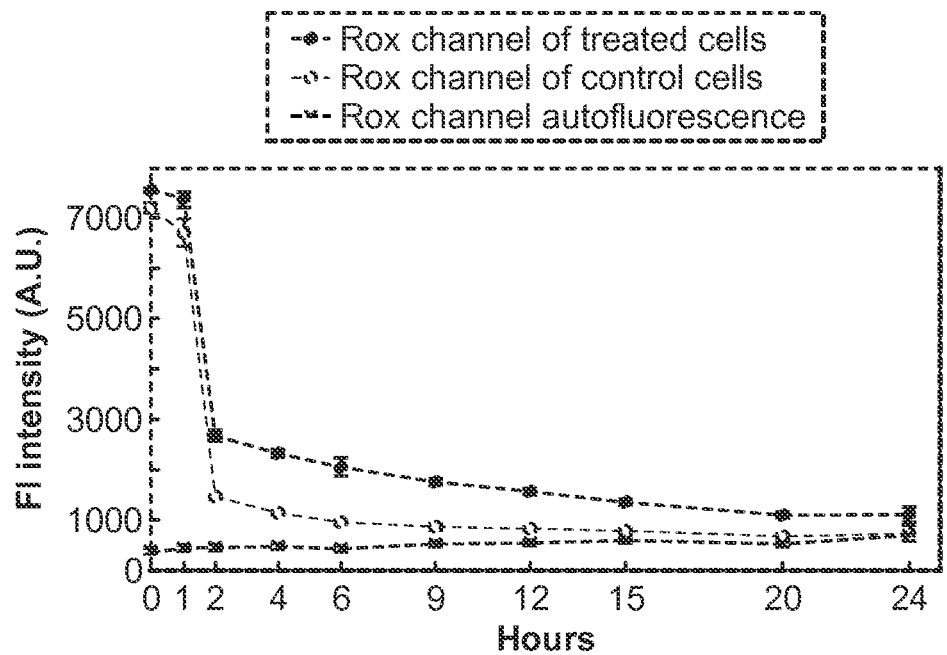
FIG. 23A

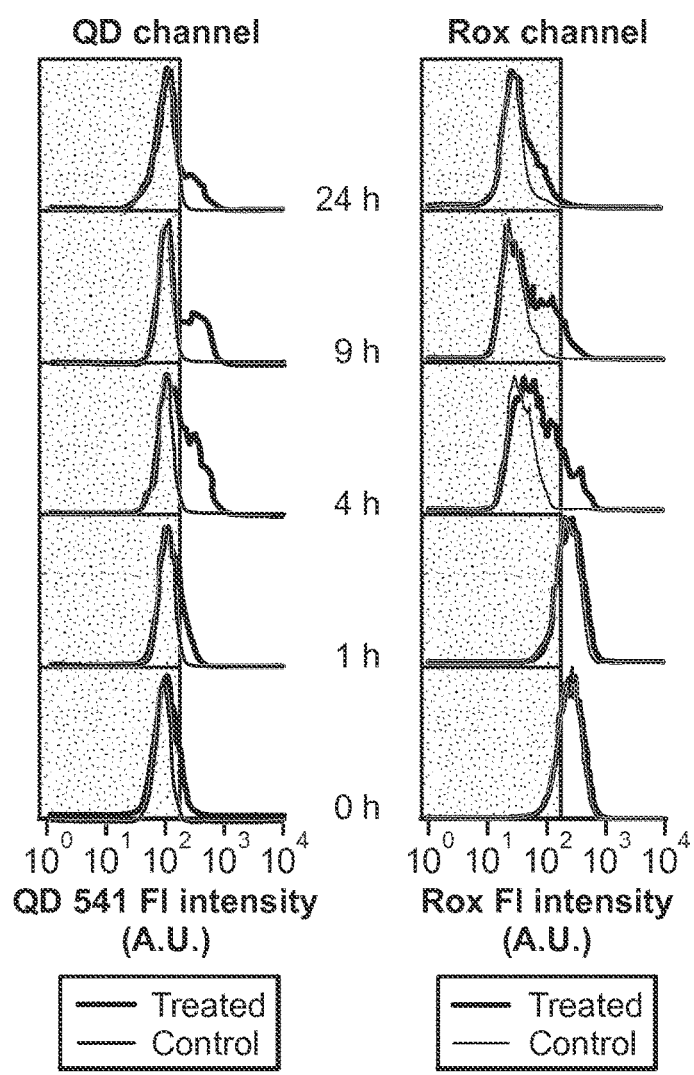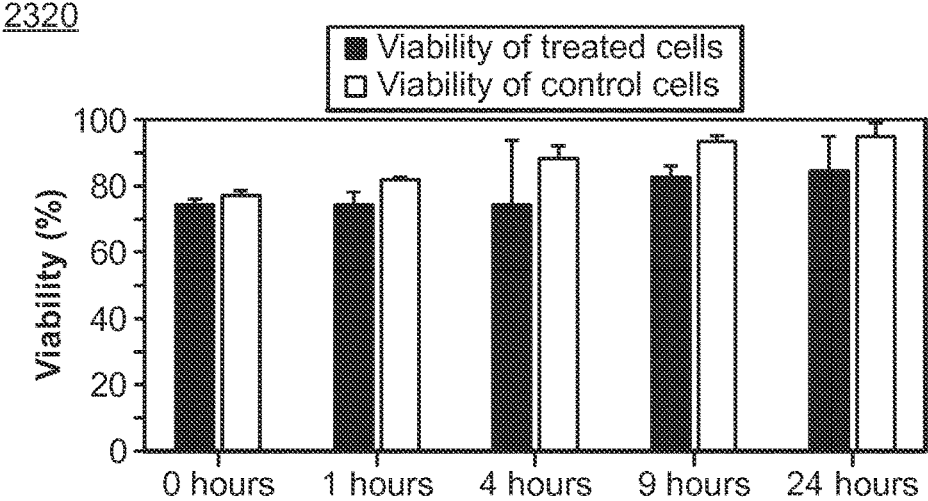
FIG. 23B

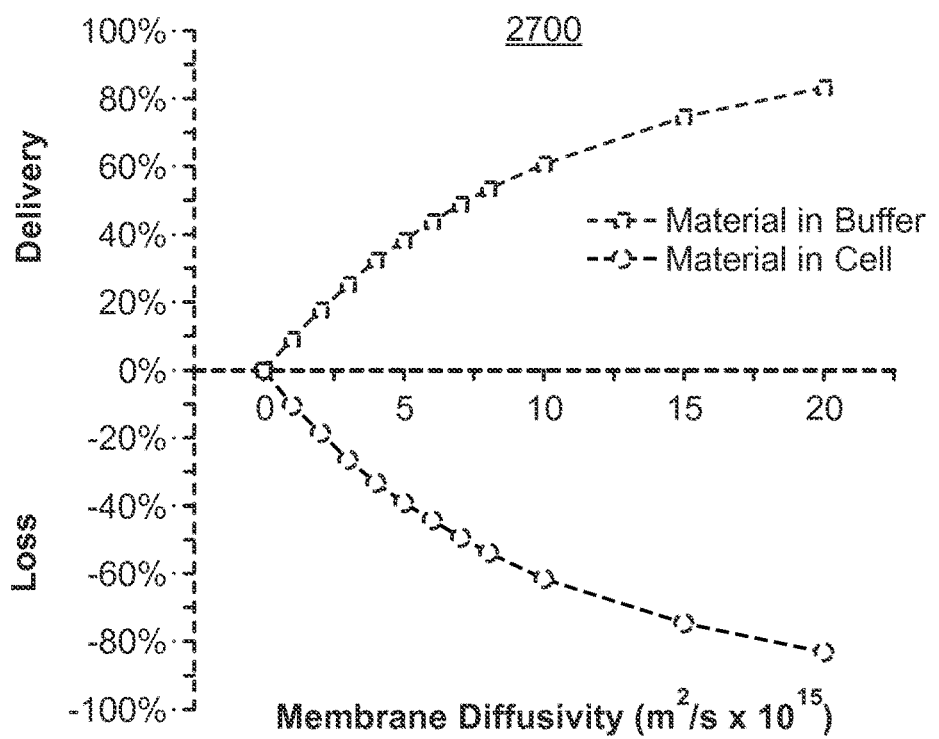
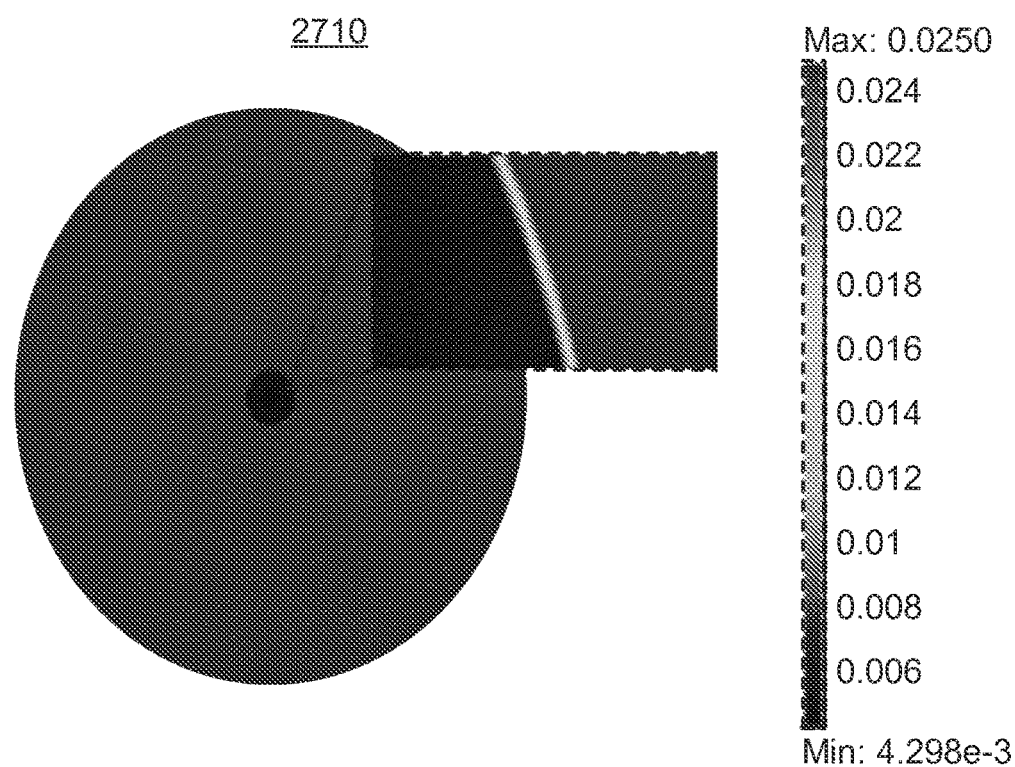
FIG. 27

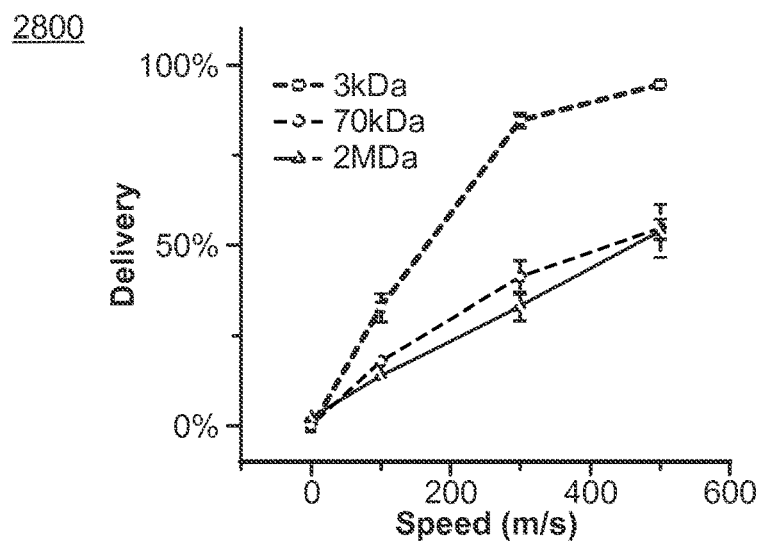
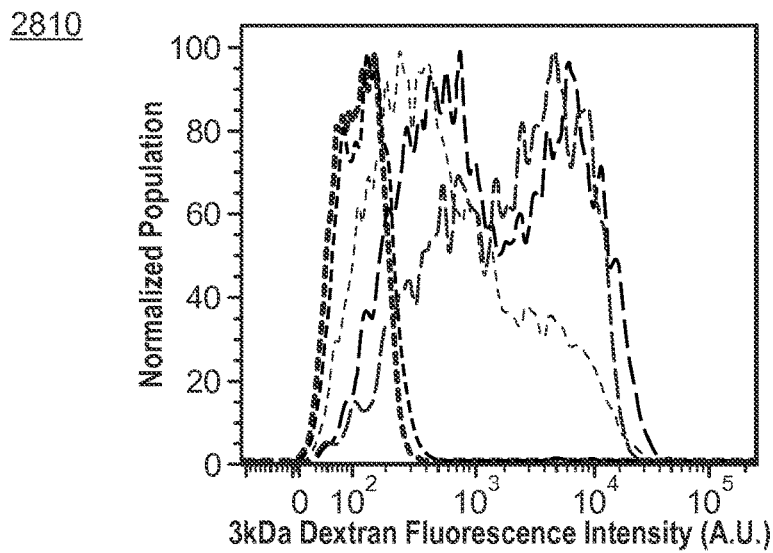
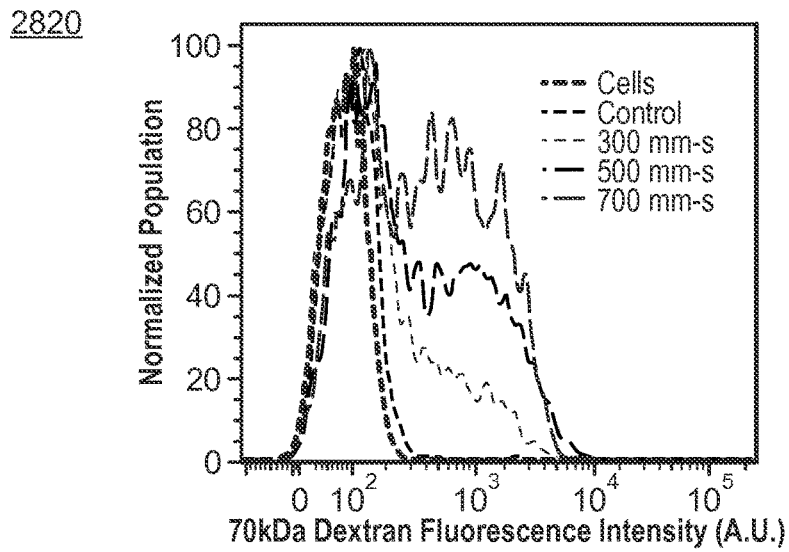
FIG. 28

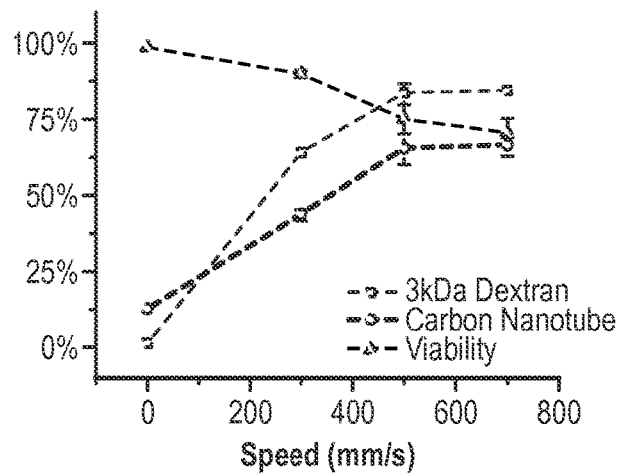
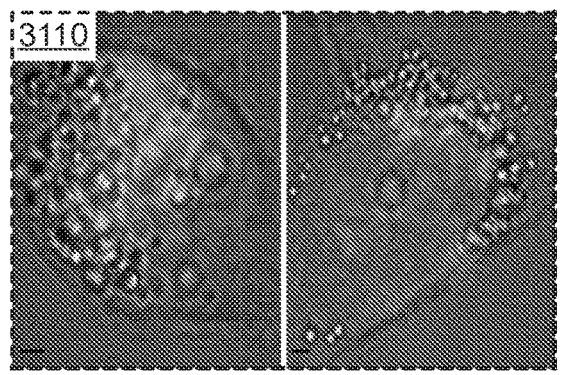
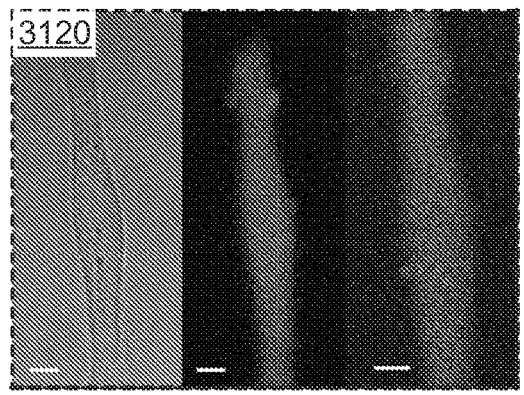
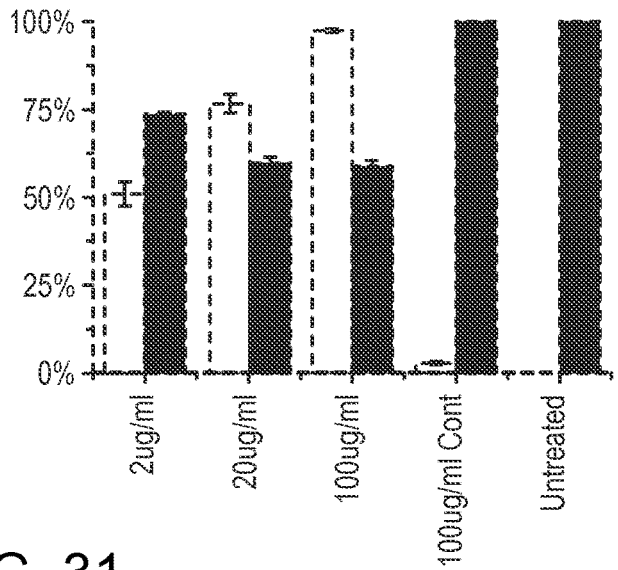
FIG. 31

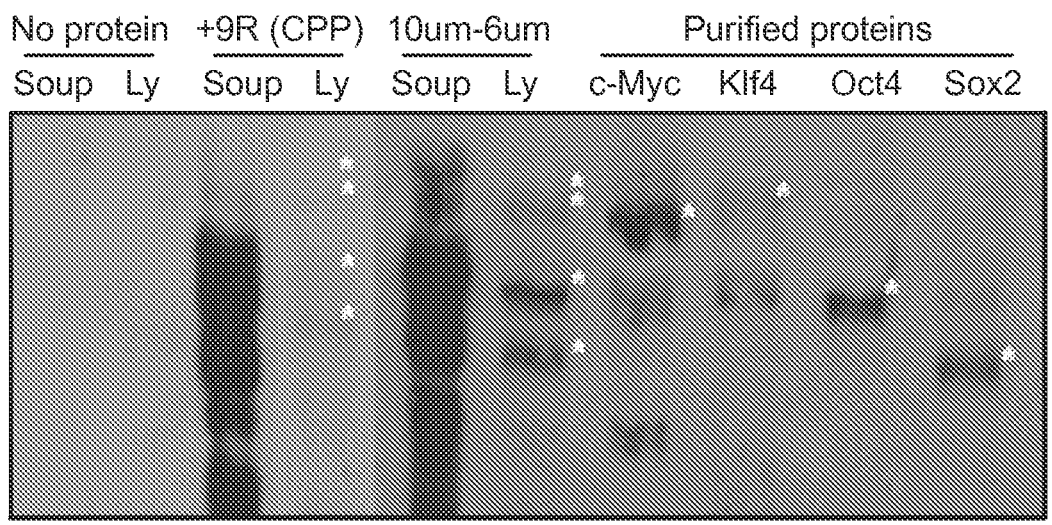
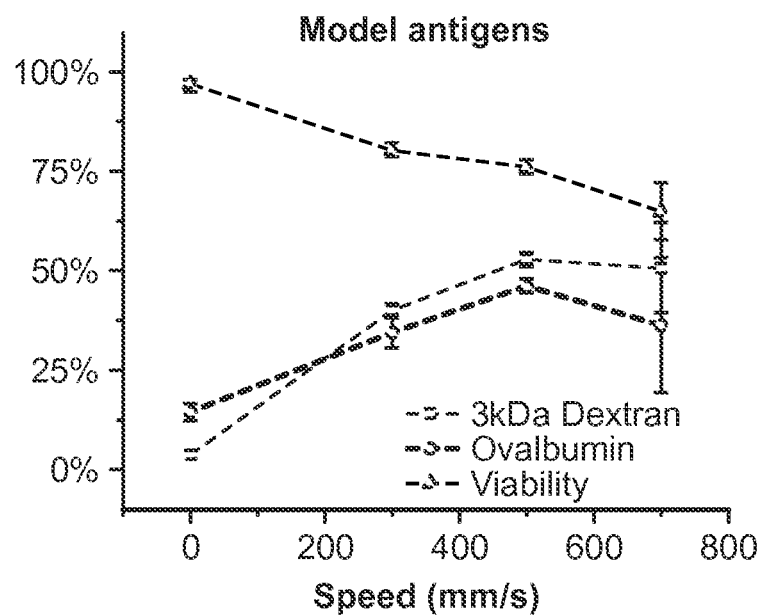
FIG. 32

| Cell Type | Primary/ Immortalized | Delivery by Rapid Mechanical Deformation |
|---|---|---|
| B Lymphocyte (mouse) | Primary | Dextran |
| DC 2.4 (mouse) | Immortalized | Dextran, Protein |
| Dendritic cell (mouse, spleen) | Primary | Dextran, Protein |
| Dendritic cell (mouse, bone marrow) | Primary | Dextran, Protein |
| Embryonic stem cell (mouse) | Primary | Dextran |
| Embryonic stem cell (human) | Primary | Dextran, siRNA |
| Fibroblasts (human, multiple sources) | Primary | Dextran, Protein |
| HeLa (human) | Immortalized | Dextran, siRNA, Protein, DNA, nanoparticles, Quantum Dots, Carbon Nanotubes |
| HT-29 (human) | Immortalized | Dextran |
| Macrophage (mouse) | Primary | Dextran |
| T Lymphocyte (mouse) | Primary | Dextran |

FIG. 33

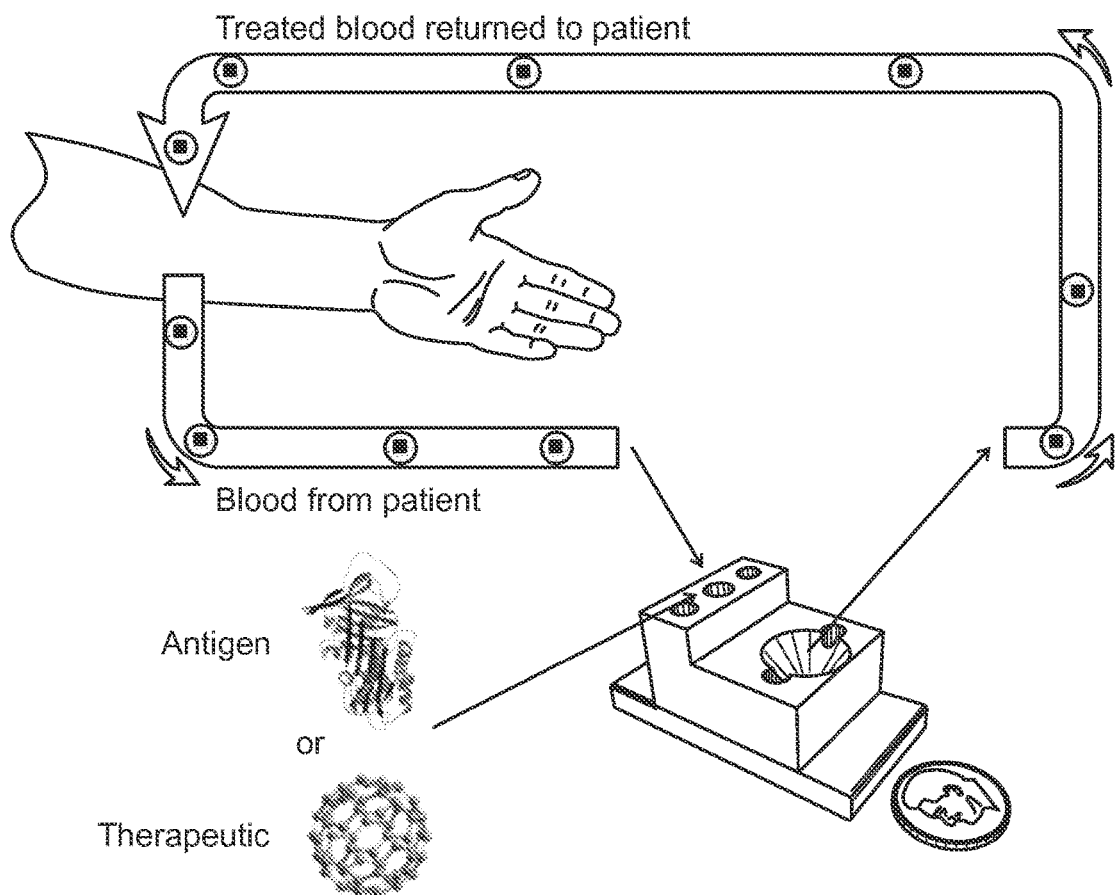

FIG. 34

3600
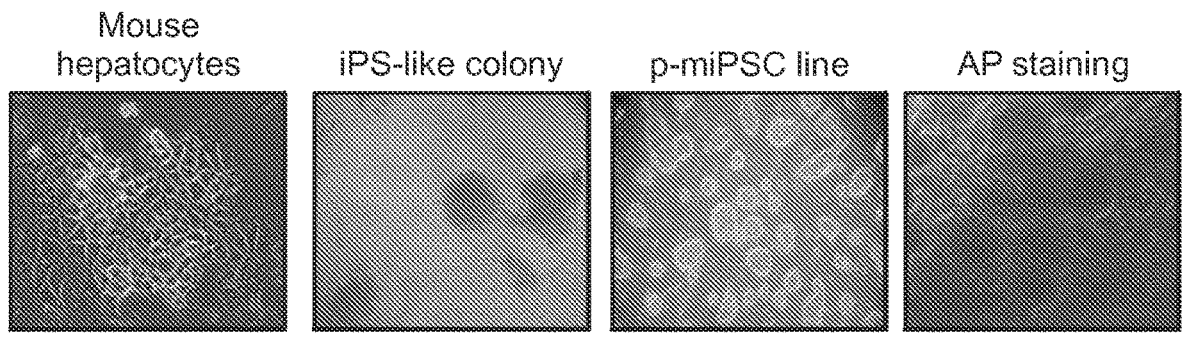
3610
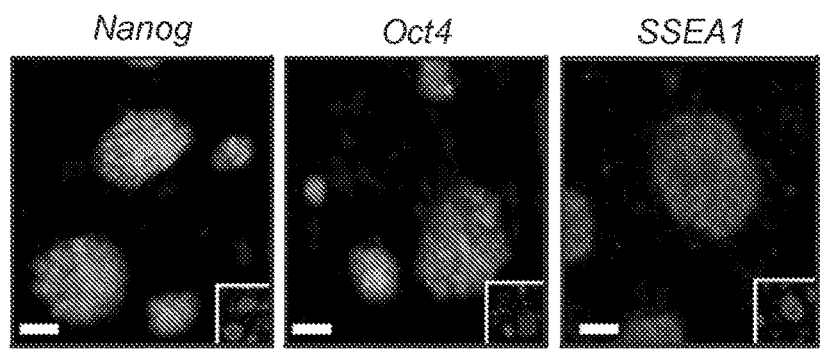
3620
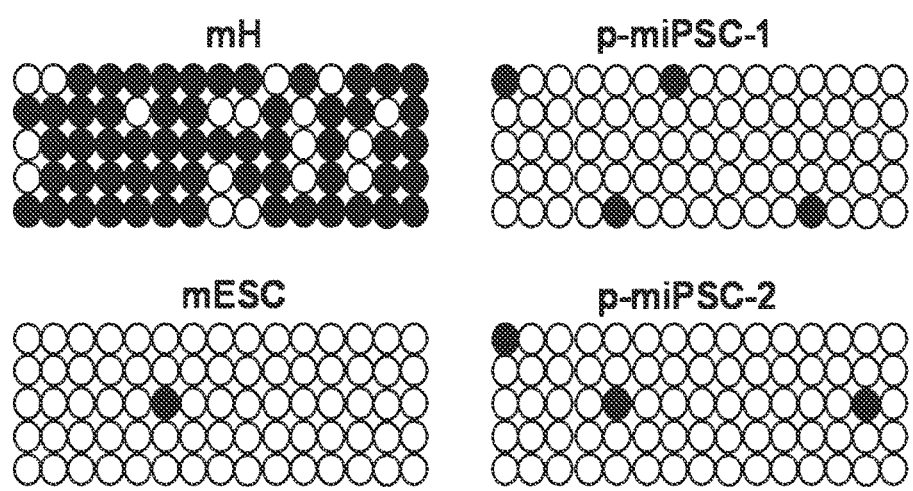
FIG. 36A

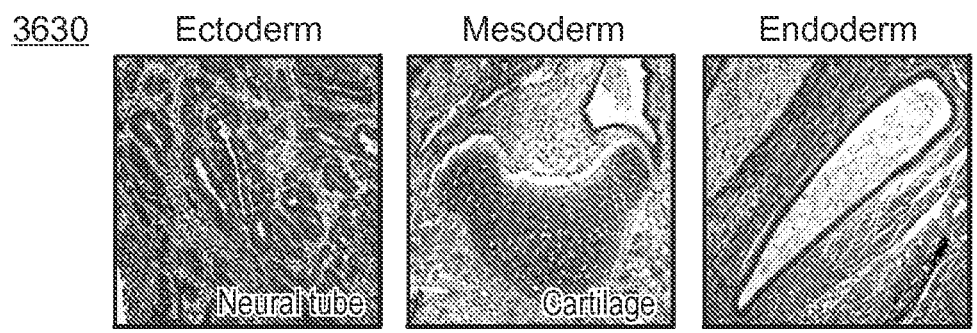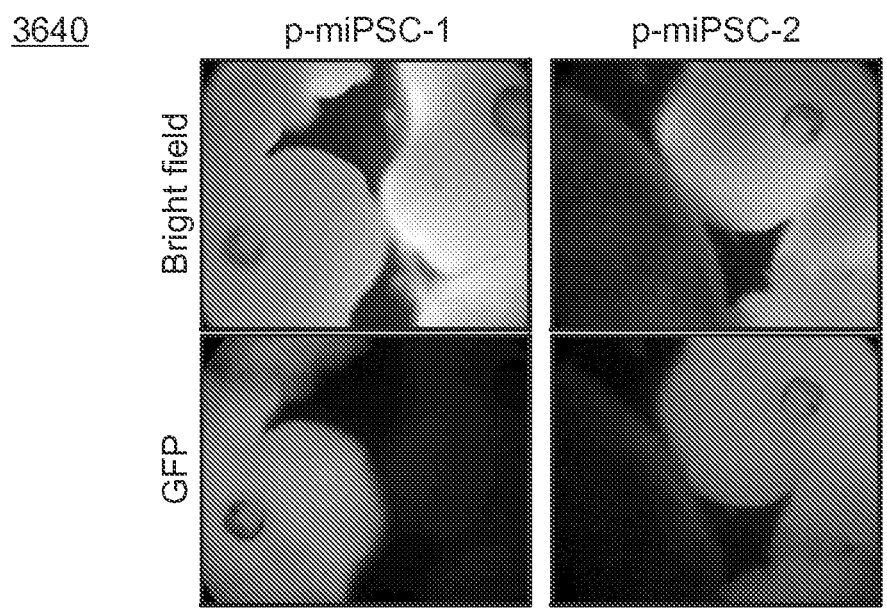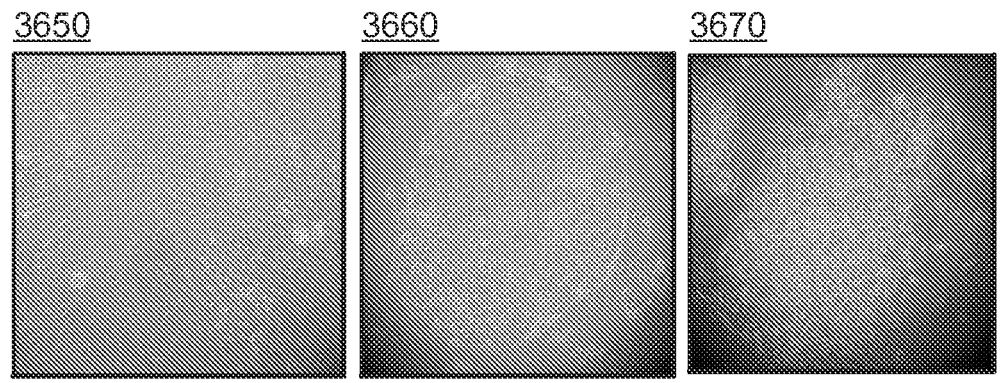
FIG. 36B

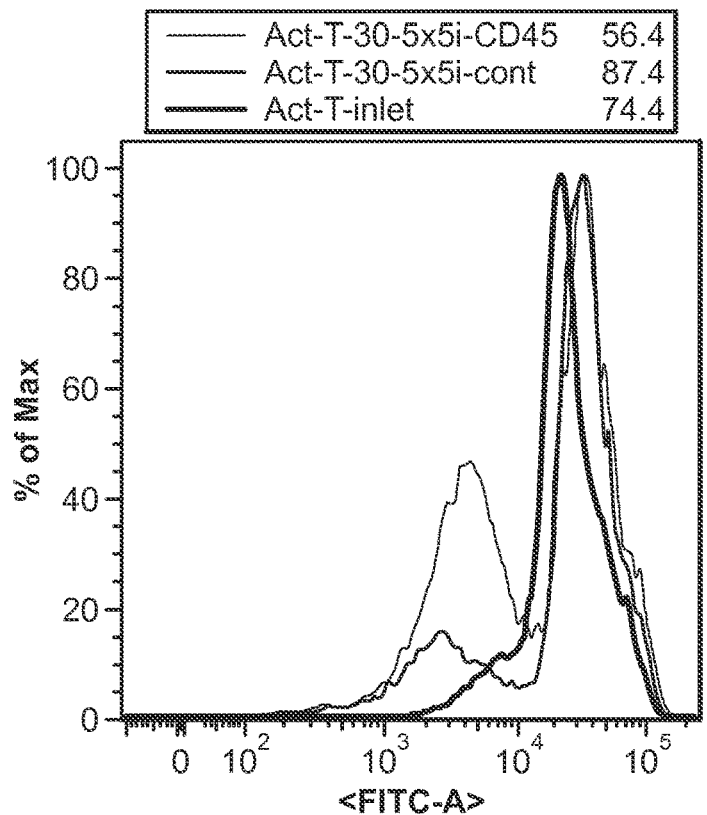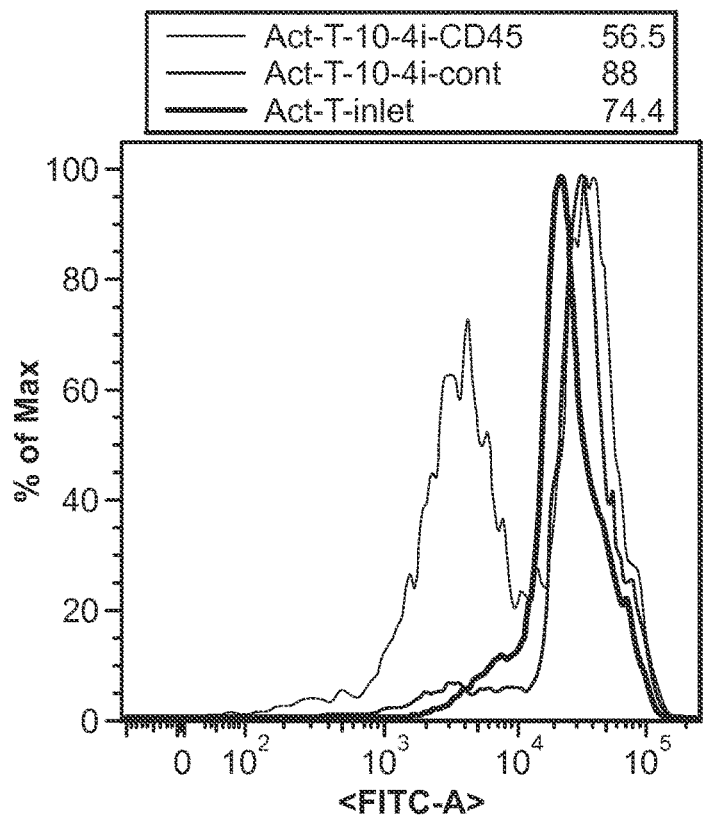
FIG. 41

INTRACELLULAR DELIVERY

RELATED APPLICATIONS

This application is a national stage application, filed under 35 U.S.C. § 371, of International Application No. PCT/US2012/060646 filed on Oct. 17, 2012, which claims the benefit of provisional applications U.S. Ser. No. 61/548,013 filed Oct. 17, 2011 and U.S. Ser. No. 61/684,301 filed Aug. 17, 2012, the contents which are each herein incorporated by reference in their entirety.

STATEMENT AS TO FEDERALLY-SPONSORED RESEARCH

This invention was made with Government support under Grant No. RC1 EB011187, awarded by the National Institutes of Health. The Government has certain rights in this invention.

BACKGROUND

Many pharmaceuticals largely focus on development of small-molecule drugs. These drugs are so-called due to their relatively small size that enables them to diffuse freely throughout the body to reach their target. These molecules are also capable of slipping across the otherwise impermeable cell membrane largely unhindered. The next generation of protein, DNA or RNA based therapies, however, cannot readily cross the cellular membrane and thus require cellular modification to facilitate delivery. Established methods use chemicals or electrical pulses to breach the membrane and deliver the material into the cytoplasm. Proper intracellular delivery is a critical step in the research, development and implementation of the next generation of therapeutics.

Existing methods are often difficult to develop and highly specific to their particular application. Moreover, many clinically important cell types, such as stem cells and immune cells, are not properly addressed by existing methods. There is thus a need for more robust and precise technique capable of addressing the needs of modern biological/medical research.

SUMMARY

The invention is based on the surprising discovery that a controlled injury, e.g., subjecting a cell to a constriction, rapid stretching, rapid compression, or pulse of high shear rate, leads to uptake of molecules into the cytoplasm of the cell from the surrounding cell medium. Thus, the invention features a vector-free microfluidic platform for direct-to-cytosol intracellular delivery of materials, e.g., a compound or composition, to a eukaryotic cell. The device is useful as a versatile and widely applicable laboratory tool to deliver desired molecules into target cells. The delivery of molecules into the cell using the methods described herein is proportional, e.g., linearly or monotonically with cell velocity through a constriction and/or pressure. For example, 50 µl of cell suspension goes through the device in a few seconds. The throughput ranges between 1 cell/second per channel (or even less) to over 1,000 cells/second per channel. Typical cell velocities through the constriction include 10 mm/second to 500 mm/second, although cell velocities can be up to 10 m/s (or even higher). Additional channels can be placed in parallel to increase the overall throughput of the system.

The uptake of molecule is diffusion-based rather than endocytosis i.e., payload (compound(s) to be delivered to the cell) are present in the cytoplasm rather than in endosomes following passage through the device. Little or no payload appears in endosomes following cell treatment. For example, large molecules are taken up more slowly than smaller molecules. Controlled cell stretching and velocity of movement of the cells through the constriction leads to superior delivery of target molecules while preserving the viability and integrity of the cells. After treatment, cell viability is between 70-100%, e.g., typical viability is 90% after treatment. By comparison, previous delivery methods using high shear rates alone for seconds or milliseconds have been shown to lead to poor viability of cells after treatment. In contrast to prior techniques, the methods of the invention subject the cells to a pulse of shearing ranging from 100-1000 Pa for a very short period of time (approximately 100 microseconds) as the cell passes through the constriction. The present techniques, however, are fundamentally different from previous techniques. In the present techniques, there is preferably an entire mechanical deformation of the cell as it passes through the constriction, which can impose different shearing forces than prior techniques. In preferred embodiments, the cells are not subject to an electric current. In other embodiments, a combination treatment is used, e.g., mechanical deformation using the device described herein followed by or preceded by electroporation (a type of osmotic transfection in which an electric current is used to produce temporary holes in cell membranes, allowing entry of nucleic acids or macromoles).

A payload is a compound or composition to be delivered into a cell. For example, a payload can include proteins, fluorescent dies, quantum dots, carbon nanotubes, RNA molecules, DNA molecules, antigens, and other macromolecules, nanoparticles, and compositions of matter.

The width of the constriction of the device, the length of the constricted portion, the geometry of the entrance region and the channel depth of the device influence the delivery of molecules into the cell. Preferably, the width of the constricted portion of the conduit is no less than 4 µm in diameter, and the length of the constricted portion of the conduit is preferably between 40-50 µm. The length of the constricted portion generally does not exceed 90 µm. The diameter of the constricted portion is related to the type of cell to be treated. As is described below, the diameter is less than the diameter of the cell (e.g., 20-99% of the diameter of the cell). Many cells are between 5-15 µm in diameter, e.g. dendritic cells are 7-8 µm in diameter. For example, the diameter of the constriction portion is 4.5, 5, 5.5, 6, or 6.5 µm for processing of single cells. In another example, the size/diameter of the constricted portion for processing of a human egg is between 6.2 µm and 8.4 µm, although larger and smaller constrictions are possible (diameter of a human ovum is approximately 12 µm). In yet another example, embryos (e.g., clusters of 2-3 cells) are processed using a constriction diameter of between 12 µm and 17 µm.

The device and methods are useful in vaccine development and production using professional antigen presenting cells such as dendritic cells. For example, a method of stimulating antigen presentation is carried out by subjecting a dendritic cell to a controlled injury such as transitory constriction or pulse of high shear and contacting the dendritic cell with a solution comprising a target antigen. The method yields highly activated antigen presenting cells compared to previous methods of stimulation. Vaccine production is carried out by propelling dendritic cells or other antigen presenting cells through the constriction-containing device (thereby subjecting the cells to a rapid stretching event) and then incubating the cells in a solution containing the payload, e.g., antigen. The cells are bathed in a cell culture medium containing one or more antigens after rapid deformation of the cells, but the cells may be contacted with the antigen prior to, during, and/or after the rapid deformation event/process.

Surfactants (e.g., 0.1-10% w/w) are optionally used (e.g., poloxamer, animal derived serum, albumin protein) in the flow buffer. Delivery of molecules into cells is not affected by the presence of surfactants; however, surfactants are optionally used to reduce clogging of the device during operation.

The device is made from silicon, metal (e.g., stainless steel), plastic (e.g., polystyrene), ceramics, or any other material suitable for etching micron scaled features and includes one or more channels or conduits through which cells pass. Silicon is particularly well suited, because micro patterning methods are well established with this material, thus it is easier to fabricate new devices, change designs, etc. Additionally, the stiffness of silicon can provide advantages over more flexible substrates like Polydimethylsiloxane (PDMS), e.g., higher delivery rates. For example, the device includes 2, 10, 20, 25, 45, 50 75, 100 or more channels. The device is microfabricated by etching the silicon. Cells are moved, e.g., pushed, through the channels or conduits by application of pressure. A cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net or closely-placed plates. In either case, the width of the constriction through which the cells traverse is 20-99% of the width or diameter of the cell to be treated in its natural, i.e., unstressed, state. Temperature can affect the uptake of compositions and affect viability. The methods are carried out at room temperature (e.g., 20° C.), physiological temperature (e.g., 39° C.), higher than physiological temperature, or reduced temperature (e.g., 4° C.), or temperatures between these exemplary temperatures.

Following controlled injury to the cell by constriction, stretching, and/or a pulse of high shear rate, the cells are incubated in a delivery solution that contains the compound or molecule that one wishes to introduce into the cell. Controlled injury may be characterized as small, e.g., 200 nm in diameter, defect in the cell membrane. The recovery period for the cells is on the order of a few minutes to close the injury caused by passing through the constriction. The delivery period comprises 1-10 minutes or longer, e.g., 15, 20, 30, 60 minutes or more, with 2-5 minutes being optimal when operated at room temperature. Longer time periods of incubation in the delivery solution do not necessarily yield increased uptake. For example, the data indicated that after 5 minutes, little or no additional material taken up by the cells.

Thus, the invention provides a solution to long-standing problems in the field of drug delivery to cells and to drawbacks associated with earlier methods.

With respect to delivery of material to a eukaryote cell, cells can be classified into two major categories:

1) Easy-to-deliver (ETD) cells: Most available chemical and viral methods fall under this category. Easy to deliver cells often have no direct clinical relevance.

2) Difficult-to-deliver (DTD) cells: High clinical relevance. Advancements in delivery technology can greatly enable/accelerate the development of novel therapies. This category includes stem cells, primary cells, and immune cells. The market for DTD delivery is expected to grow dramatically as novel RNA, stem cell, and protein based therapeutics gain momentum in the coming years.

The techniques described herein have proven especially useful to DTD research areas, although the same techniques can be used with ETD cells. In addition, it has facilitated the delivery of materials (such as quantum dots, carbon nanotubes and antibodies) that cannot be delivered effectively by any other method to either ETD or DTD cells.

In general, in an aspect, implementations of the invention can provide a microfluidic system for causing perturbations in a cell membrane, the system including a microfluidic channel defining a lumen and being configured such that a cell suspended in a buffer can pass therethrough, wherein the microfluidic channel includes a constriction, wherein a diameter of the constriction is a function of the diameter of the cell.

Implementations of the invention may also provide one or more of the following features. The diameter of the constriction is substantially 20-99% of the diameter of the cell passing therethrough. A cross-section of the channel is selected from the group consisting of circular, elliptical, an elongated slit, square, hexagonal, and triangular. The constriction includes an entrance portion, a centerpoint, and an exit portion. The entrance portion defines a constriction angle, wherein the constriction angle is optimized to reduce clogging of the channel. The microfluidic system further includes a plurality of the microfluidic channels arranged in parallel, e.g., 2, 5, 10, 20, 40, 45, 50, 75, 100, 500, 1,000 or more.

In general, in another aspect, implementations of the invention can also provide a method for delivering a compound into a cell, the method including providing a cell in suspension or suspending a cell and a payload in a solution, passing the solution through a microfluidic channel that includes a constriction, sizing the constriction as a function of the diameter of the cell, passing the cell through the constriction such that a pressure is applied to the cell causing perturbations of the cell large enough for the payload to pass through, and incubating the cell in the solution for a predetermined time after it passes through the constriction.

Implementations of the invention may also provide one or more of the following features. A diameter of the constriction is substantially 20-99% of the diameter of the cell. A cross-section of the microfluidic channel is selected from the group consisting of circular, elliptical, an elongated slit, square, hexagonal, and triangular. Passing the solution includes passing the solution through an entrance portion, a centerpoint, and an exit portion of the constriction. The method further includes reducing clogging of the microfluidic channel by adjusting a constriction angle of the entrance portion. The solution includes passing the solution through a plurality of microfluidic channels arranged in parallel.

In general, in still another aspect implementations of the invention can also provide a method for delivering a compound into a cell, the method including providing a cell in a solution or suspending a cell in a solution, passing the solution through a microfluidic channel that includes a constriction, sizing the constriction as a function of the diameter of the cell, passing the cell through the constriction such that a pressure is applied to the cell causing perturbations of the cell, and incubating the cell in the solution containing a payload for a predetermined time after it passes through the constriction, wherein the perturbations are large enough for the payload to pass through.

Implementations of the invention may also provide one or more of the following features. A diameter of the constriction is substantially 20-99% of the diameter of the cell. A cross-section of the microfluidic channel is selected from the group consisting of circular, elliptical, an elongated slit, square, hexagonal, and triangular. Passing the solution includes passing the solution through an entrance portion, a centerpoint, and an exit portion of the constriction. The method further includes reducing clogging of the microfluidic channel by adjusting a constriction angle of the entrance portion. Passing the solution includes passing the solution through a plurality of microfluidic channels arranged in one of series and parallel. Incubating includes incubating the cell for 0.0001 seconds to 20 minutes (or even longer). The pressure is one of shearing and compression.

In general, in yet another aspect, implementations of the invention can also provide a method for delivering a compound into a cell, the method including providing a cell in a solution or suspending a cell in a solution, deforming the cell such that perturbations are caused in a membrane of the cell, and incubating the cell in the solution with a payload after the cell has been deformed.

Implementations of the invention may also provide one or more of the following features. Deforming the cell includes deforming the cell for 1 μs to 10 ms, e.g., 10 μs, 50 μs, 100 μs, 500 μs, and 750 μs. Incubating occurs for 0.0001 seconds to 20 minutes, e.g., 1 second, 30 seconds, 90 seconds, 270 seconds, and 900 seconds.

Various implementations of the invention may provide one or more of the following capabilities. Greater precision and scalability of delivery can be achieved when compared with prior techniques. Delivery of a material to a cell can be automated. Material such as proteins, RNA, siRNA, peptides, DNA, and impermeable dye can be implanted into a cell, such as embryonic stem cells or induced pluripotent stem cells (iPSCs), primary cells or immortalized cell lines. The device and methods are amenable to any cell type, and the size of the constricted portion is tailored to the of the cell to be treated. The devices and methods can provide significant advantages. For example, experimental noise in current systems can be reduced when compared with prior techniques. Delivery quantities of a material can be consistent across the cell population. Cells can be individually handled rather than being handled as a batch. The invention has also demonstrated a fairly unique opportunity to deliver a variety of nanoparticles and proteins to the cytosol. Existing methods are fairly unreliable or inefficient at performing such functions.

With respect to delivery of sensitive payloads, e.g., proteins (especially large proteins, e.g., greater than 30, 50, 100, 150, 200, 300, 400, 500 kDa or more), quantum dots, or other payloads that are sensitive to or damaged by exposure to electricity, are reliably delivered into cells while preserving the integrity and activity of the sensitive payload. Thus, the device and methods have significant advantages over existing techniques such as electroporation, which subjects payload compositions to electricity (thereby damaging the payload) and leads to low cell viability (e.g., 505 or more of the cells typically die after electroporation). Another advantage of the rapid stretch/deformation method is that stem or precursor cells are rendered receptive to uptake of payload without altering the state of differentiation or activity of the treated cell. In addition to delivery of compositions into the cytoplasm of the cell for therapeutic purposes, e.g., vaccine production, the method is used to introduce molecules, e.g., large molecules comprising a detectable marker, to label intracellular structures such as organelles or to label intracellular constituents for diagnostic or imaging purposes.

Various implementations of the invention may also provide one or more of the following capabilities. DNA can be delivered into dose-to-deliver cells such as stem, primary, immune cells. Delivery of very large plasmids (even entire chromosomes) can be accomplished. Quantitative delivery into cells of known amount of a gene construct to study the expression level of a gene of interest and its sensitivity to concentration can also readily be accomplished. Delivery of known amounts of DNA sequences together with known amount of enzymes that enhance DNA recombination in order to achieve easier/more efficient stable delivery, homologous recombination, and site-specific mutagenesis can be accomplished. The methods and devices described herein can also be useful for quantitative delivery of RNA for more efficient/conclusive RNA studies. Delivery of small interfering RNA (siRNA) into the cytoplasm of a cell is also readily accomplished.

Various implementations of the invention may also provide one or more of the following capabilities. RNA can be delivered into a cell for RNA silencing without the need for liposomes. Known amounts of RNA molecules together with known amounts of dicer molecules can be delivered to achieve standardized, efficient, RNA across multiple cell lines in different conditions. mRNA can be delivered into cells to study aspects of gene expression regulations at the posttranscriptional level. Known amounts of label of RNA to study the half-life of RNAs and cells can be possible. Universal protein delivery can be achieved. Known amounts of label proteins can be delivered to study their half-life in cells. Delivery of label proteins to study protein localization can be accomplished. Known amounts of tagged proteins can be delivered to study protein-protein interactions in the cellular environment. Delivery of labeled antibodies into living cells for immunostaining and fluorescence-based Western blotting can be achieved.

Various implementations of the invention may also provide one or more of the following clinical and research capabilities. Quantitative delivery of drugs to cell models for improved screening and dosage studies can be achieved. The method could be deployed as a high throughput method of screening protein activity in the cytosol to help identify protein therapeutics or understand disease mechanisms. Such applications are presently severely limited by current protein delivery methods due to their inefficiencies. The devices and techniques are useful for intracellular delivery of drugs to a specific subset of circulating blood cells (e.g. lymphocytes), high throughput delivery of sugars into cells to improve cryopreservation of cells, especially oocytes, targeted cell differentiation by introducing proteins, mRNA, DNA and/or growth factors, delivery of genetic or protein material to induce cell reprogramming to produce iPS cells, delivery of DNA and/or recombination enzymes into embryonic stem cells for the development of transgenic stem cell lines, delivery of DNA and/or recombination enzymes into zygotes for the development of transgenic organisms, DC cell activation, iPSC generation, and stem cell differentiation, nano particle delivery for diagnostics and/or mechanic studies as well as introduction of quantum dots. Skin cells used in connection with plastic surgery are also modified using the devices and method described herein.

A method of stimulating antigen presentation using the method to deliver antigen and/or immune stimulatory molecules yields antigen presenting cells, e.g., dendritic cells, with improved levels of activity compared to convention methods of stimulation, thereby leading to increased levels of T and B-cell mediated immunity to a target antigen. Such a method could thus be employed as a means of activating the immune system in response to cancer or infections For screening, imaging, or diagnostic purposes, the device is used in a method of labeling cells. A method of labeling a cell is carried out by subjecting a cell to a controlled injury and contacting the cell with a solution comprising a detectable marker, wherein said injury comprises a transitory constriction or pulse of high shear. The detectable marker comprises a fluorescent molecule, a radionuclide, quantum dots, gold nanoparticles, or magnetic beads.

Prior to the invention, manipulation of stem cells for the purpose of introducing exogenous compositions has been difficult. The device and methods described herein, e.g., passage of stem cells or progenitor cells such as induced pluripotent stem cells (iPSCs) through a constriction channel does not induce differentiation, but does reliably induce uptake of compositions into the cell. For example, differentiation factors are introduced into such cells. After uptake of introduced factors, the cells proceed on a differentiation pathway dictated by the introduced factor without complications associated with the method by which the factor(s) was introduced into the cell.

In addition to single cells, even very large cells, e.g., eggs; approximately 200 µm in diameter, clusters of cells, e.g., 2-5 cell clusters such as an embryo comprising 2-3 cells, are treated to take up target compositions. The size of the aperture is adjusted accordingly, i.e., such that the width of the constriction is just below the size of the cluster. For example, the width of the channel is 20-99% of the width of the cell cluster.

Cells or cell clusters are purified/isolated or enriched for the desired cell type. Dendritic cells or other cells, e.g., immune cells such as macrophages, B cells, T cells, or stem cells such as embryonic stem cells or iPS, used in the methods are purified or enriched. For example, cells are isolated or enriched by virtue of their expression of cell surface markers or other identifying characteristics. Dendritic cells are identified and isolated by virtue of their expression of the β-intergrin, CD11c or other identifying cell surface markers. With regard to cells, the term "isolated" means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

Payload compositions such as polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

A suspension solution is any physiologic or cell-compatible buffer or solution. For example, a suspension solution is cell culture media or phosphate-buffered saline. A payload is the same or different suspension solution, which also contains the composition intended to be delivered inside the cell.

Advantages of the device include avoiding modification of the desired payload, and not necessarily exposing the payload to any electromagnetic fields or other forms of stress. With respect to electroporation, this method has been shown to damage proteins and be ineffective in delivery. This significant drawback is not an issue with the method described herein; the present method is particularly suitable for delivery of sensitive payloads, e.g., proteins, particularly large proteins (e.g., 40 kDa-70 kDa, and up to 120, 130, 150, 200 kDa or more), large nucleic acid constructs (e.g., plasmids and other constructs containing 1 kb, 2 kb, 5 kb, or more of nucleic acid polymers and up to entire chromosomes), large compounds, as well as quantum dots (e.g., 12 nm in diameter) and other materials that are known to be sensitive and easily damaged upon exposure to electricity. For example, the surface ligands on a nanoparticle or quantum dot can be damaged or become charged in response to an electric field thus resulting in aggregation of the particles thereby limiting/eliminating their functionality. Yet another advantage of the controlled injury method is the timing of contacting the cells with the delivery composition. Particularly relevant for proteins, which are sensitive to proteases, temperature, as well as electricity, cells are contacted with payload solution after treatment and for a relatively short period of time compared to earlier methods. The microfluidic nature of the device also requires far smaller working volumes thereby conserving precious raw materials and/or cells. The device can also be coupled with existing delivery methods such as electroporation or liposomes to produce a greatly enhanced delivery relative to each method individually.

Functional activity of delivered payload is inversely correlated to fluid shear stress, i.e., physical strain to the cell membrane such as stretching of the cell membrane mediates uptake of payload rather than shear. Conventional nanoparticle delivery methods may result in greater amounts of material gaining access to the intracellular environment of the cell; however, those methods lead to less activity of the delivered material compared to the methods described herein due to the fact that previous methods result in sequestration of the delivered material in endosomes. The methods described herein lead to direct-to-cytosol delivery of compounds/compositions such that a lesser amount of payload delivered into the cell leads to a greater amount of functional activity of the delivered molecules due to their accessibility to other cytosolic components. For example, earlier methods for delivering nanoparticles have resulted in 2-10 times the amount of delivered material into the cell but with little or no functional activity of the delivered material due to sequestration in endosomes. The devices and methods of the invention overcome this drawback of previous intracellular delivery methods by avoiding the endosomal compartment.

Additional advantages and features include time scale of treatment and cell speeds that are much faster than earlier approaches. Moreover, other methods do not squeeze the cells as hard as the present methods, e.g., as determined by size (diameter) of cell relative to size (diameter) of constriction (as a % of the diameter of the cell). This rapid, forceful, but sub-leather, squeeze or deformation leads to superior results in direct-to-cytosol payload uptake by cells. Deformation of the cell is sudden, i.e., occurs over substantially 1 µs to 1 ms. In general, too much deformation induced cell stress can be lethal to the cell, while at the same time, too little stress does not induce cell perturbations. Therefore the current subject matter provides methods and systems that cause sufficient stress to induce temporary perturbations but not so much stress that the perturbations are permanent and lethal to the cell.

Any of the methods described above are carried out in vitro, ex vivo, or in vivo. For in vivo applications, the device may be implanted in a vascular lumen, e.g., an in-line stent. These and other capabilities of the invention, along with the invention itself, will be more fully understood after a review of the following figures, detailed description, and claims.

BRIEF DESCRIPTION OF THE FIGURES

FIG. 13 is a graph showing exemplary results obtained from cells that were processed using a microfluidic system.

FIGS. 16a-16f are exemplary schematic diagrams of microfluidic systems.

FIG. 23 illustrates flow cytometry measurements of average cell fluorescence and viability.

FIG. 27 illustrates a simplified, 2D diffusion model that simulates passive diffusion of material into a cell across a porated membrane.

FIG. 28 illustrates the results of a two-tiered delivery of material.

FIG. 31 illustrates data from nanomaterial and antibody delivery.

FIG. 32 illustrates protein delivery applications.

FIG. 33 is a table of exemplary cell types, which payload has successfully been delivered.

FIG. 34 is an illustration depicting a system in which a patient's blood is treated by a microfluidic device for the delivery of payload such as macromolecules.

FIG. 36 depicts generation and characterization of mouse and human iPSC lines by direct delivery of fused reprogramming proteins using the current subject matter.

FIG. 41 is a histogram of CD45 expression of activated T cells as measured by an Alexa 488 antibody to CD45. Cells that are treated by the device in the presence of CD45 silencing RNA exhibit a lower fluorescence intensity peak thereby indicating knockdown of CD45 gene expression.

DETAILED DESCRIPTION

Embodiments of the invention provide techniques for applying controlled deformation to a cell for a predetermined amount of time in order to cause perturbations in the cell membrane such that materials can be delivered to the inside of the cell. The deformation can be caused by, for example, pressure induced by mechanical strain or shear forces. In one example, a microfluidic system includes a structure that controls and/or manipulates fluids by geometrically confining the fluids on a small scale (eg., sub milliliter volumes such as microlitres, nanoliters, or picoliters). The microfluidic system is capable of intracellularly delivering virtually any payload into a cell. The system consists of one or more microfluidic channels with a constriction that the cells pass through. Preferably, the cells flow through the microfluidic channel suspended in a liquid medium that is pressure driven through the system. When a cell passes through the constriction, its membrane is perturbed causing temporary disruptions in the membrane and resulting in the uptake of the payload that is present in the surrounding media. The constriction is a function of the size of the target cell, but preferably on the same order or smaller than the cell diameter. Multiple constrictions can be placed in parallel and/or series. The perturbation in the cell is a breach in the cell that allows material from outside the cell to move into the cell (e.g., a hole, tear, cavity, aperture, pore, break, gap, perforation). The perturbations (e.g., pores or holes) created by the methods described herein are not formed as a result of assembly of protein subunits to form a multimeric pore structure such as that created by complement or bacterial hemolysins. Other embodiments are within the scope of the described subject matter.

Figure 1A:
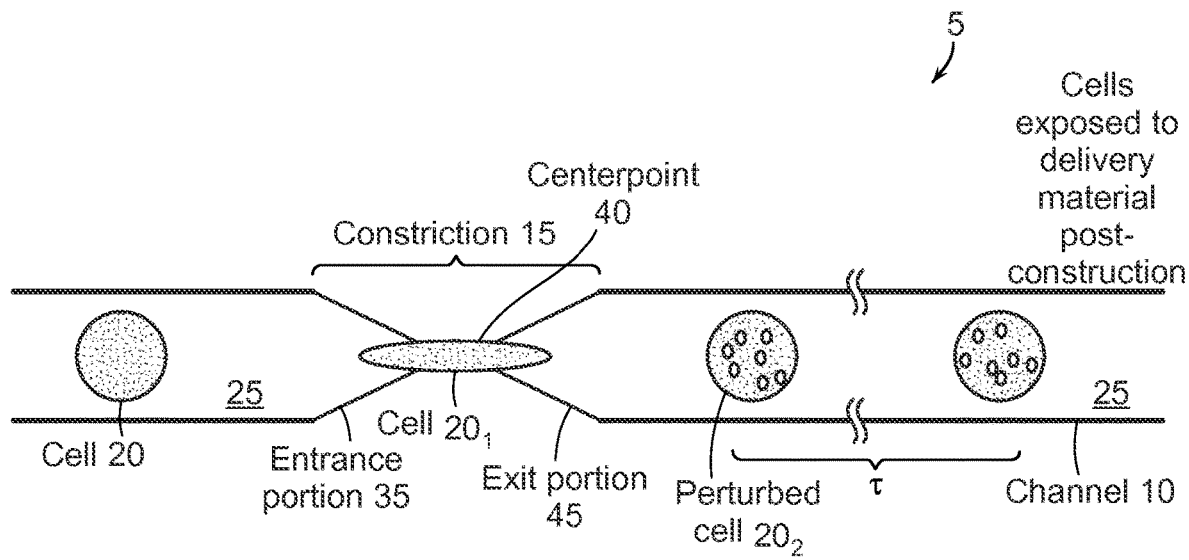
FIG. 1a is a schematic diagram of a microfluidic system. Cells are exposed to the delivery material (payload) after passing through the constriction.
Figure 1B:
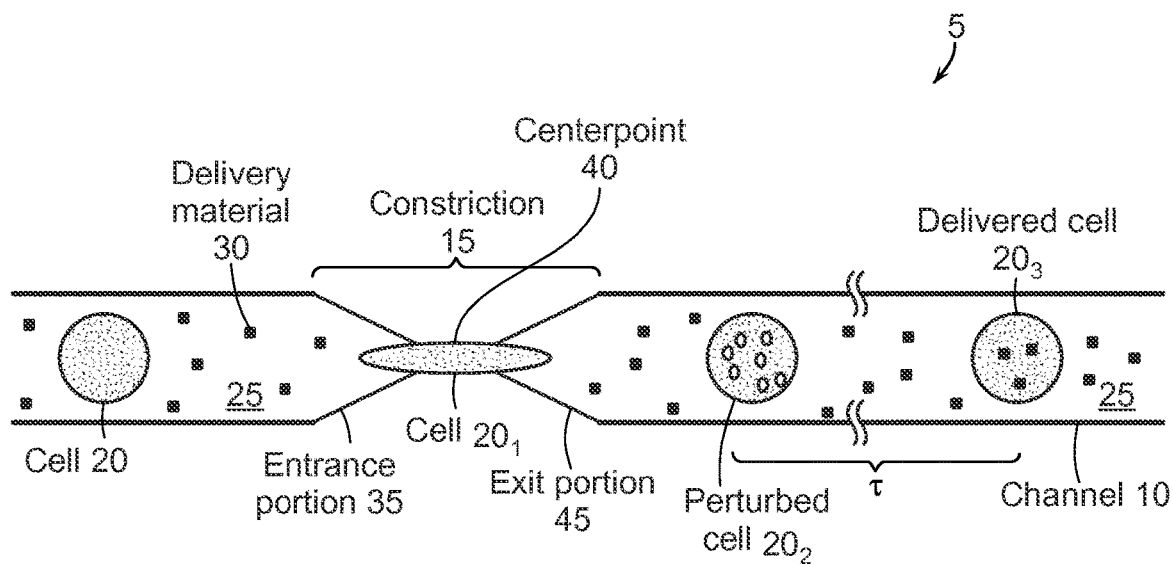
FIG. 1b is a schematic diagram of a microfluidic system. Cells are exposed to the delivery material (payload) throughout the process by suspending the cells in a solution that includes the delivery material (payload) (e.g., the cells are exposed to the delivery material before and after passing through the constriction).
Figure 2A:
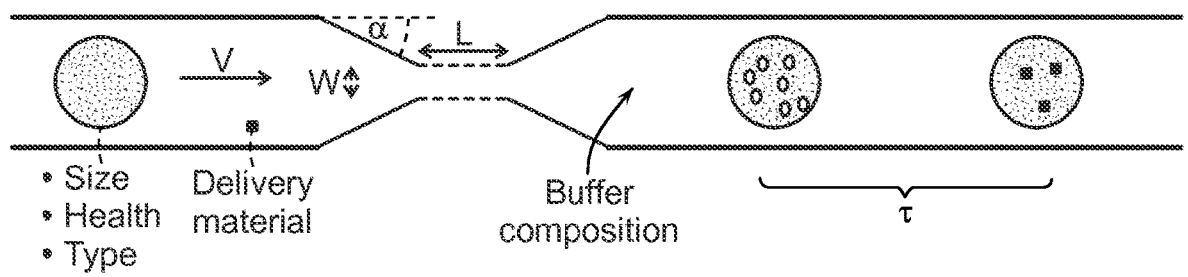
FIG. 2A is a schematic diagram of an embodiment of a microfluidic system.
Figure 2B:
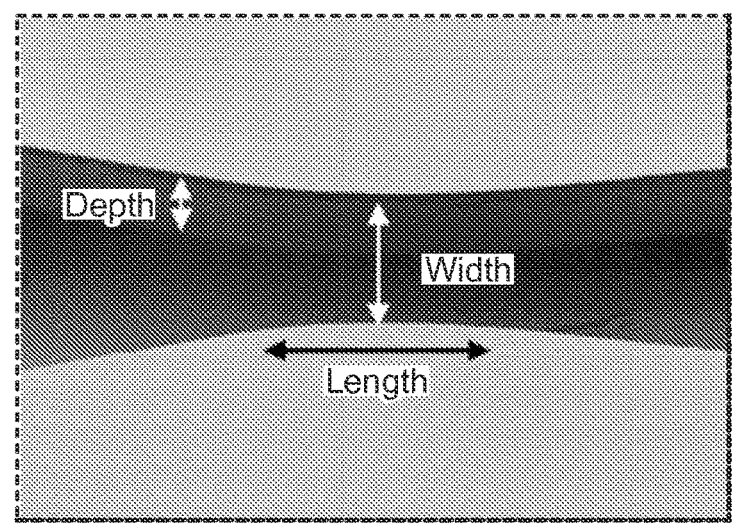
FIG. 2B is an illustration diagram of a microfluidic system depicting depth, width, and length.
Figure 3:
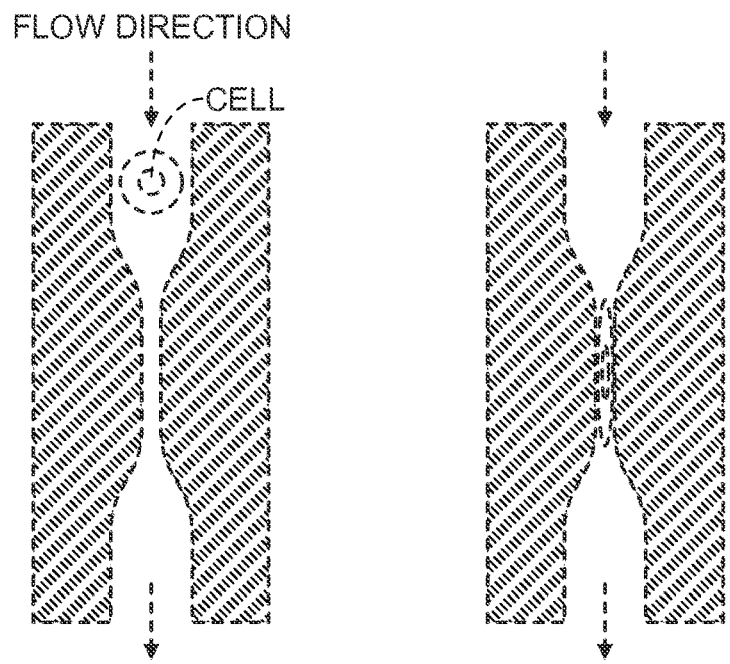
FIG. 3 is a schematic diagram of a microfluidic system.
Figure 4:
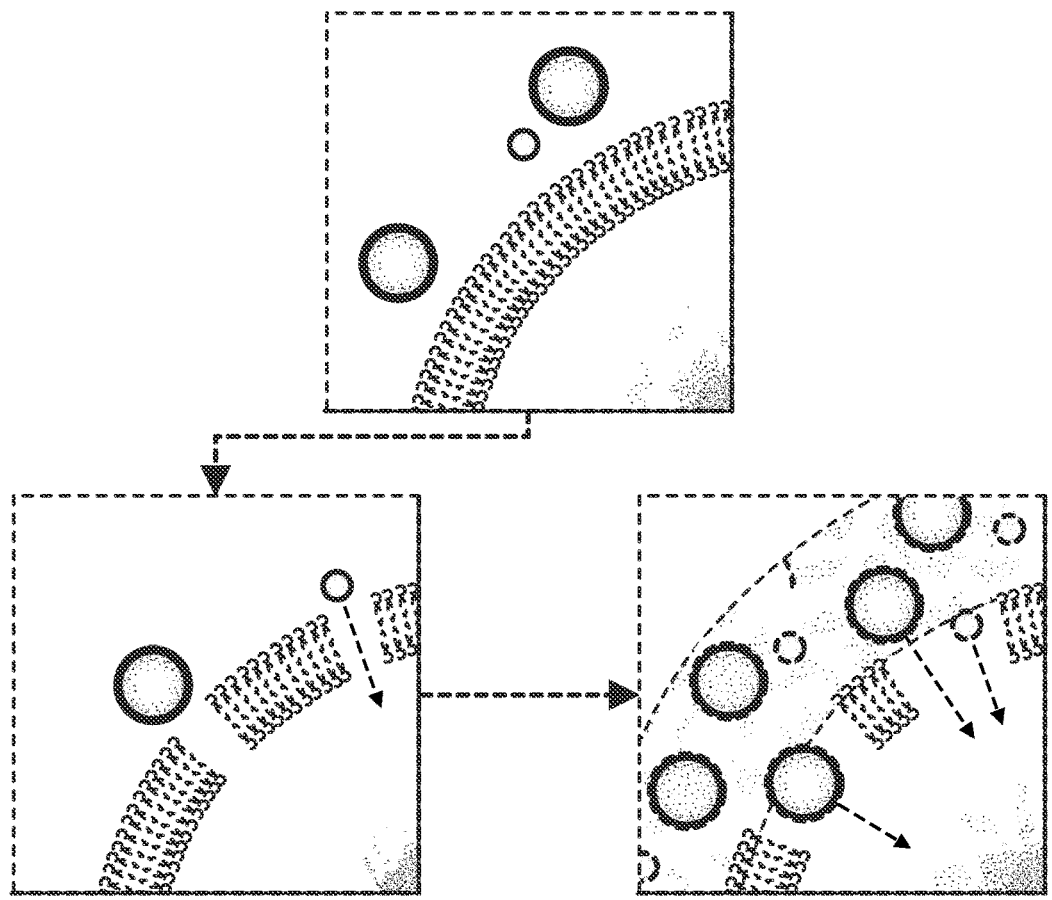
FIG. 4 is a schematic diagram showing perturbations in a cell wall.

Referring to FIGS. 1-3, a microfluidic system 5 includes a channel 10 defining a tubular lumen. The microfluidic channel 10 includes a constriction 15 that is preferably configured such that only a single target cell 20 can pass through the constriction 15 at one time. Preferably, the cells 20 pass through the channel 10 suspended in a solution buffer 25 that also includes delivery materials 30, although the delivery materials can be added to the solution buffer 25 after the cells 20 pass through the constriction 15. As the cell 20 approaches and passes through the constriction 15, the constriction 15 applies pressure (e.g., mechanical compression) to the cell 20, squeezing the cell 20 (e.g., shown as cell $20_1$). The pressure applied to the cell by the constriction 15 causes perturbations (e.g., holes shown in FIG. 4) in the cell membrane (e.g., cell $20_2$). Once the cell passes through the constriction 15, the cell 20 begins to uptake the material in the solution buffer 25 through the holes, including the delivery material 30 (e.g., cell $20_3$). The cell membrane recovers over time, and at least a portion of the delivery material 30 preferably remains trapped inside the cell.

The configuration of the constriction 15 can be customized to control the constriction of the cell 20, thereby controlling the pressure applied to the cell 20. Preferably, the constriction 15 includes an entrance portion 35, a centerpoint 40, and exit portion 45. For example, the diameter(s) of the constriction 15 can be varied to adjust the pressure applied to the cell (and how quickly that pressure is applied/released), and the length of the constriction 15 can be varied to adjust the amount of time pressure is applied to the cell. In certain configurations, physical constriction of the cell is not required, rather very briefly subjecting the cell to an unusually high sheer rate and/or compression rate may cause the desired perturbations. Generally, there is no requirement relating to the outside diameter of the microfluidic system and the ratio of the inner diameter to the outer diameter can be varied (e.g., greater than 5).

The diameter of the centerpoint 40 can be a function of the diameter of the cell 20. Preferably, the centerpoint 40 is on the same order as or smaller than the diameter of the cell 20 (e.g., 20-99% of the diameter of the cell). Preferably, the diameter of the centerpoint 40 is between 60% and 70% of the diameter of the cell, although optimal centerpoint diameter can vary based on the application and/or cell type. Exemplary diameters of the centerpoint 40 that has been used in prior experiments is 5-6 μm, and 7-8 μm. The centerpoint 40 can also be larger than the diameter of the cell 20, but be configured to cause a pulse of pressure (e.g., shearing) that is applied to the cell 20. Such pressure can be applied to the cell 20 without it touching the walls of the channel 10. Shear can be measured by known techniques (e.g, Journal of Applied Physics 27, 1097 (1956); Murphey et al.).

The constriction angle (e.g., α in FIG. 2A) of the entrance portion 35 can vary (e.g., how quickly the diameter decreases). The constriction angle is preferably an angle that minimizes clogging of the system 5 while cells are passing therethrough. The angle of the exit portion 45 can vary as well. For example, the angle of the exit portion 45 is configured to reduce the likelihood of turbulence/eddies that can result in non-laminar flow (e.g., a range from 1-80 degrees). The walls of the entrance portion 35 and/or the exit portion 45 are preferably linear, although other configurations are possible (e.g., the walls can be curved).

The cross-section of the channel 10, the entrance portion 35, the centerpoint 40, and the exit portion 45 can vary. For example, the various cross-sections can be circular, elliptical, an elongated slit, square, hexagonal, triangular, etc. The length of the centerpoint 40 can also vary, and can be adjusted to vary the amount of time that pressure is applied to the cell 20 as it passes through the constriction 15. At a given flow rate, a longer constriction 15 (e.g., a longer centerpoint 40) will apply pressure to cell 20 for a longer period of time. The depth of the channel 10, the entrance portion 35, the centerpoint 40, and the exit portion 45 can vary. For example, the depth can be adjusted to provide a tighter constriction and thereby enhance delivery in a manner similar to changes in constriction width. Width and length vary between device designs and can be determined during manufacture of the device, such as by a chrome mask used in a lithography step (when the device is silicon based). Depth can be uniform throughout the channel and can be determined during manufacture of the device, such as by a deep reactive ion etching step. The depth can be, for example, 15 µm-20 µm. As used herein, device dimensions are denoted by a series of numbers indicating length, width, and number of constrictions (e.g., 30 µm-6 m×5 denotes a device with a 30 µm length, 6 µm width, and 5 constrictions).

The velocity at which the cells 20 pass through the channel 10 can also be varied to control delivery of the delivery material 30 to the cells 20. For example, adjusting the velocity of the cells 20 through the channel 10 can vary the amount of time that pressure is applied to the cells, and can vary how rapidly the pressure is applied to the cell (e.g., slowly or shockingly). The cells 20 pass through the system 5 at a rate of at least 0.1 mm/s such as 0.1 mm/s to 5 m/s, and preferably between 10 mm/s to 500 mm/s, although other speeds are possible. In some embodiments, the cells 20 can pass through the system 5 at a rate greater than 5 m/s.

The channel 10 can be fabricated from various materials such as silicon, glass, ceramics, crystalline substrates, amorphous substrates, and polymers (e.g., Poly-methyl methacrylate (PMMA), PDMS, Cyclic Olefin Copolymer (COC), etc). Fabrication is preferably clean-room based, and can use, for example dry etching, wet etching, photolithography, injection molding, laser ablation, SU-8 masks, etc. One exemplary channel 10 is approximately 40-50 µm long, having a non-constriction diameter of approximately 50 µm, having a constriction diameter of approximately 4-8 µm. Preferably, the length of the channel 10 is kept as short to avoid clogs. Other dimensions are possible.

Figure 39:
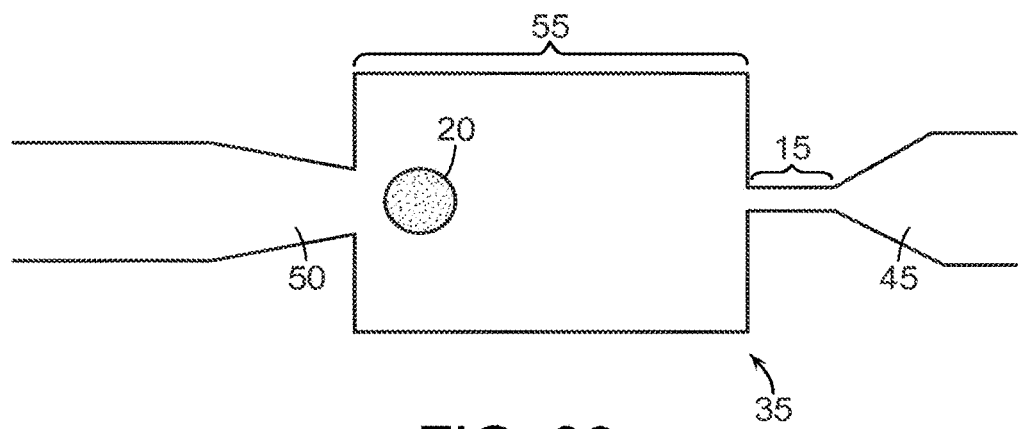
FIG. 39 depicts another embodiment of the microfluidic system wherein entrance portion has a constriction angle of 90 degrees.

FIG. 39 depicts another embodiment of the microfluidic system. In this embodiment, channel 10 includes a preliminary entrance portion 50 that does not constrict the cell 20. An expanded channel portion 55 provides for entrance portion 35 to have a constriction angle of 90 degrees (e.g., alpha in FIG. 2A).

Figure 40A:
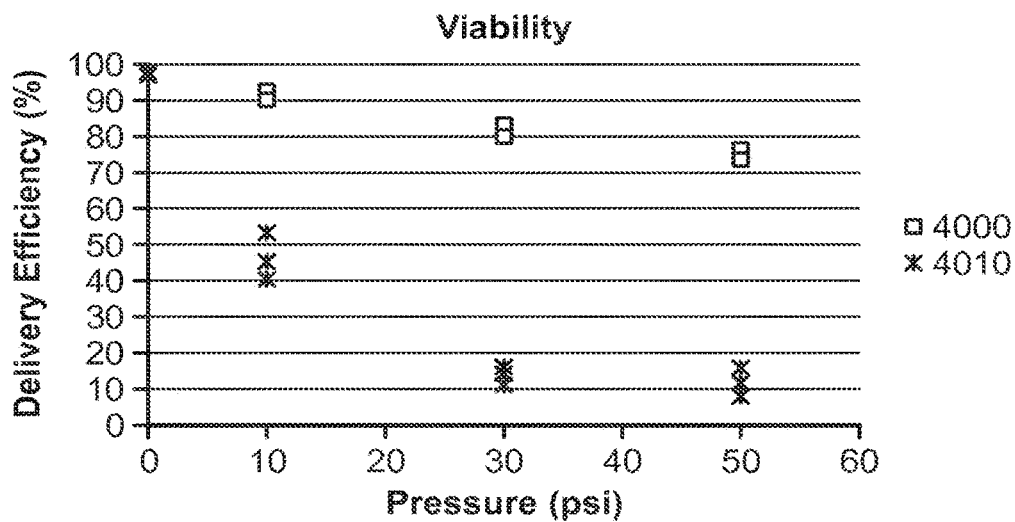
FIGS. 40A and 40B are plots showing a comparison of viability and delivery efficiency between a device in accordance with the example embodiment depicted in FIG. 2A and a device in accordance with an example embodiment depicted in FIG. 39.
Figure 40B:
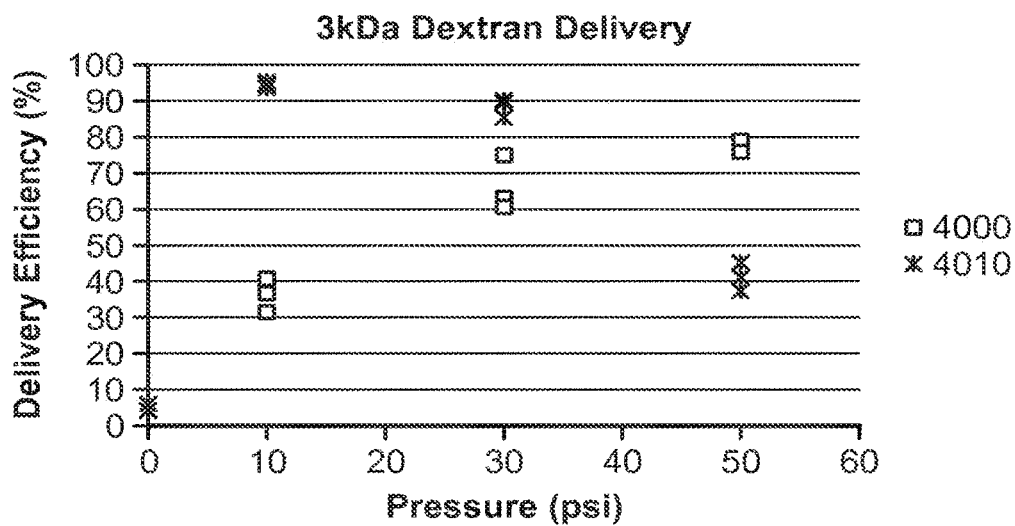

FIGS. 40A and 40B are two plots showing a comparison of viability and delivery efficiency between two example embodiments. Label 4000 designates measurements taken while using an embodiment in accordance with FIG. 2A while 4010 designates measurements taken while using an embodiment in accordance with FIG. 39. For the same cell speed and operating pressure, the embodiment of FIG. 39 has been shown to have high delivery efficiency and viability. This is despite having similar shear rates, cell speed, and time spent under compression as the embodiment of FIG. 2A.

Several parameters can influence the delivery of the delivery material 30 into the cell 20. For example, the dimensions of the constriction 15, the operating flow speeds (e.g., cell transit time to the constriction 15), concentration of the delivery material 30 in the solution buffer 25, and the amount of time that the cell 20 recovers/incubates in the solution buffer 25 after constriction can affect the absorption of the delivery material 30 into the cell 20. Additional parameters influencing the delivery of the material 30 into the cell 20 can include the velocity of the cell 20 in the constriction 15, the shear rate in the constriction 20, the velocity component that is perpendicular to flow velocity, a cell compression rate, and time in constriction. Such parameters can be designed to control delivery of the delivery material 30. The composition of the solution buffer 25 (e.g., salt concentration, serum content, etc.) can also impact delivery of the delivery material 30. As the cell 20 passes through the constriction 15, the deformation/stress induced by the constriction 15 temporarily causes injury to the cell that causes passive diffusion of material through the perturbation. In some embodiments, the cell 20 is only deformed for brief period of time, on the order of 100 µs to minimize the chance of activating apoptotic pathways through cell signaling mechanisms, although other durations are possible (e.g., ranging from nanoseconds to hours). Initial observations have indicated that absorption of the delivery material 30 by the cell 20 occurs on the order of minutes after the cell 20 passes through the constriction 15.

The cells 20 can be driven through the channel 10 by various methods. For example, pressure can be applied by a pump on the entrance side (e.g., gas cylinder, or compressor), a vacuum can be applied by a vacuum pump on the exit side, capillary action through a tube, and/or the system 5 can be gravity fed. Displacement based flow systems can also be used (e.g., syringe pump, peristaltic pump, manual syringe or pipette, pistons, etc.). Exemplary flow rates through a single channel 10 are on the order of 1 µl in a few seconds. Additionally, solution buffer 25 can include one or more lubricants (pluronics or other surfactants) that can be designed to reduce or eliminate clogging of the channel 10 and improve viability.

The system 5 can be controlled to ensure that delivery quantities of the delivery material 30 is consistent across the cell population. For example, the system 5 can include the use of a post-constriction convective delivery mechanism that impinges delivery material 30 onto the permeabalized cell membrane of the cell 20. By controlling the flow rate of the secondary stream, the quantity of delivery material 30 provided to the cell can preferably be controlled. Additionally, controlling the concentration of delivery material 30 in the solution buffer 25 during membrane recovery can also improve the consistency of delivery of the delivery material 30 to the population of cells. Preferably, the system 5 operates as a purely mechanical system without applying any electrical fields and/or chemical agents, although other configurations are possible (e.g., electrical and/or optical sensors can be used to measure cell properties such as fluorescence). Additionally, the system 5 preferably operates independent of the type of material being delivered. For example, proteins, RNA, and DNA can be delivered through the same system without any additional modifications.

In some configurations with certain types of cells 20, the cells 20 can be incubated in one or more solutions that aid in the absorption of the delivery material to the interior of the cell. For example, the cells 20 can be incubated in a depolymerization solution such as Lantrunculin A (0.1 µg/ml) for 1 hour prior to delivery to depolymerize the actin cytoskeleton. As an additional example, the cells can be incubated in 10 µM Colchicine (Sigma) for 2 hours prior to delivery to depolymerize the microtubule network. These methods can help in obtaining gene expression when delivering DNA.

Figure 5:
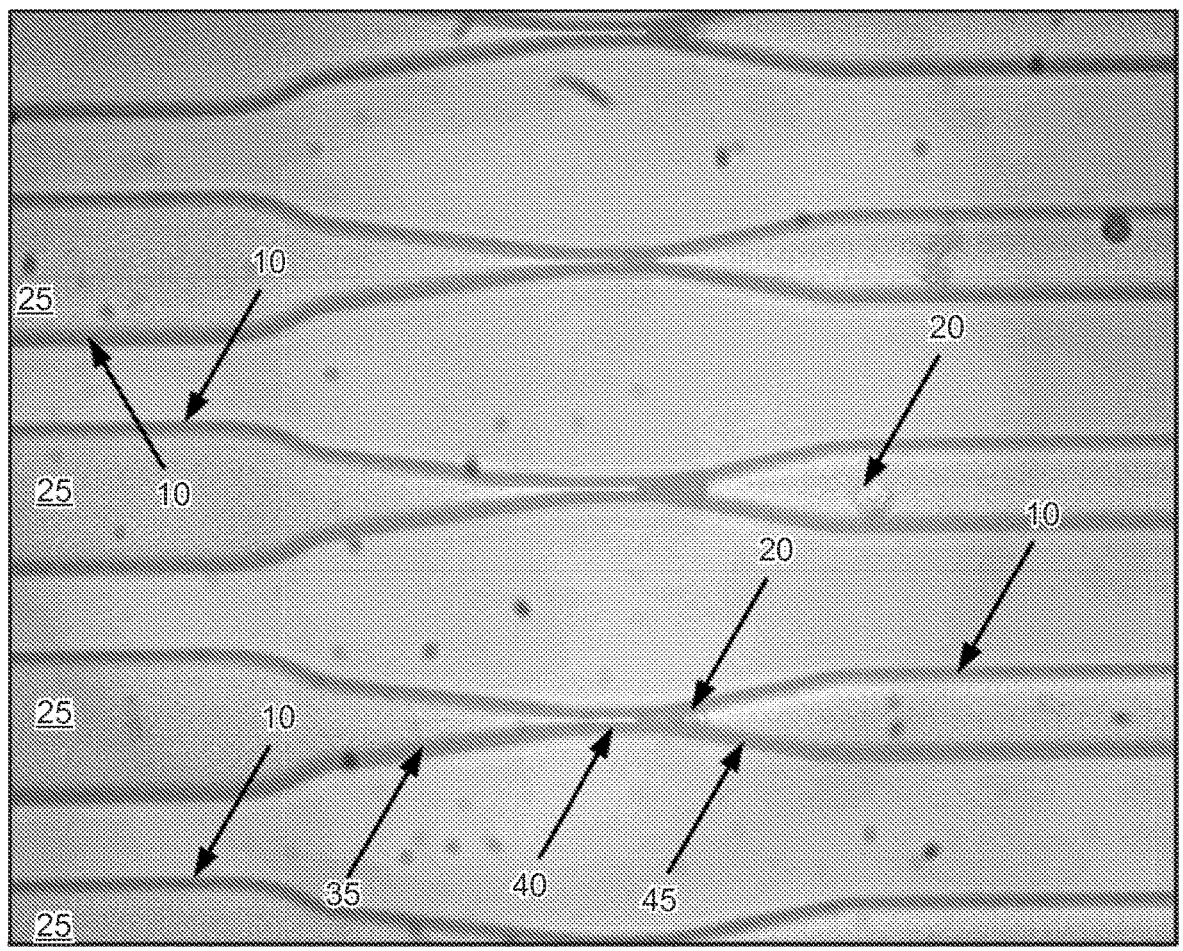
FIG. 5 is a photograph of a microfluidic system.
Figure 6:
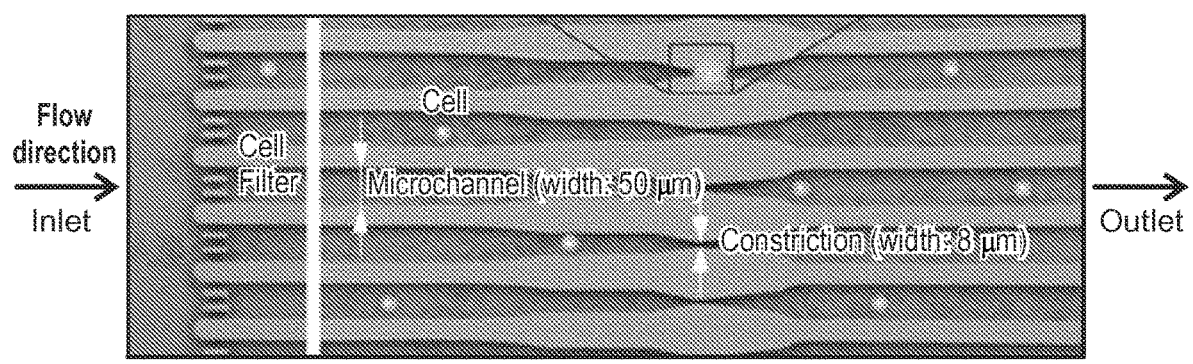
FIG. 6 is a photograph of a microfluidic system.
Figure 7:
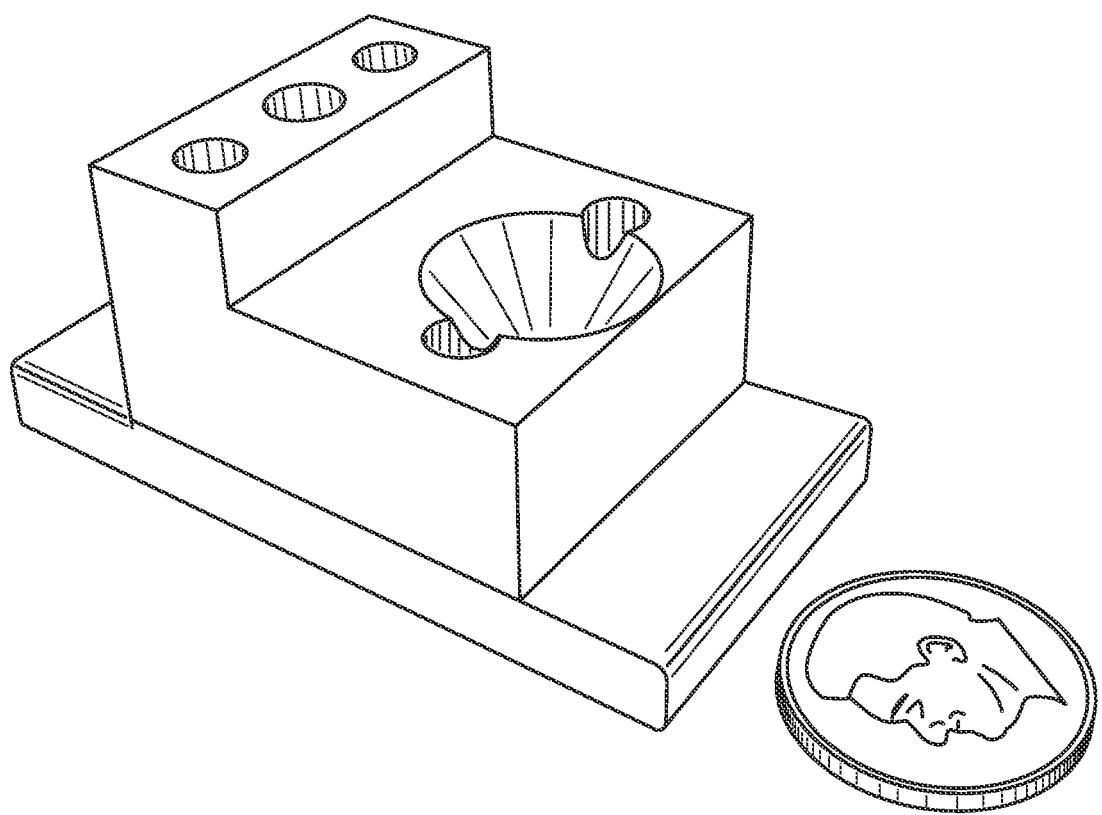
FIG. 7 is a photograph of a microfluidic system.

Referring also to FIG. 5, a photograph of a parallel configuration of the system 5 is shown. The system 5 can include any number of parallel channels. Preferably, as additional parallel channels are added to the system 5, the overall throughput of the system 5 can be increased. FIG. 6 shows a photograph of a parallel configuration of the system 5 that includes filters at the inlet of each of the channels 10. Additionally, FIG. 6 also shows a configuration of the constriction 15 that includes an entrance portion 35 that includes multiple steps. Referring also to FIG. 7, an additional photograph of a prototype of the system 5 is shown. As evident in FIG. 7, the prototype, including incubation well, has dimensions of approximately 1 inch×¼ inch×¼ inch. Other configurations of the system 5 can also include sorters, pretreatment/post treatment modules, and/or sensor modules (e.g., optical, electrical, and magnetic).

Figure 42:
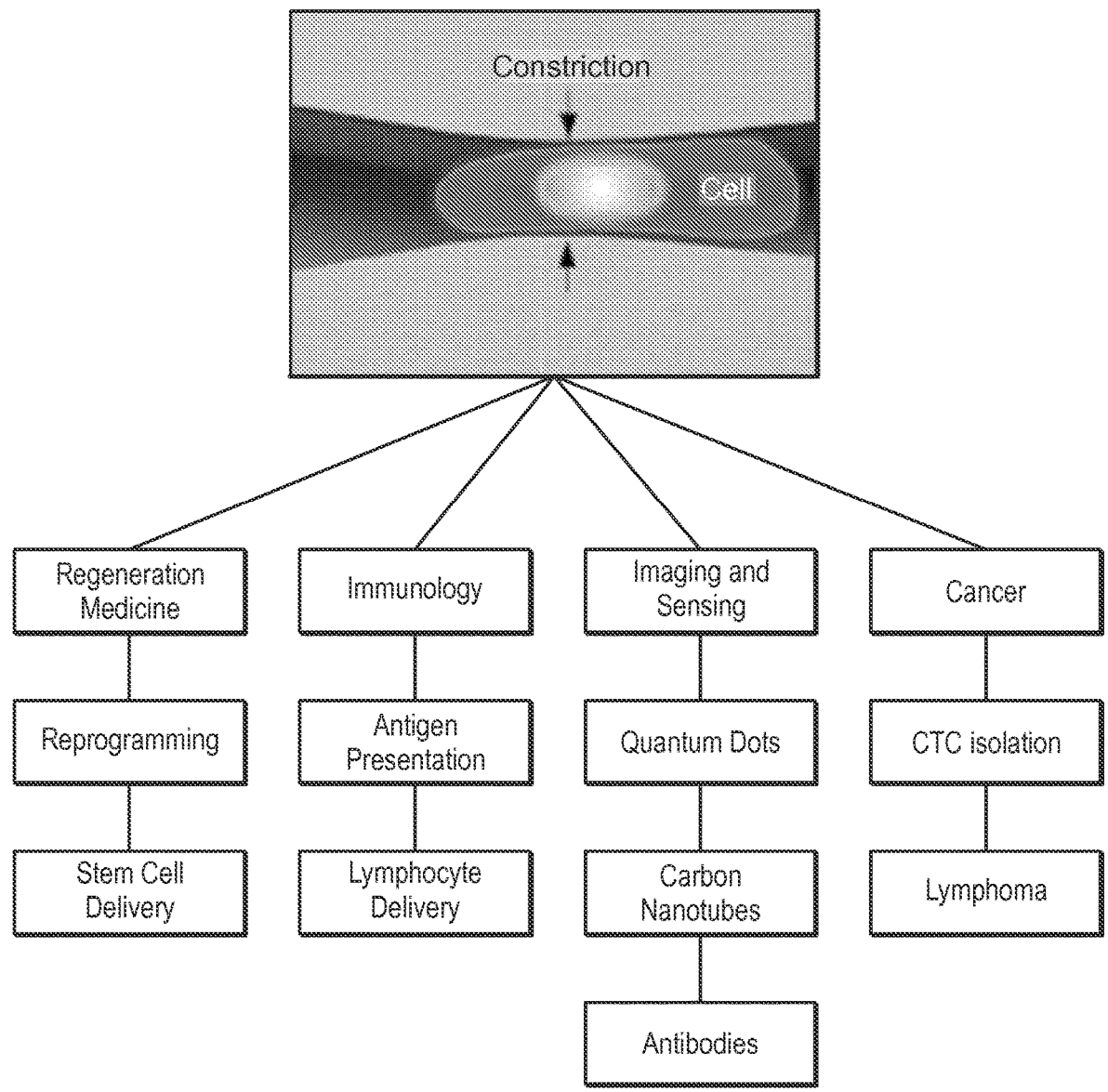
FIG. 42 is an illustration depicting several example fields of application such as regenerative medicine; immunology; imaging and sensing; and cancer vaccines and cancer research.

As described in more detail below with regard to the examples, the microfluidic system and related methods have a broad range of applications. FIG. 42 is an illustration depicting several example fields of application. For example, the current subject matter can be applied to regenerative medicine such as to enable cell reprogramming and stem cell differentiation. The current subject matter can be applied to immunology such as for antigen presentation and enhancement/suppression of immune activity through delivery to dendritic cells, monocytes, T cells, B cells and other lymphocytes. Further, imaging and sensing can benefit from improved delivery to target cells of quantum dots, carbon nanotubes and antibodies. Additionally, the current subject matter has application in cancer vaccines and research, such as for circulating tumor cell (CTC) isolation and Lymphoma treatment. The method also provides a robust platform to screen for active siRNA and small molecule compounds capable of treating a disease or manipulating cell behavior.

This concept has been successfully demonstrated in a prototype where the cells 20 were induced to take-up otherwise membrane-impermeable dye (e.g., fluorescent dyes from 3 kDA to 2 MDA in molecular mass, DNA, protein, RNA, nanotubes or nanoparticles present in the solution buffer 25. The cells 20 have been shown to recover and proliferate after the process while retaining the delivered material for over 72 hours. Eleven different cell types have been tested with this system, including those listed in FIG. 33, hence demonstrating that the system provides robust performance in different cell types. FIG. 33 is a table including cell types which the current subject matter has successfully been applied. Average cell throughput has been measured on the order of 5,000-20,000 cells/second, average delivery efficiency has been measured at 96%, and cell viability has been measured at 95% using a single channel 10. All tests were performed at room temperature. Temperature, however, may be varied in some techniques. For example, the methods can be carried out at room temperature (e.g., 20° C.), physiological temperature (e.g., 39° C.), higher than physiological temperature, or reduced temperature (e.g., 4° C.), or temperatures between these exemplary temperatures. Performing the methods at a reduced temperature (i.e. substantially near 4° C. which can be achieved, for example, by using refrigeration, ice bath, or other known techniques), has produced a surprising improvement in delivery efficiency and cell viability. Thus, the temperature can be adjusted to affect composition delivery and cell viability.

Figure 8A:
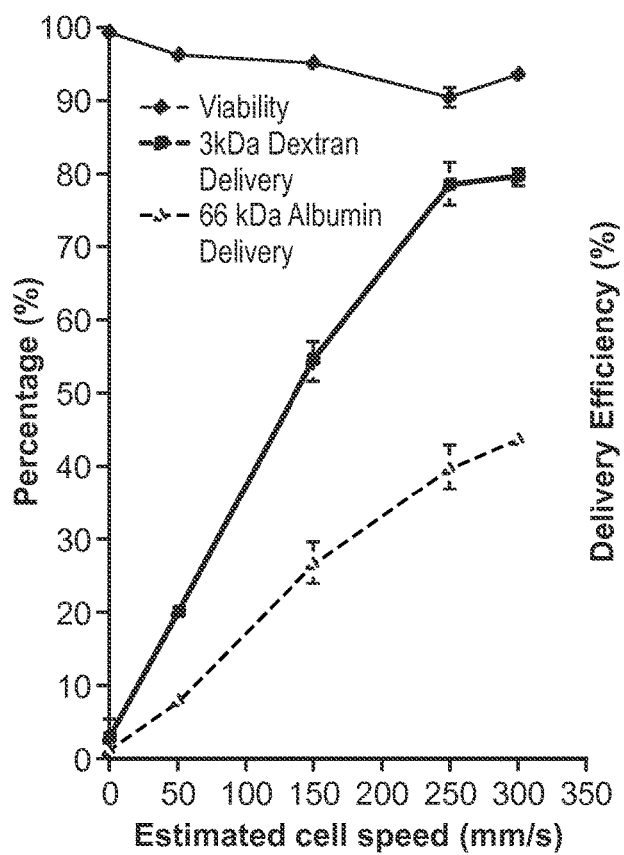
FIGS. 8a-8b are graphs showing exemplary results obtained from a microfluidic system.
Figure 8B:
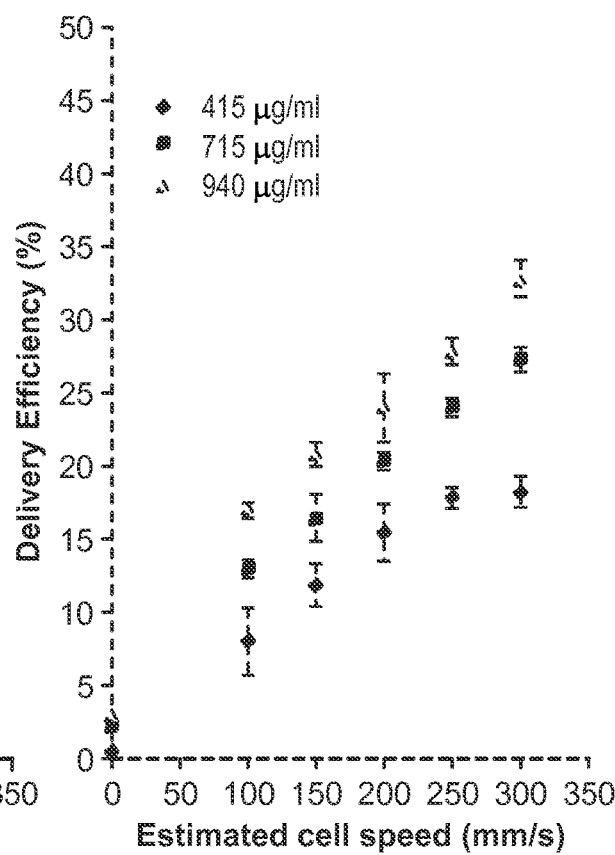

As shown in FIGS. 8a-b, increasing the cell speed through the constriction 15 can increase the delivery percentage and delivery efficiency of the delivery material 30. It was found that delivery efficiency varies linearly with cell speed, and that there was a dosage dependent response.

Figure 9:
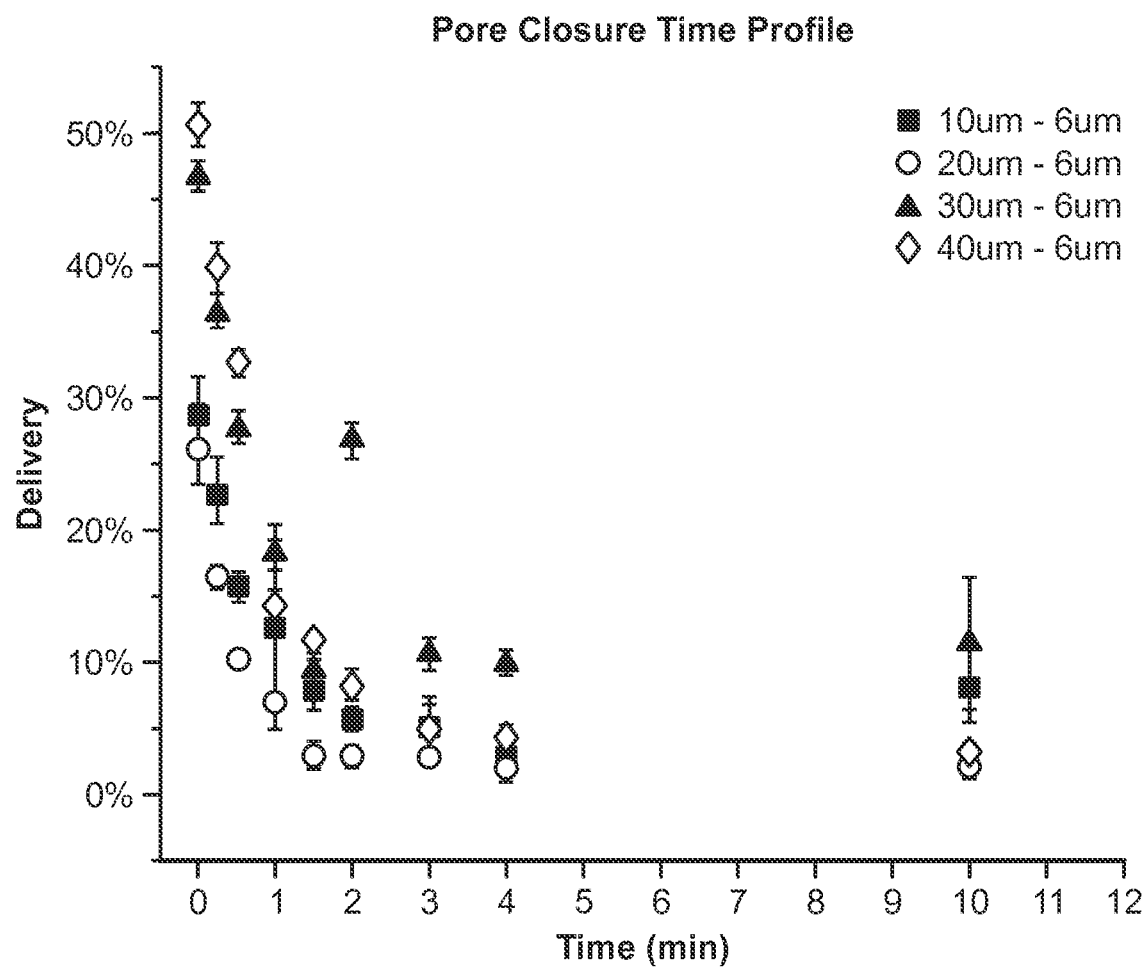
FIG. 9 is a graph showing exemplary results obtained from cells that were processed using a microfluidic system.

As shown in FIG. 9, the incubation time of a cell in the solution buffer 25 after the cell passes to the constriction 15 can have an effect on the overall delivery percentage of the delivery material 30 to the cell 20. It was noted, however, that after a certain amount of incubation time (approximately 2-3 minutes), the delivery percentage was substantially unchanged. Based upon this data, it is believed that the perturbations caused in the cell 20 after it passes through the constriction 15 are corrected within on the order of about five minutes after the cell 20 passes to the constriction 15. Additionally, and for reference, −1 minute corresponds to the control group.

Figures 10, 11:
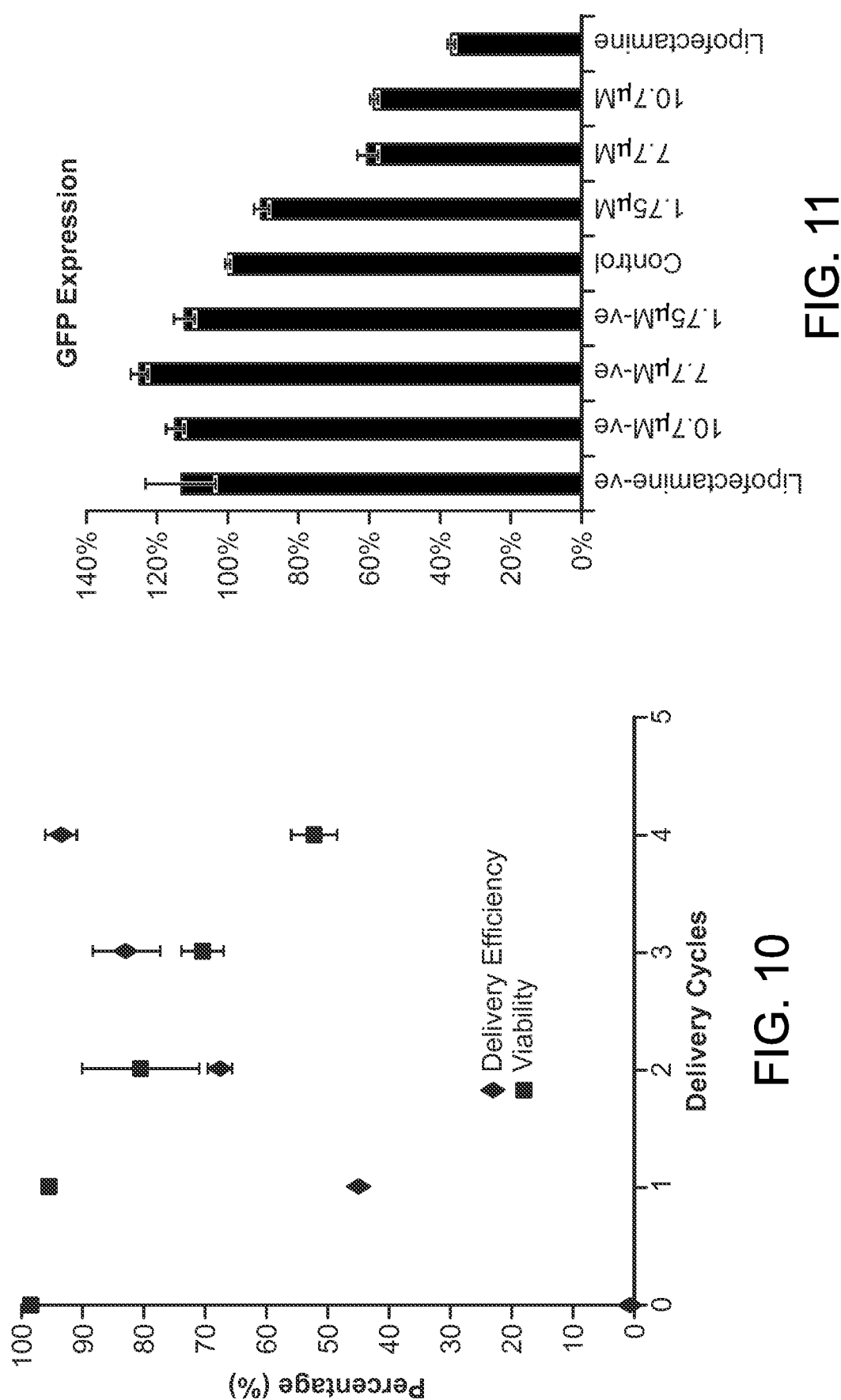
FIG. 10 is a graph showing exemplary results obtained from cells that were processed using a microfluidic system.
FIG. 11 is a graph showing exemplary results obtained from cells that were processed using a microfluidic system.

As shown in FIG. 10, it was observed that passing the cells 20 through the constriction 15 multiple times can have an effect on the overall delivery percentage, but that it negatively affected the overall viability of the cells 20. To generate this data, cells were passed through the constriction 15, collected, and passed through the device again within approximately 1 minute.

It has been observed that during the time the cells 20 are perturbed (e.g., after passing through the constriction 15) that material from within the cell can be extracted through the perturbations. Thus, it has been found that when the cells 20 are perturbed, that material can flow in and out of the cell 20. This property means that the system 5 can be used as a method of sampling intracellular material without lysing the cell. The perturbations in the cell membrane will preferably result in an outflow of macromolecules from the cytoplasm and, thus, can be used to probe the composition of the cytoplasm.

As shown in FIG. 11, stable green florescent protein (GFP) expressing HeLa cells were treated in the presence of GFP silencing siRNA (Ambion, U.S.A) and analyzed by FACS (FACS Canto II, BD Biosciences, U.S.A.) at 48 hours for fluorescence knockdown. The results in FIG. 11 indicate a >40% knockdown of gene expression—a result comparable to that of commercial reagents such as Lipofectamine 2000 (Invitrogen, U.S.A). Scrambled siRNA controls, also in FIG. 11, indicate that this knockdown is not caused by the deformation process itself.

Figure 14:
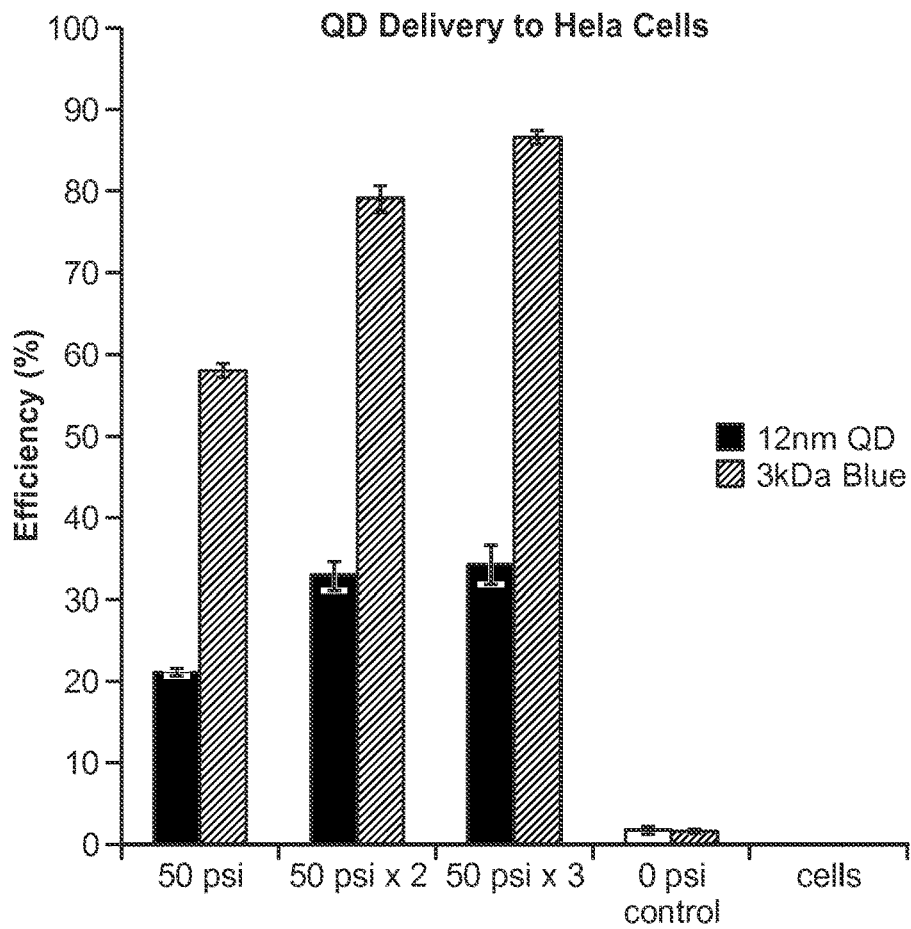
FIG. 14 is a graph showing exemplary results obtained from cells that were processed using a microfluidic system.
Figure 15:
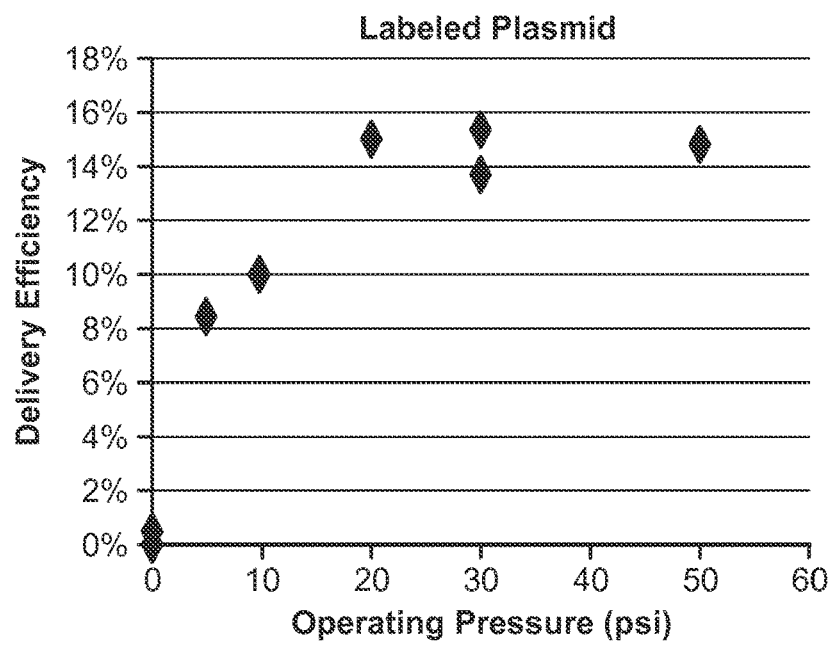
FIG. 15 is a graph showing exemplary results obtained from cells that were processed using a microfluidic system.
Figure 18A:
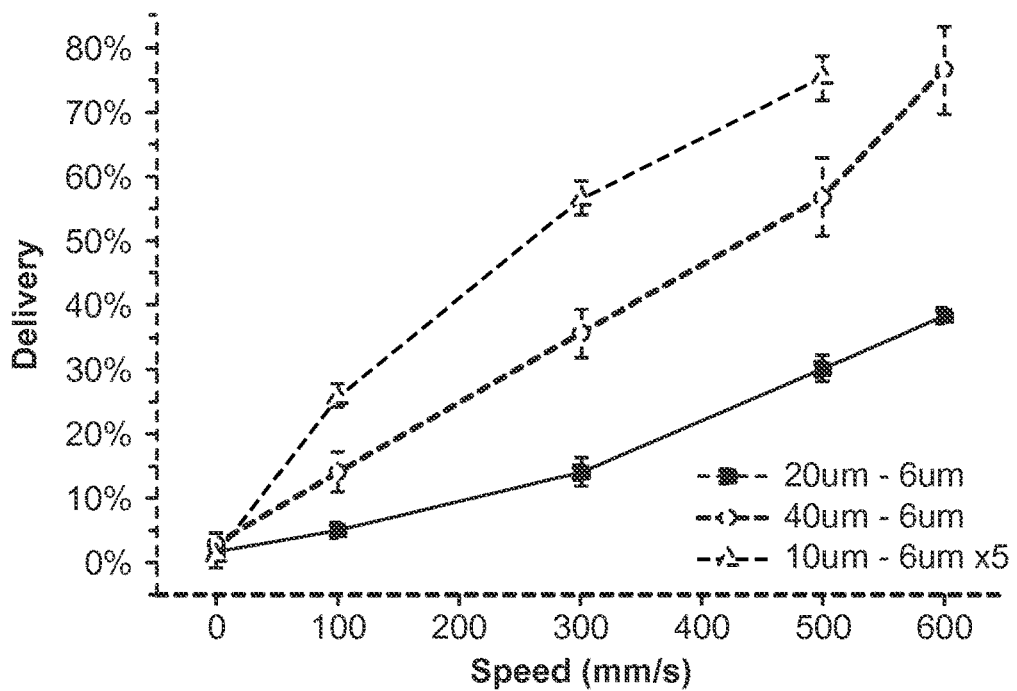
FIGS. 18a-18b are graphs showing exemplary results obtained from cells that were processed using a microfluidic system.
Figure 18B:
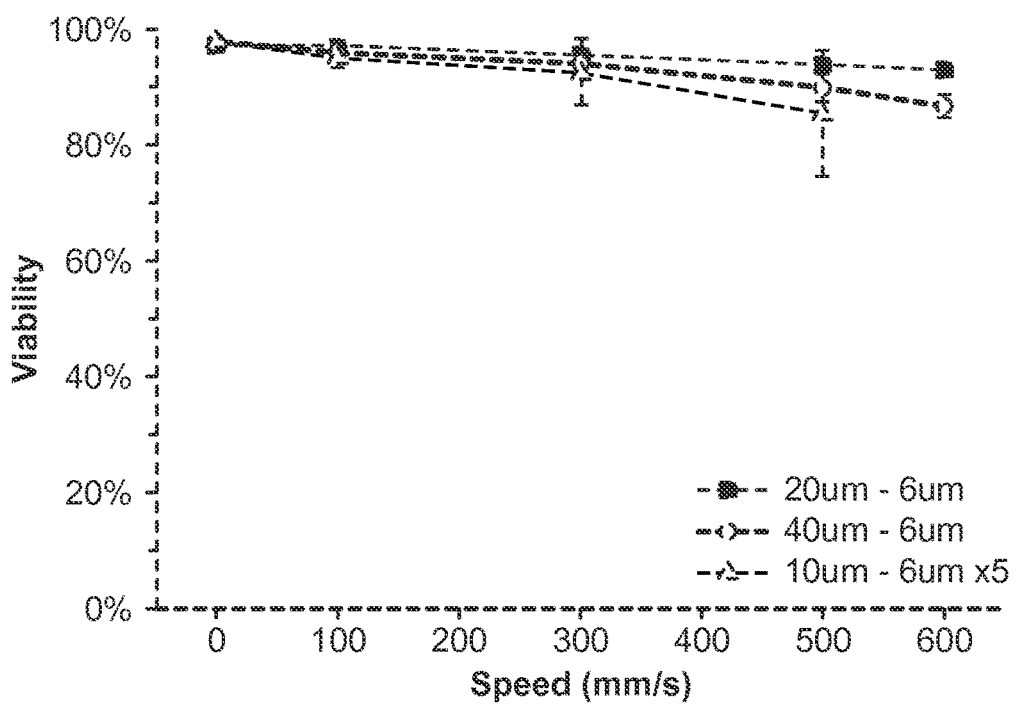

As shown in FIGS. 13-14 and, the squeeze dimensions can have an effect on the overall delivery efficiency of the delivery material 30. For example, FIGS. 13-14 show that as the operating pressure is varied (e.g., by varying the length and/or width of the constriction 15) the overall delivery efficiency varies somewhat (FIG. 14 relates to the delivery of quantum dots (nanopartices) under different conditions). Furthermore, as shown in FIGS. 18a-18b, the estimated cell speeds can have an effect on the overall viability and delivery efficiency of the delivery material 30. For example, FIG. 18a shows that as the operating speed is varied, the overall delivery efficiency varies somewhat. Additionally, FIG. 18b shows that as operating speed is varied, the viability of the cells can vary somewhat. These figures show that a change in constriction length can enhance delivery while minimally impacting viability. Additionally, larger molecules enter the cell at a lower rate after constriction than smaller molecules. This intracellular delivery method described herein is "universal" in that it works for many different type of materials and cells. Further, the membrane disruptions induced by this device can be typically at least ~100 nm in size, although other size disruptions are possible.

Figure 12:
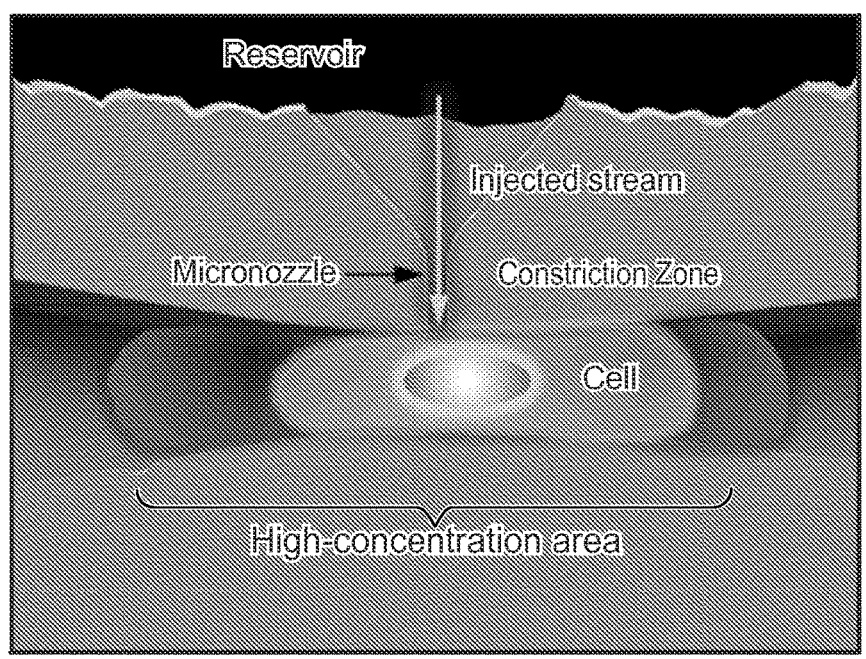
FIG. 12 is a schematic diagram of a microfluidic system.

Referring to FIG. 12, in one implementation, the concentration gradient between the solution buffer 25 and the cytosol can be controlled to predictably control the amount of delivered material. Localized delivery methods that expose the cells 20 to a concentrated cloud of macromolecules after the cells 20 have been porated by the constriction can be used. Any such localized delivery method, however, should account for the estimated perturbation resealing time to ensure proper function. This can be implemented by incorporating a "micronozzle" perpendicular to the channel that delivers a high concentration of the payload to the vicinity of the cell membrane (illustrated in FIG. 6A). Preferably, the micronozzle can be located at and/or near the constriction 15. Such an approach could allow supplementation of the diffusive delivery mechanism with a convective component thus enabling more precise cell loading with higher concentrations. Preferably, the injection takes place while the cell 20 is in a high concentration area of the constriction 15. A localized technique has the added advantage of conserving valuable delivery materials because it is then not necessary to maintain a high concentration throughout the buffer.

Referring to FIG. 16a, a series of micropillars 100 can be used to apply pressure to the cells 20 such that a perturbation is caused. In this implementation, the cells 20 are forced through a constricting pillar array in such a manner that pressure is applied to the cells 20.

Referring to FIG. 16b, compression plates 105 can be used to apply pressure to the cells 20 such that a perturbation is caused. In this implementation, the compression plates 105 can be controlled such that pressure is applied to the cells 20 for a predefined amount time. The compression plates 105 can be configured such that one or both plates move to apply pressure to the cells 20. An additional sets of compression plates 105 can also be supplied such that the cells 20 are substantially surrounded.

Referring to FIG. 16c, buffer additives 115 (or bulking materials bound to the cell surface) can be used to simulate squeezing as the cell 20 passes through a constriction 15 that is larger than the diameter of the cell 20. For example, simulated constriction due to interference by the buffer additives 115 is possible. Examples of buffer additives 115 include micro or nanoparticles (e.g., polymer based, lipid based, ceramic based, metallic, etc.). These particles are labeled with a cell binding ligand such as an antibody, DNA sequence, peptide or small molecule, although this is not required.

Referring to FIG. 16d, beads 120 can be used to compress the cell 20. For example, magnetic and/or electrostatic force can be used to apply pressure to the cell 20, or in the case of FIG. 16e, to pull the cell 20. Preferably, the force applied to the cell 20 is sufficient to cause a perturbation.

Referring to FIG. 16f, multiple fluid streams 125 can be directed in such a manner that compression (or rapid transitory shearing) of the cell 20 is caused. For example, the multiple fluid streams 125 can be fired in such a manner as that they approach or impinge upon one another. As the cells 20 pass through the multiple fluid streams 125, force can be applied to the cells 20 such that a perturbation in the membrane of the cell 20 is caused. Alternatively, cells can be fired through a narrow slit-like nozzle to facilitate delivery.

The system 5 can be a standalone system, such as that shown in FIG. 7, although other configurations are possible. For example, the system 5 can be implanted in vivo in a patient for local intracellular delivery, and or be incorporated ex vivo in a machine for treatment of cells before returning the cells to the patient.

In addition to its delivery advantages described herein, the microfluidic nature of the system enables one to exercise precise control over delivery conditions, pretreatment and subsequent characterization of cells. For example, the system may be implemented in series with a Fluorescence Activated Cell Sorting (FACS) module. This can enable the delivery and sorting of the desired cells on the same system, in real-time. Various pretreatment and post-sort assaying techniques can also be deployed, thus enabling the development of continuous, high-throughput assays for drug screening and diagnostics.

Figure 43A:
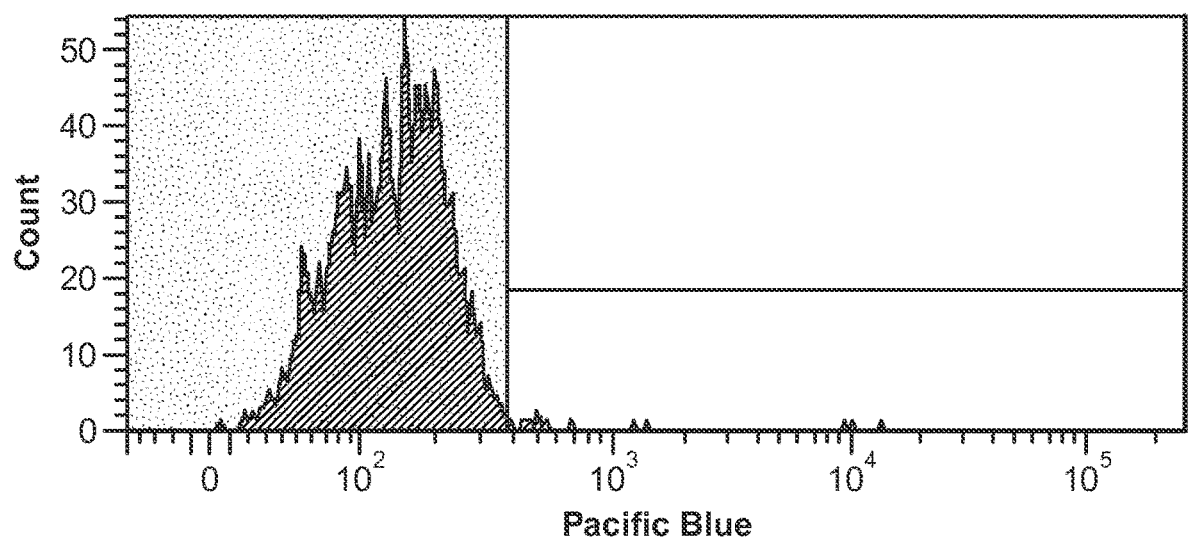
FIGS. 43A and 43B are intensity histograms from flow cytometry of a control population that is exposed to cascade blue conjugated 3 kDa dextran and a population of cells that have been subjected to a 30 μm-6 μm device and then exposed to the 3 kDa dextran.
Figure 43B:
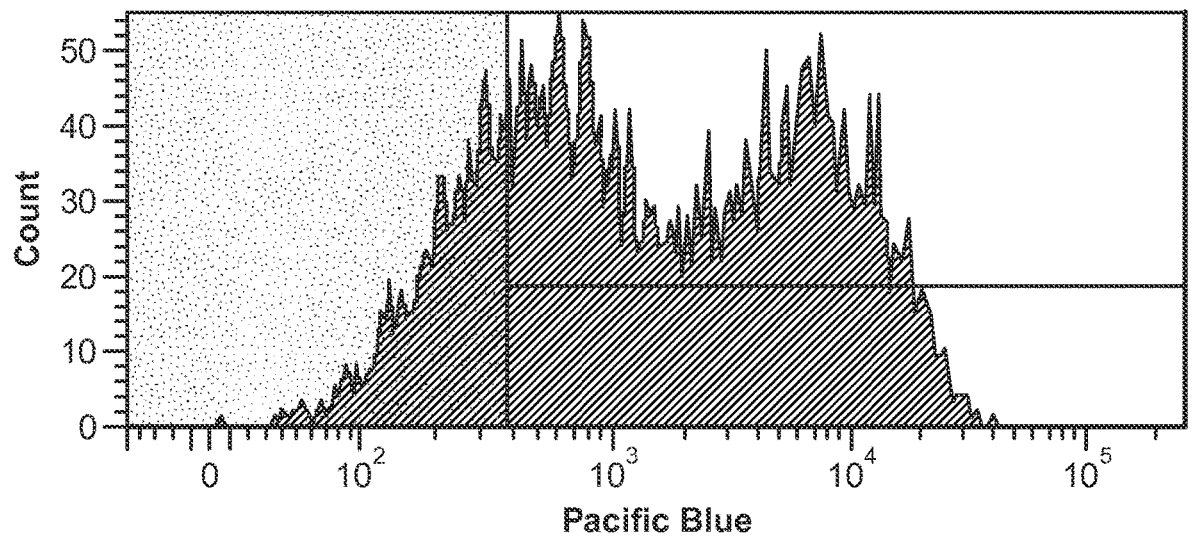

The delivery efficiency of a payload delivered to target cells is determined by subjecting a control population of target cells to a payload as well as a population having undergone treatment by a microfluidic device. The control sample is exposed to the same delivery solution, at the same concentration, for at least the same amount of time as the cells treated by the device. To compensate for surface binding, endocytosis, and other effects such as autoflourescence, a delivered region is defined such that only the top 1-5% of live control cells fall into this region. The delivery efficiency of a sample thus corresponds to the percentage of live cells that are in the delivered region. For example, FIG. 43A is an intensity histogram from flow cytometry of a control population that is exposed to cascade blue conjugated 3 kDa dextran. FIG. 43B is an intensity histogram from flow cytometry of cells that have been subjected to a 30 µm-6 µm device. The defined delivered region is the unshaded region in both 43A and 43B.

Figure 17:
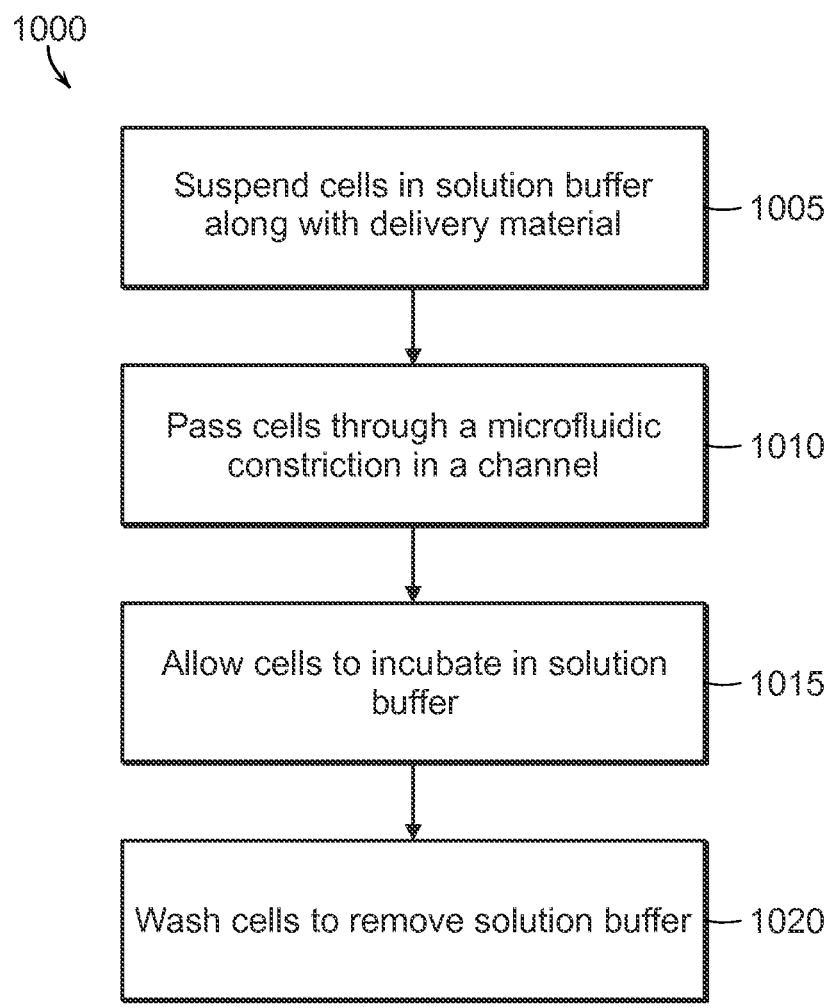
FIG. 17 is a flow diagram relating to a method of using a microfluidic system.

In operation, referring to FIG. 17, with further reference to FIGS. 1-3, a process 1000 for performing intracellular delivery the system 5 includes the stages shown. The process 1000, however, is exemplary only and not limiting. The process 1000 may be altered, e.g., by having stages added, removed, altered, or rearranged.

At stage 1005, the cells 20 are suspended solution buffer 25 along with delivery materials 30. Typical cell concentrations can range from $10^4$ to $10^9$ cells/ml. Delivery material concentrations can range from 10 mg/ml to 0.1 ug/ml. The delivery material may be added to the cell buffer before or immediately after delivery depending on the desired setup given that the injuries/pores remain open for 1-5 minutes. The solution buffers may be composed of a number of salts, sugars, growth factors, animal derived products or any other component necessary for proper cell proliferation, maintaining cell health or induction of cell signaling pathways. Additional materials may also be added to the solution buffer 25. For example, surfactants (e.g., pluronics) and/or bulking materials can be added to the solution buffer 25.

At stage 1010, the solution buffer 25 including the cells 20 and the delivery materials 30 are passed through the channel 10 of the system 5. The solution buffer 25 can pass through the channel 10 using gravity, or can be assisted by other methods. For example, pressure can be applied to the solution buffer 25 on the entrance side of the channel 10 (e.g., using a gas cylinder and/or compressor), and/or a vacuum can be applied by a vacuum pump on the exit side. Additionally, displacement based flow systems can also be used.

As the individual cells 20 pass through the constriction 15, a pressure is momentarily applied to the cell 20 by the solid construction of the constriction 15 causing perturbations such as holes to develop in the cell membrane such that the delivery materials 30 can be delivered to the inside of the cell 20. The amount and/or duration of the pressure applied to the cell 20 can be varied by adjusting the dimensions of the constriction 15, the velocity at which the cell 20 passes through the constriction 15, and/or by adjusting the shape of the constriction 15. In one configuration, approximately 5,000-20,000 cells/second pass through the constriction 15, and each cell is constricted for approximately 100 µs.

The system 5 can include one or more of the channels 10. For example, the system 5 can include 50-100 of the channels 10 that are arranged in a parallel configuration. Using a parallel configuration can reduce the consequences of a clog developing in one or more of the channels 10, and can increase the overall throughput of the system 5. Additionally, the system 5 can include one or more of the channels in series with one another.

At stage 1015, after the cells 20 pass through the constriction 15, the cells are allowed to incubate/recover by sitting in the solution buffer 25. During this time, the cells 20 will intake some of the delivery materials 30 is present in the solution buffer 25 through the perturbations in the cell membrane. One mechanism of intake is diffusion-based, because larger molecules appear to be absorbed at a slower rate than smaller molecules. Preferably, the cells 20 are allowed to incubate/recover in the solution buffer 25 for on the order of 2-5 minutes, although other durations are possible. During the time that the cells 20 are incubating/recovering in the solution buffer 25, material from inside the cell 20 may also release from the cell into the solution buffer 25. During the incubation/recovery period, certain conditions can be controlled to ensure that delivery quantities of the delivery materials 30 are consistent across the cell population. For example, post-constriction, convective delivery mechanisms that impinge delivery material onto the incubating/recovering cell can be used.

Optionally, at stage 1020, after the cells have incubated/recovered, the cells can be washed to remove the solution buffer. Preferably, the washing occurs after the time period required for the perturbations to be repaired, although the washing can occur at other times in order to control the amount of delivery materials 30 absorbed by the cells.

Example 1—Delivery of Functional Engineered Nanoparticles

Engineered nanomaterials have immense potential as live cell imaging tools, therapeutic molecular delivery agents, or even as ways to manipulate live cells with external handles such as light or magnetic fields. (Howarth, M., et al. Monovalent, reduced-size quantum dots for imaging receptors on living cells. Nature Methods 5, 397-399 (2008)). However, much of these potential applications require that nanomaterials be delivered into the cell cytosol. Most nanoparticles, such as QDs, need to be passivated with a polymer that renders the nanoparticles soluble in aqueous media, and this generally prevents them from passively diffusing across the cell membrane. Microinjection of nanoparticles is considered impractical due to specialized equipment requirement and low throughput while electroporation causes QD aggregation inside the cell. Therefore, most attempts to deliver QDs into the cell cytoplasm have relied on QDs being endocytosed by the cell and escaping from the endosome. Prior to the current subject matter, it was not possible to deliver QDs into cell cytoplasm in a satisfactory and scalable manner. They system provides a solution to this delivery problem of earlier approaches.

The microfluidic device is combined with a new generation of recently described biologically compatible QDs. (Liu, W., et al. Compact biocompatible quantum dots via RAFT-mediated synthesis of imidazole-based random copolymer ligand. JACS 132, 472-483 (2010)). The QDs used throughout example 1 were coated with a poly-imidazole ligand comprised of multiple metal-chelating imidazole groups and multiple water-solubilizing, passivating poly (ethylene) glycol (PEG).

For cytosolic delivery of QDs, cells were aliquoted into a PBS solution containing QD. The cell-QD solution was pipetted into the microfluidic device and the solution was driven through the channels at constant pressure, followed by a 5 min incubation period. After this incubation period, excess QDs were separated by centrifugation. For the control population, the cell-QD solution was placed in the microfluidic device and the cells were exposed to the QD solution for an amount of time equivalent to the cytosolic delivery protocol.

Figure 19:
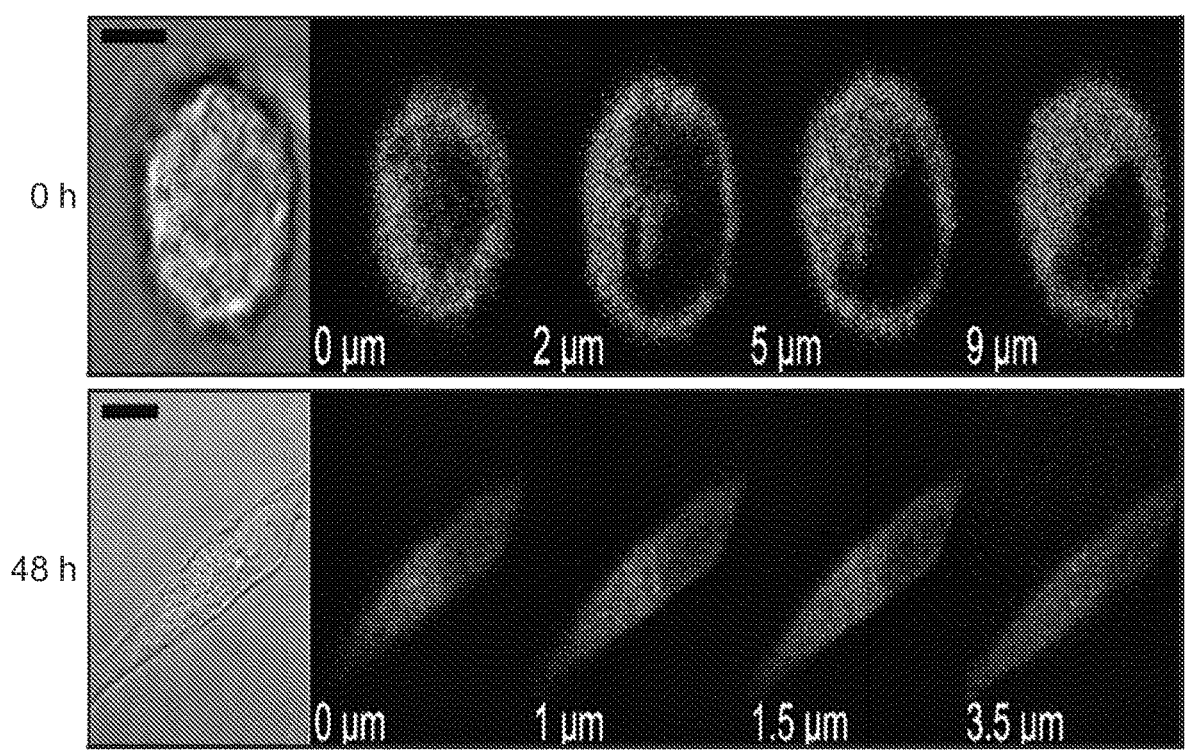
FIG. 19 is an overlay of transmission and confocal fluorescence images, followed by z-section confocal fluorescence images of treated cells delivered with quantum dots (QDs) using the current subject matter.
Figure 20A:
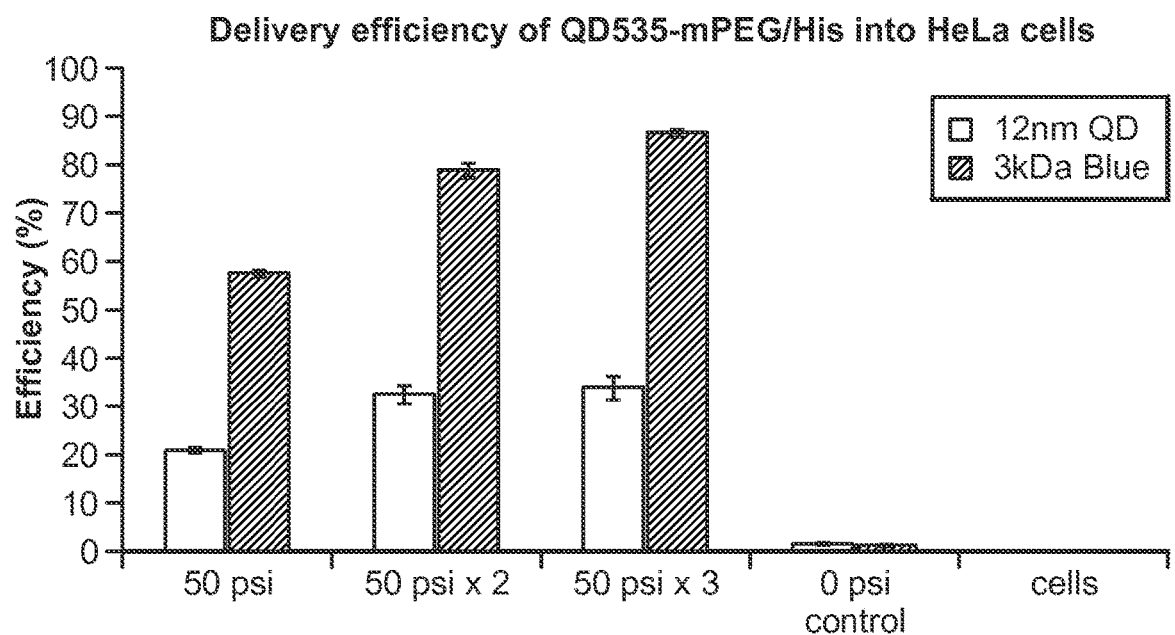
FIG. 20A illustrates delivery efficiency into HeLa cell cytosol upon current subject matter treatment with QDs coated with poly-imidazole ligand (PIL). Cell viability was >80% as measured by flow cytometry.
Figure 20B:
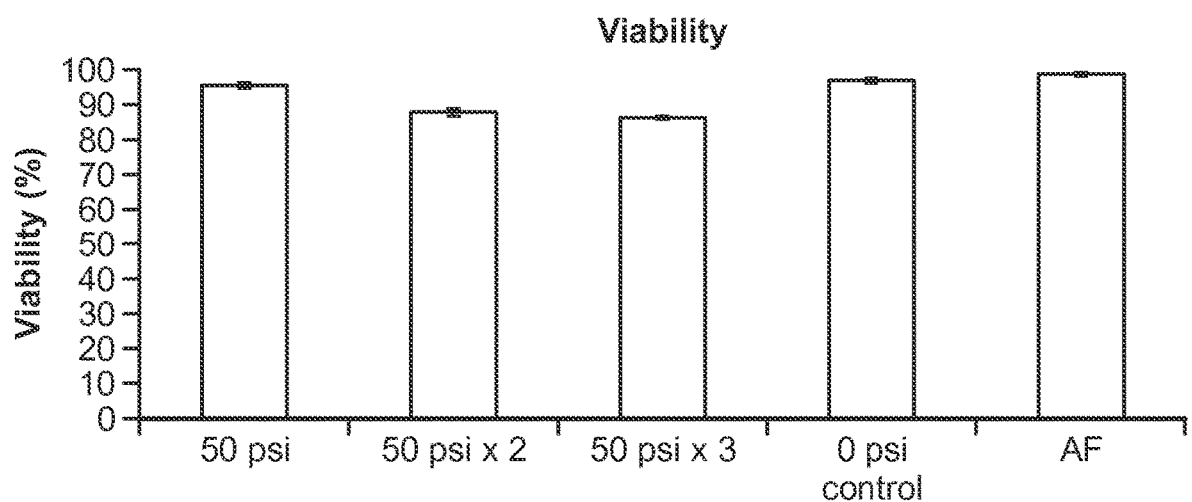
FIG. 20B illustrates viability of HeLa cells upon delivery of plain QD535 by the current subject matter, as measured by propidium iodide staining and flow cytometry measurement.

FIG. 19 is an overlay of transmission and confocal fluorescence images, followed by z-section confocal fluorescence images of treated cells delivered with QDs using the current subject matter. FIG. 19 illustrates (top) immediately after treatment (i.e. delivery) and (bottom) after 48 h incubation at 37° C. and 5% $CO_2$. The diffuse staining pattern is constrained to the cytoplasm and the nanoparticles appear not to enter the nucleus (dark region within the cell). Scale bar is 10 µm. The particular free poly-imidazole ligand that coated the QDs imaged in FIG. 19 had no functionality other than providing biocompatibility through PEG groups. Confocal microscopy images show that HeLa cells, detached and round after flowing through the microfluidic device, have diffuse cytoplasmic QD staining throughout different z-sections of the cell (FIG. 19, top). The diffuse staining persists even after 48 hours, following incubation and adherence of the cells at 37° C. in 5% $CO_2$ (FIG. 19, bottom). The diffuse QD fluorescence is dimmer at 48 hrs, likely due to cell division (FIG. 19). The device delivered QDs (~13 nm hydrodynamic diameter) into ~40% of the live cell population at a throughput rate of ~10,000 cells/s. FIG. 20A illustrates delivery efficiency into HeLa cell cytosol upon current subject matter treatment with QDs coated with PIL. Cell viability was >80% as measured by flow cytometry. FIG. 20B illustrates viability of HeLa cells upon delivery of plain QD535 by the current subject matter, as measured by propidium iodide staining and flow cytometry measurement. The viability of treated cells as measured by flow cytometry, the diffuse staining on the confocal images, and the cell's ability to adhere are consistent with delivery of QDs into the cytoplasm of a live cell.

To confirm that the fluorescence indeed arises from QDs delivered to the cytosol as opposed to QDs sequestered in endosomes, the nanoparticle was designed to change its emission profile upon interaction with the reducing environment of the cytosol. The reduction potential inside the cell cytoplasm is −260 to −220 mV and is primarily dictated by the maintenance of high concentrations (5-10 mM) of the tripeptide glutathione. Therefore, by measuring the fluorescence of a QD-dye construct whose emission changes when exposed to the cytosolic environment, the localization and chemical accessibility of the delivered nanoparticles can be determined. A QD-dye was constructed comprising of a green emitting QD ($\lambda$emission=541 nm) that acts as an energy donor to a carboxy-X-Rhodamine (Rox) dye ($\lambda$emission=610 nm), conjugated through a reducible disulfide bond.

Figure 21B:
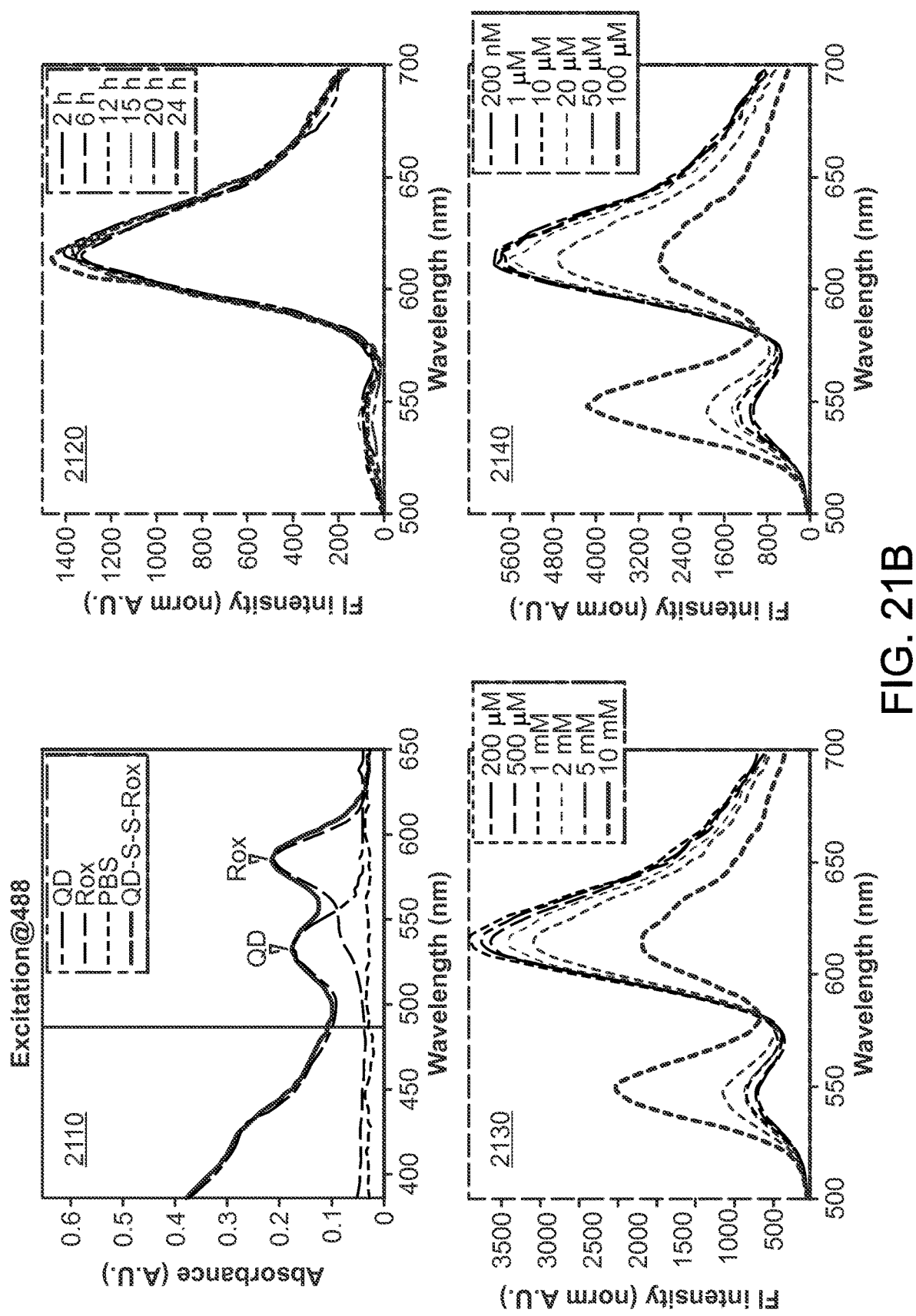
FIG. 21 illustrates construct design, absorbance, and stability in various media.

FIG. 21 illustrates construct design, absorbance, and stability in various media. At 2100 is a schematic of the PIL prior to conjugation with the dye and coating the QDs (left), and of the resulting QD-disulfide-Rox construct (right) (image not to scale). At 2110 is the absorbance spectrum of the QD-disulfide-dye construct. Excitation at 488 nm and at 405 nm provided exclusive absorption by the QDs throughout the experiment. At 2120 is the stability of fluorescence energy transfer from QD to Rox for the construct in full culture media at 37° C. and 5% $CO_2$, demonstrating that the disulfide bond is not cleaved in the extracellular environment. Plot 2130 illustrates cleavage of the disulfide bond by the cytosolic reductant glutathione, as shown by the recovery of QD fluorescence. At 2140, recovery of QD fluorescence upon treatment by the non-thiol reductant tris(2-carboxyethyl) phosphine is shown, further supporting the cleavage of the disulfide bond.

Thiol groups that were incorporated into the PIL formed disulfide bonds with thiolated Rox dyes. The absorbance spectrum of the purified construct has absorbance features of both QD and Rox (2120) at an average of 13 Rox dyes per QD, effectively quenching the QD fluorescence (2130). This construct serves as an irreversible sensor of the specific reducing environment in the cytosol. When the QD is selectively excited by a laser at 488 nm (microscopy) or 405 nm (flow cytometry) while the disulfide bridges are intact, the construct undergoes fluorescence resonance energy transfer (FRET) so that Rox emission in the red dominates. In a solution assay, the cellular reductant glutathione cleaves the disulfide bridges, releasing Rox dyes and allowing the QD fluorescence to recover (2140). The non-thiol based reductant tris-(2carboxyethyl) phosphine also allows QD fluorescence recovery, indicating that the release of Rox from the QD surface is not via PIL displacement by glutathione (2140). Rox fluorescence may not completely disappear due to some of the disulfide bridges being sterically hindered by long PEG groups on the PIL, and due to some small amount of non-specific interaction between the dye and the QD surface.

Changes in the fluorescence profile of the construct, as measured by flow cytometry and confocal microscopy, confirm the delivery of QD-disulfide-Rox constructs to the cell cytoplasm. When exposed to the reducing cytosolic environment, the cleavage of the disulfide bonds disrupts the FRET process from the QD to the dye. Therefore, upon exclusive excitation of the QD, QD channel fluorescence increases while Rox channel fluorescence decreases with time. Live HeLa cells were treated by the microfluidic device in a solution with a high concentration of QD-disulfide-Rox, incubated for 5 minutes, and washed to remove excess QDs before adding cell culture media (i.e. the treated cells). Control cells were incubated with QD-disulfide-Rox for 5 minutes instead of being treated by the microfluidic device, and washed before being placed in cell culture media. The Rox and QD channel fluorescence of these treated and control cells were observed by both confocal microscopy and flow cytometry.

Figure 22A:
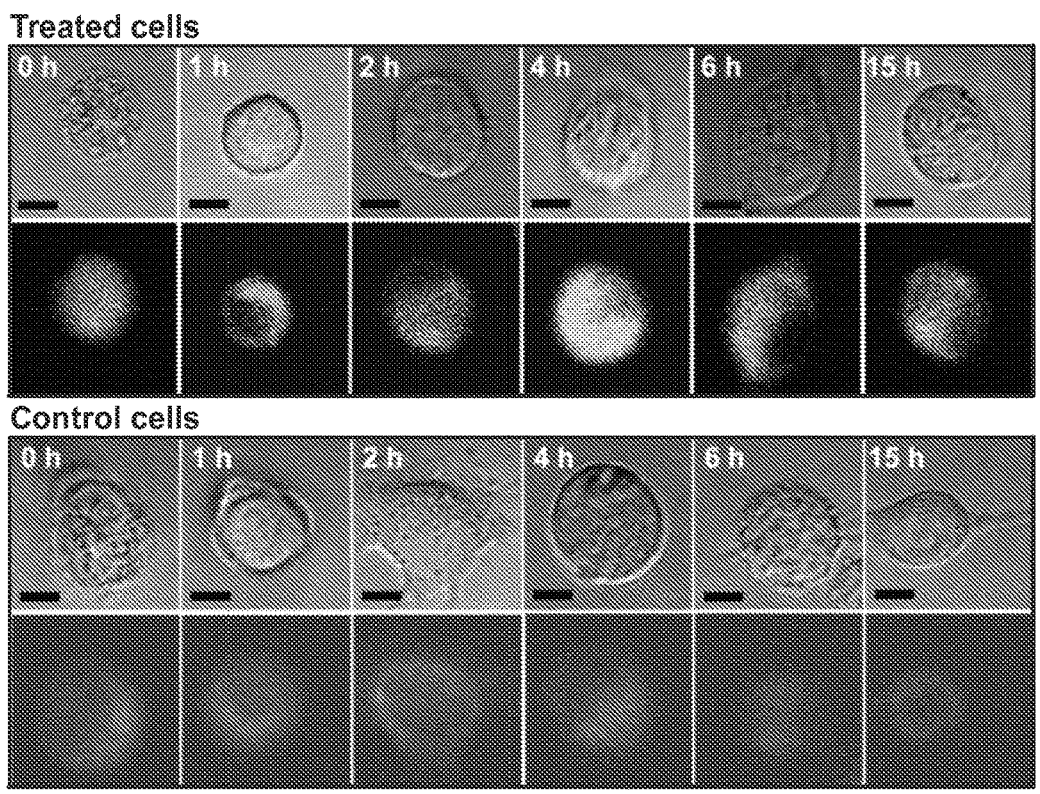
FIG. 22A illustrates live cell confocal microscopy images of treated and control cells.
Figure 22B:
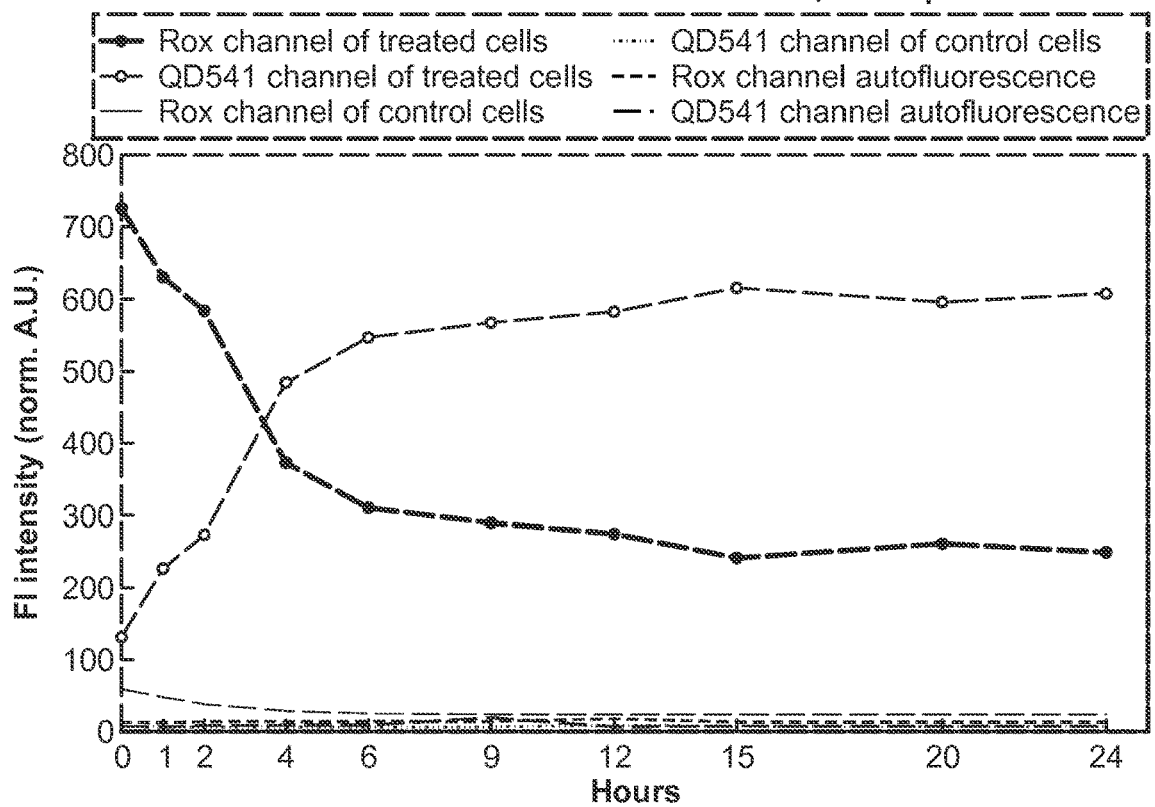
FIG. 22B illustrates a change in intensity of treated cells as a function of time in the green and red channels.

FIGS. 22A and 22B illustrate live cell confocal microscopy images and fluorescence intensity analysis demonstrating cytoplasmic staining and chemical accessibility of QD surface. FIG. 22A illustrates images of treated cells (top) and control cells (bottom). The appearance of diffuse green fluorescence is present only in treated cells. Scale bar is 10 µm. FIG. 22B illustrates a change in intensity as a function of time in the green and red channels. Because n<20 at each time point, fluctuations in total average fluorescence were corrected by normalizing to the 0 h time point.

Under the confocal microscope, the diffuse fluorescence that appears across the cytoplasm of treated cells progresses from strongly red to strongly green (as shown in FIG. 22A). Control cell images show some non-specific binding on the outer membrane as demonstrated by the ring-shaped fluorescence, and there is no increase in green channel signals. These effects are consistent with the expected cleavage of cytosolic disulfide bonds which reduce the FRET effect. In FIG. 22B, the line graph plots the average QD and Rox channel intensity per cell after correcting for cell-to-cell differences in delivered fluorescent material by normalizing for total fluorescence, for treated and control cells and autofluorescence. For treated cells, the graph shows a cross over between 2-4 hours of incubation where the QD fluorescence rises above the Rox fluorescence. Interestingly, the treated cell Rox signal is shown to stabilize above autofluorescence levels after 9 hours. This is consistent with results from solution assays, where some FRET remained after reduction. The observed diffuse staining and increase in QD signal and reduction in Rox signal strongly support cytosolic delivery and subsequent disulfide bond cleavage. The QD fluorescence in control cells, quenched by FRET to the Rox, appears indistinguishable from autofluorescence. The control cells display some Rox fluorescence above autofluorescence at early time points, which then steadily decreases. This can be attributed to non-specific interactions between QD-S-S-Rox and the surface of the cell, followed by re-solvation of the constructs into the medium.

FIG. 23 illustrates flow cytometry measurements of average cell fluorescence and viability. At 2300 is average fluorescence of QD (left) and Rox (right) per cell, showing an increase in QD fluorescence only in treated cells. Rox fluorescence in both treated and control cells is at autofluorescence levels by the 24 h time point. At 2310 is a histogram of the distribution of fluorescence intensities among treated and control cells at select time points, in the QD channel (left) and Rox channel (right). QD delivery is estimated to have occurred in at least 35% of the cell population. Grey areas are meant to guide the eye in the movement of fluorescence intensity histogram peaks. At 2320 illustrates viability of control and treated cells as measured by propidium iodide.

The flow cytometry measurements illustrated in FIG. 23 confirm that the QD-disulfide-Rox constructs can interact with the cytosolic environment. Flow cytometry measurements were recorded on all live cells, encompassing both delivered (~35% of the treated cell population) and undelivered cells. At 2100 the average fluorescence per cell of the treated and control populations is illustrated. The average QD fluorescence rises initially for the treated cells, peaking at ~9 hrs and falling gradually thereafter, in contrast to the QD fluorescence of the control cell population, which stays comparable to autofluorescence levels. This is consistent with the cytosolic reduction of disulfide bridges between the QD and dye inside the treated cells followed by dilution of fluorescence constructs by cell division. The Rox fluorescence for both the treated and control cells start high and drop within the first 2 hrs. This drop is attributed to the re-solvation into the medium of particles that had become bound to the cell surface during incubation. The average Rox fluorescence in the treated cell population appears similar to control cells due to the presence of undelivered cells within the treated population. The presence of both delivered and undelivered cells within the treated population can be distinguished in the histograms of QD and Rox intensity shown at 2310. With increasing time, the fluorescence histograms become bimodal for treated cells but stay unimodal for control cells. QD fluorescence rises with time in a subset of the treated cell population (2100), further supporting the disruption of the FRET process in the cytosol of treated and delivered cells. Rox fluorescence decreases overall as membrane-bound constructs are re-solvated into the medium, but a subset of the treated cell population retains Rox fluorescence. This is consistent with the incomplete reduction of QD-S-S-Rox bonds observed in confocal microscopy. The viability of the treated cell population, as measured by propidium iodide staining, is within 10% of the control population at all time points (2130). The cell viability of >90% relative to the control group compares favorably to alternative methods such as electroporation and polymer-based methods, which have yielded post-treatment viabilities as low as 40-60%.

Figure 24:
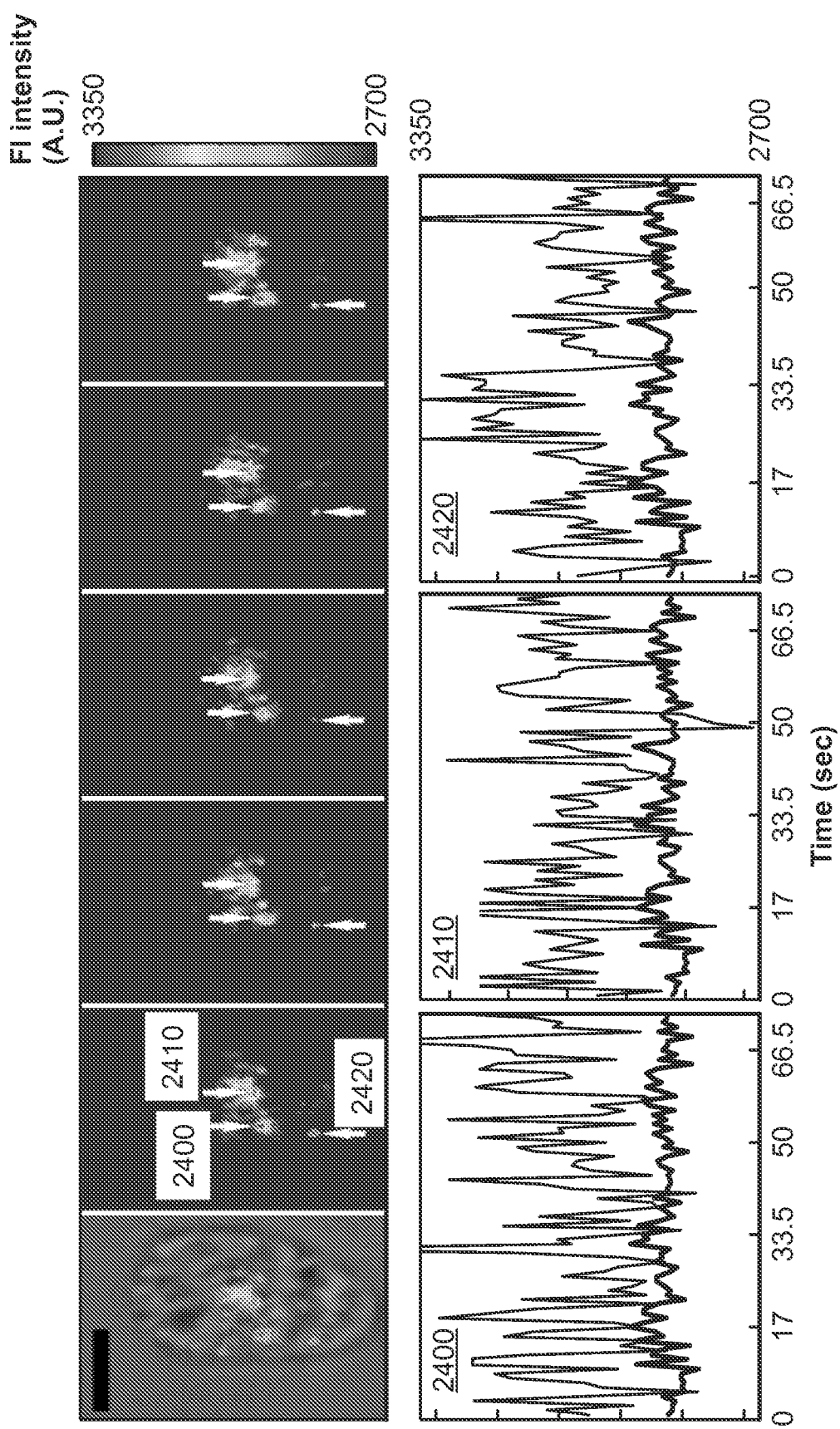
FIG. 24 illustrates epifluorescence imaging of unaggregated single quantum dots within the cell cytosol after device treatment with a 10 nM quantum dot solution, and blinking traces of three quantum dots with autofluorescence.

FIG. 24 illustrates epifluorescence imaging of unaggregated single QDs within the cell cytosol after device treatment with a 10 nM QD solution (top), and blinking traces of the three QDs labeled 2400, 2410, and 2420 with autofluorescence. QD blinking traces appear to be non-binary due to long acquisition bin times (500 ms). Scale bars are 10 μm.

The QD delivery platform also enabled single molecule imaging by delivering unaggregated QD-disulfide-Rox constructs, as the observed emission intermittency is consistent with single QDs. For this experiment, QD-disulfide-Rox constructs were delivered into the cytosol followed by a 10 hour incubation and imaged on an epifluorescence microscope. The 10 hour incubation ensured that the QD fluorescence from inside the cytosol has recovered via disulfide bond reduction; epifluorescence microscopy was used to ensure that enough photons are collected. Several blinking QDs were observed when cells were treated by the current subject matter at low QD concentrations (FIG. 24). Intensity traces of blinking QDs in the cytosol, shown at 2400, 2410, and 2420, appear non-binary as a result of long acquisition bin times (500 ms). Translational cell movements were deemed minimal during the time frame of the acquisition (~1 min). These data demonstrate the capability of observing single molecule events within the cell cytosol by delivering QDs as fluorescent labels using the current subject matter.

Example 1 demonstrates nanoparticle delivery into cell cytosol according to an embodiment of the current subject matter. By observing the cleavage of QD-disulfide-Rox by cytosolic reductants, it has been shown that the nanoparticle surface interacts with cytosolic components. Embodiments of the current subject matter enables delivery of QDs into cell cytoplasm at high throughput without any cell penetrating or endosome escaping ligands, while conserving cell viability and QD integrity. The delivery efficiency of 35% may be further increased by increasing the number of microfluidic constrictions, changing constriction dimensions, or increasing the number of treatment cycles. Unlike most of the current cell penetrating peptide or positive charge-assisted delivery methods, the current subject matter does not require dual conjugation of an intracellular delivery handle and a cytosolic protein-targeting handle on the same nanoparticle. By dispensing the need for the former, mitigation of the concerns of cross-reactivity, unequal reactivity efficiencies of conjugation strategies, and conjugation stoichiometry can be achieved. Therefore, significant flexibility in QD construct design is garnered, paving the way for intracellular protein labeling and tracking. The methods are useful for the delivery of many fluorescent nanomaterials with complex designs that target intracellular proteins and organelles through proven protein-targeting strategies such as, but not limited to, streptavidin-biotin, HaloTag-chloroalkane, and sortase tagging.

In example 1, all chemicals were obtained from Sigma Aldrich and used as received unless indicated otherwise. Air sensitive materials were handled in an Omni-Lab VAC glovebox under dry nitrogen atmosphere with oxygen levels <0.2 ppm. All solvents were Spectroscopic or reagent. Aromatic ring-bearing compounds were visualized on TLC using a hand-held UV lamp and KMnO4. Amine-bearing compounds were visualized on TLC using a Ninhydrin stain. Flash column chromatography was performed on a Teledyne Isco Combi Flash Companion. HeLa cells were purchased from ATCC and all cell medium materials were purchased from Mediatech unless indicated otherwise.

In example 1, 1H NMR spectra were recorded on a Bruker DRX 401 NMR Spectrometer. MS-ESI was performed on a Bruker Daltonics APEXIV 4.7 FT-ICR-MS machine. UV-Vis absorbance spectra were taken using an HP 8453 diode array spectrophotometer. Photoluminescence and absorbance spectra were recorded with a BioTek Synergy 4 Microplate Reader. Polymer molecular weights were determined in DMF solution on an Agilent 1100 series HPLC/GPC system with three PLgel columes (103, 104, 105 Å) in series against narrow polystyrene standards. Dye derivatives were purified using Varian ProStar Prep HPLC system. Modified polymer was purified using GE Healthcare's PD-10 columns packed with Sephadex™ G-25M. Ligand exchanged QDs were purified by centrifugation dialysis with Millipore Amicon Ultra 30K cut-off centrifugal filters and by GFC on AKTAprime Plus chromatography system (Amersham Biosciences) equipped with a self-packed Superdex 200 10/100 glass column. Flow cytometry measurements were made on LSR Fortessa (BD Biosciences).

In example 1, CdSe cores with 478 nm first absorption peak were synthesized using a previously reported method (1). To summarize, 0.4 mmol (54.1 mg) of CdO, 0.8 mmol (0.2232 g) of TDPA, 9.6 mmol (3.72 g) of TOPO were placed in 25 mL round bottom flask. The solution was degassed for 1 hr at 160° C. and heated to 300° C. under argon until the CdO dissolved and formed a clear homogenous solution. This was followed by putting the solution under vacuum at 160° C. to remove evolved water. The solution was reheated to 360° C. under argon and a TOP-Se solution (1.5 mL of 1.5M TOP-Se in 1.5 mL of TOP) was rapidly added to give CdSe cores with the first absorption feature at 478 nm.

CdS shells were deposited on CdSe cores via modification of previously reported procedures (2). Cores isolated by repeated precipitations from hexane with acetone were brought to 180° C. in a solvent mixture of oleylamine (3 mL) and octadecene (6 mL). Cd and S precursor solutions were then introduced continuously at a rate of 4 mL/hr. The Cd precursor consisted of 0.33 mmol Cd-oleate and 0.66 mmol oleylamine in a solvent mixture of octadecene (1.5 mL) and TOP (3 mL). The S precursor consisted of 0.3 mmol hexamethyldisilathiane [(TMS)$_2$S] in 6 mL TOP. Addition of a total of 3 monolayers each of Cd and S yielded QDs with emission at 541 nm and a quantum yield of 60% when diluted in octane. The extinction coefficient of CdSe(CdS) was calculated using the extinction coefficient of CdSe cores from the literature (3) and assuming that 95% of the CdSe cores were retained during the overcoating step.

In example 1, the silicon chip was fabricated using photolithography and deep reactive ion etching techniques. The resulting etched silicon wafer was cleaned (with H2O2 and H2SO4) to remove debris, oxidized to produce a glass surface, and bonded to a Pyrex wafer before being diced into individually packaged devices. Each device was then individually inspected for defects prior to use.

Example 2—Delivery of Macromolecules

Intracellular delivery of macromolecules is a critical step in therapeutic and research applications. Nanoparticle mediated delivery of DNA and RNA, for example, is useful for gene therapy, while protein delivery is being used to affect cellular function in both clinical and laboratory settings. Other materials, such as small molecules, quantum dots, or gold nanoparticles, are delivered to the cytosol for purposes ranging from cancer therapies to intracellular labeling and single molecule tracking.

To demonstrate the versatility of the technique, model dextran molecules were delivered to several cell types: DC2.4 dendritic cells, newborn human foreskin fibroblasts (NuFF) and mouse embryonic stem cells (mESC) attained delivery efficiencies of up to 55%, 65% and 30% respectively. Initial experiments also showed successful delivery in primary lymphocytes, macrophages and dendritic cells derived from mice. Moreover, the technique did not cause excessive cytotoxicity or induce stem cell differentiation. Indeed all cell types were over 60% viable even at the highest tested speeds. Device design and operating conditions had not been previously optimized for any of the aforementioned cell types.

Figure 25:
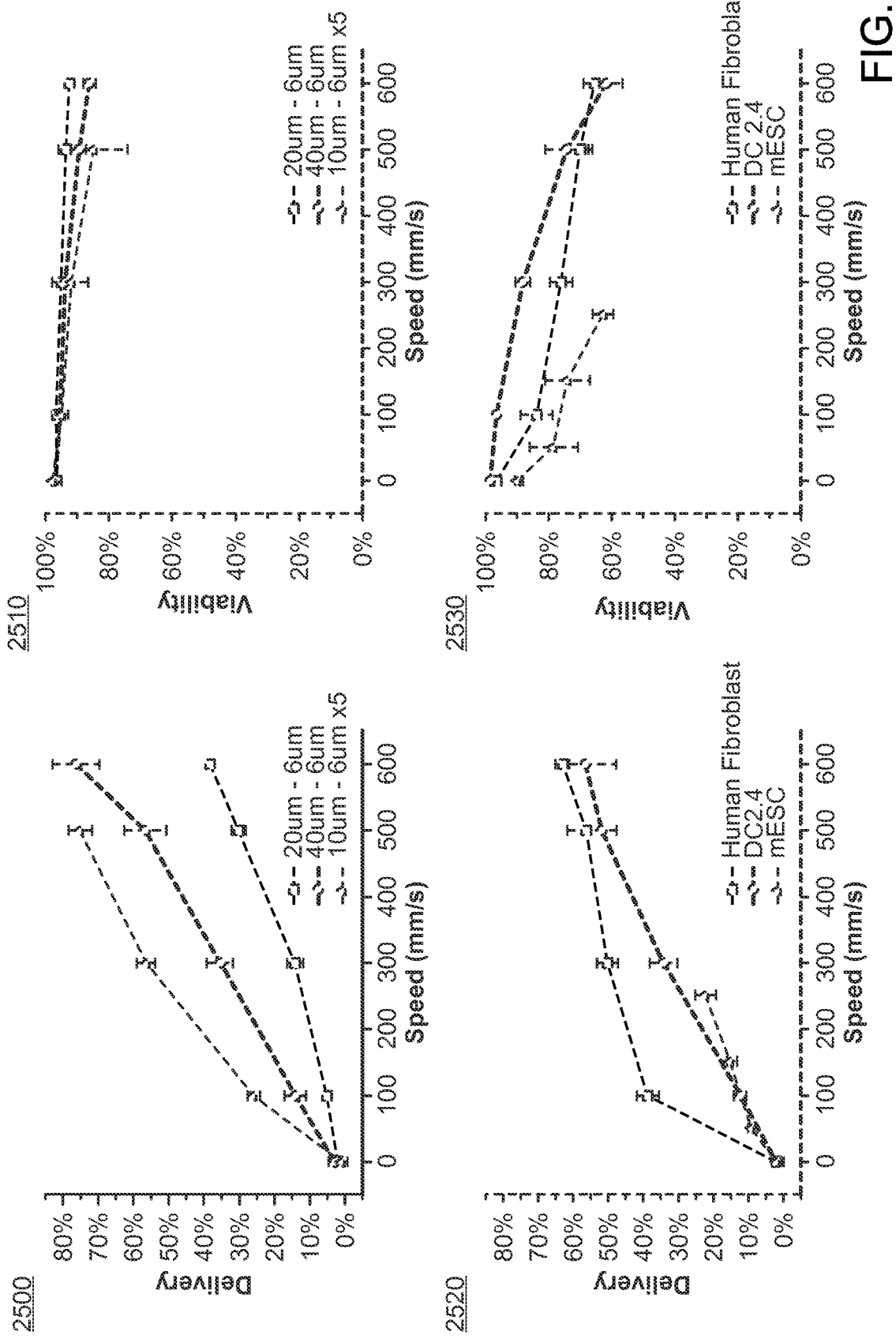
FIG. 25 illustrates experimental results showing that delivery performance depends on cell speed and constriction design.

FIG. 25 illustrates experimental results showing that delivery performance depends on cell speed and constriction design. Constriction dimensions are denoted by numbers (e.g. 10 μm-6 μm×5) such that the first number corresponds to constriction length, the second to constriction width and the third (if present) to the number of constrictions in series per channel. At 2500, delivery efficiency is shown and at 2510 cell viability 18 hours post treatment (measured by flow cytometry) is shown as a function of cell speed for 40 μm-6 μm (○), 20 μm-6 μm (□) and 10 μm-6 μm×5 (Δ) device designs. At 2520, delivery efficiency and 2530 cell viability (measured by flow cytometry) is shown as a function of speed in primary human fibroblasts (□), DC2.4 dendritic cells (○), and mouse embryonic stem cells (mESC) (Δ) treated by a 30 μm-6 μm device. Human fibroblast and dendritic cells were analyzed 18 hours post-delivery. MESCs were analyzed 1 hour post-delivery. All data points were run in triplicate and error bars represent two standard deviations.

Figure 26:
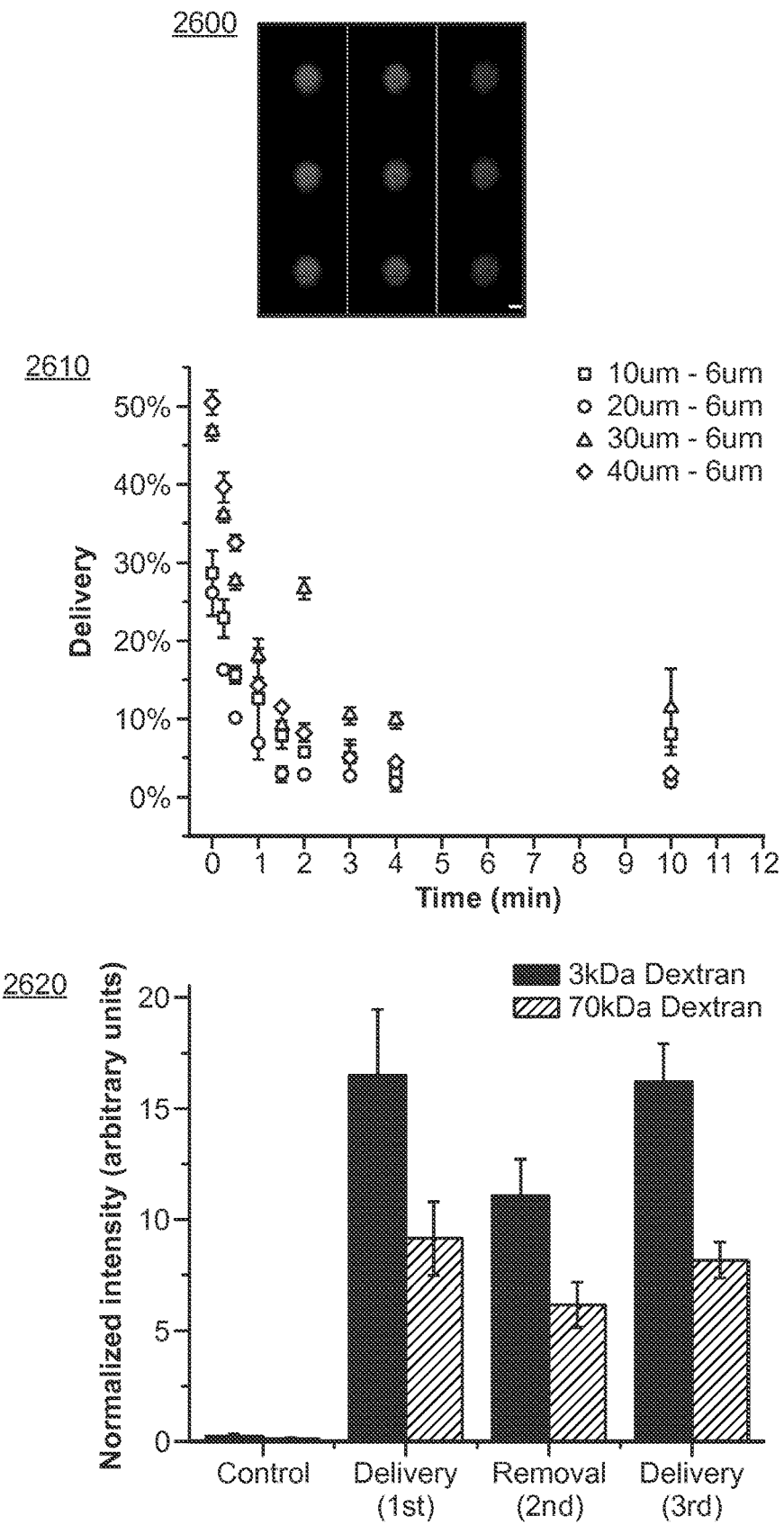
FIG. 26 illustrates scans of different horizontal planes of a HeLa cell after the delivery of pacific blue conjugated 3 kDa dextran, as measured by confocal microscopy.

FIG. 26 illustrates scans 2600 of different horizontal planes of a HeLa cell after the delivery of pacific blue conjugated 3 kDa dextran, as measured by confocal microscopy. Scans read from top to bottom, then left to right where the top left is at z=6.98 μm and bottom right is at z=−6.7 μm. Scale bar represents 6 μm. At 2610, live cell delivery efficiency of 10 μm-6 μm (□), 20 μm-6 μm (○), 30 μm-6 μm (Δ), and 40 μm-6 μm (◊) devices is shown. The time axis indicates the amount of time elapsed from initial treatment of cells before they were exposed to the target delivery solution. All results were measured by flow cytometry 18 hours post-treatment. At 2620, average intensity of the delivered cell population normalized by untreated cells to control for auto-fluorescence. Fluorescein conjugated 70 kDa dextran (horizontal lines) and pacific blue conjugated 3 kDa dextran (diagonal lines) are delivered to the cell (cycles 1 and 3) and removed from the cell (cycle 2) in consecutive treatment cycles. The control represents cells that were only exposed to the delivery solution and not treated by the device. All data points were run in triplicate and error bars represent two standard deviations.

As previous nanoparticle and cell penetrating peptide (CPP)-based delivery techniques exploit endocytotic pathways, evidence is presented that rules out the influence of endocytosis in the current subject matter delivery mechanism. FIG. 26 illustrates at 2600 confocal microscopy of cells treated with pacific blue conjugated 3 kDa dextran demonstrate diffuse cytosolic staining as opposed to the punctate characteristic one would expect of endocytotic methods. Moreover, when delivery experiments are conducted at 4° C., a temperature at which endocytosis is minimized, delivery efficiency is minimally affected by temperature for both test payload materials, 3 kDa and 70 kDa dextran. This data indicate that endocytosis is unlikely to be responsible for delivery in this system.

Delivery kinetics over time were characterized. Cells were treated by the current subject matter in the absence of delivery material and subsequently exposed to pacific blue labeled 3 kDa dextran at defined time intervals post-treatment. In this approach, as the cells pass through the constriction their membrane is disrupted; however, no measurable delivery occurs until they are exposed to the labeled dextran. Thus, the delivery efficiency at each time point would reflect the proportion of cells that remained porous for that amount of time post-treatment. This method captures the kinetics of pore formation/closure. The results indicate that almost 90% of delivery occurs within the first minute after treatment regardless of device design (2610). The observed time-scale supports the pore formation hypothesis as previous works on membrane repair kinetics have reported membrane sealing occurring at about 30 s after an injury is induced. In contrast, the recommended time-scale for endocytotic methods such as nanoparticle and CPP mediated delivery mechanisms is on the order of hours.

Since delivery of material through the membrane pores is diffusive, material could be exchanged into and out of the cell throughout the lifetime of the pore. Endocytotic or convective mechanisms, on the other hand, must be unidirectional, i.e. only facilitate transport of material into the cell. To demonstrate bidirectional transport of material across the cell membrane an experiment was conducted consisting of 3 delivery cycles. In the first cycle, cells were treated in the presence of 3 kDa and 70 kDa dextran, incubated for 5 min in the dextran solution and washed twice with PBS. One third of the sample was retained and plated for follow-up. In the second cycle, the remaining washed cells were treated by the device again but in the absence of any delivery material and incubated for another 5 min. Half of this sample was plated for follow-up. In the third cycle, the remaining cells from the second cycle were run through the device under the same conditions as the first cycle (i.e. in the presence of dextran), incubated for 5 minutes and washed twice in PBS. The cells were analyzed by flow cytometry 18 hours after the experiment. The changes in normalized fluorescence intensity demonstrate a net diffusion of dextran into the cells during the first cycle, out of the cells during the second, and back in during the third (2620). These results are thus consistent with the diffusive delivery mechanism.

FIG. 27 illustrates a simplified, 2D diffusion model developed in a software package known as COMSOL Multiphysics that simulates passive diffusion of material into a cell across a porated membrane. COMSOL Multiphysics is a finite element analysis, solver and Simulation software/FEA Software package developed by COMSOL for various physics and engineering applications, especially coupled phenomena, or multiphysics. At 2700, delivery/loss of material is shown as a function of membrane diffusivity. Simulation results indicating the percentage of material delivered/lost from the cell as a function of membrane diffusivity when the material of interest is in the buffer (□) or in the cell (○) at the time of poration. At 2710 is a graphical representation of the simulated system and the concentration gradient that forms across the membrane if material is delivered from the buffer to the cell.

Using literature values for particle diffusivities inside and outside the cell cytoplasm, the experimental results of FIG.

26 were qualitatively recreated with diffusion as the only mode of mass transfer. Moreover, by fitting the experimental data to this model, this technique delivers 10-40% of the delivery material in the buffer into the cell cytosol. By comparison, CPP methods for protein delivery are estimated to deliver only 0.1% of the buffer material to the cytosol.

A particle's size (or hydrodynamic radius) affects its diffusivity and its ability to enter membrane pores of a particular size. Thus, this parameter affects delivery efficiency in the pore formation/diffusion mechanism. In a series of experiments, test payloads of 3 kDa, 10 kDa, 70 kDa, 500 kDa, and 2 MDa dextrans conjugated to fluorescein or pacific blue were delivered. Fluorescein labeled plasmids estimated at 3.1 MDa were also delivered. These model molecules were selected based on their similarity in molecular weight to delivery materials of interest. 3 kDa-10 kDa dextran, for example, are of similar size to some short peptides or siRNA, while the 70 kDa-2 MDa range mimics the size of most proteins and some small nanoparticles.

FIG. 28 illustrates results of a two-tiered delivery of material. At 2800, live cell delivery efficiency, as a function of speed, for HeLa cells treated with Pacific Blue conjugated 3 kDa (□), fluorescein conjugated 70 kDa (○) and 2 MDa (Δ) dextran is shown. This experiment was conducted using a 10 μm-6 μm×5 chip. All data points were run in triplicate and error bars represent two standard deviations. 2810 and 2820, illustrate histogram overlays of flow cytometry data for HeLa cells that are untreated (red), treated at 700 mm/s (green), treated at 500 mm/s (orange), treated at 300 mm/s (light blue), or only exposed to the delivery material (control, dark blue). The delivery material consisted of pacific blue conjugated 3 kDa dextran (2810) and fluorescein conjugated 70 kDa dextran (2820).

The experiments have shown that molecules larger than 70 kDa have a different delivery profile relative to 3 kDa dextran (2800). The device produced a two-tiered delivery where a 10 μm-6 μm×5 device operated at 500 mm/s, for example, enables over 90% of live cells to receive the 3 kDa molecules, while about 50% receive the larger 70 kDa and 2 MDa molecules.

The histograms corresponding to these flow cytometry data indicate that 3 kDa dextran delivery produces two distinct peaks (2810). In the first subpopulation, cells exhibit mild delivery levels as observed by a peak shift relative to controls (controls account for endocytosis and surface binding as described earlier for the 0 mm/s data points) with a 2-6× increase in average fluorescence intensity. In the second population, cells exhibit enhanced delivery levels corresponding to a 20-100× increase in average fluorescence intensity relative to controls. This effect may indicate that the latter subpopulation of cells was more severely porated than the former, hence enabling an almost 10× increase in material influx. Indeed, as illustrated by the 300 mm/s, 500 mm/s and 700 mm/s curves, increasing the treatment severity, by increasing operating speeds, appears to increase the proportion of cells with enhanced delivery. One observes a similar characteristic for the delivery of larger 70 kDa dextran molecules (2820). The effect is less pronounced, however, as the lower particle diffusivity and possible size exclusion effects reduce the overall quantity delivered. The mild delivery population (first peak) only shows a 1.5-2× increase in average fluorescent intensity as compared to the 2-6× observed in the 3 kDa case. This effect could account for the discrepancy in the delivery data in 2800 as in the case of larger molecules the mild delivery population could be difficult to distinguish from controls based on the present definition of delivery. As a result, for larger molecules, such as the 70 kDa and 2 MDa dextran, one largely measures the second, enhanced delivery population To verify that material delivered by rapid mechanical deformation is active and biologically available in the cell cytosol a series of experiments were conducted delivering test payload GFP silencing siRNA (Ambion, USA) to HeLa cells expressing destabilized GFP. Dose dependent and sequence specific GFP knockdown (up to 80%) at 18 hours post-treatment was observed. The gene knockdown response to cell speed and device design was consistent with dextran delivery experiments such that higher speeds and multiple constriction designs yielded greater gene knockdown. Lipofectamine 2000 was used as a positive control in these experiments. Device design and operating parameters were not optimized for siRNA delivery prior to performing these experiments.

Figure 29:
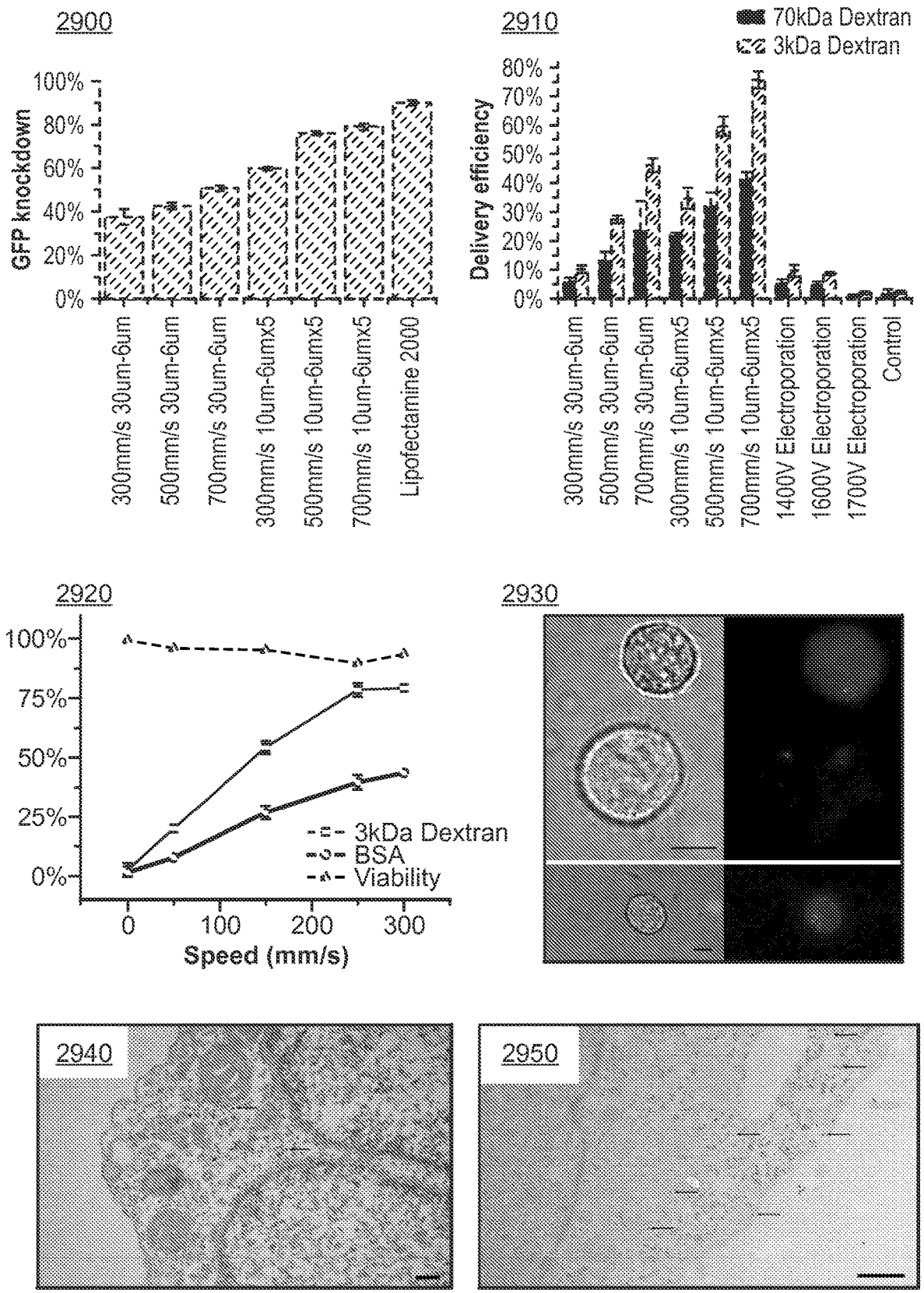
FIG. 29 illustrates data relating to SiRNA, protein, and nanoparticle delivery.

FIG. 29 illustrates data relating to SiRNA, protein, and nanoparticle delivery. At 2900, gene knockdown is illustrated as a function of device type and cell speed, in destabilized GFP expressing HeLa cells 18 hours after the delivery of anti-eGFP siRNA using a 10 μm-6 μm×5 chip at a delivery concentration of 5 μM. Lipofectamine 2000 was used as a positive control. At 2910, delivery efficiency of fluorescein labeled 70 kDa and pacific blue labeled 3 kDa dextran by rapid mechanical deformation and electroporation is shown. Each dextran type was at a concentration of 0.1 mg/ml in the delivery solution. At 2920, fluorescein labeled bovine serum albumin (○) delivery efficiency, pacific blue conjugated 3 kDa dextran (□) delivery efficiency, and cell viability (Δ), is shown as a function of speed, using a 30 μm-6 μm device. At 2930, fluorescent micrographs of HeLa cells immediately after delivery of antibodies to tubulin with an Alexa Fluor 488 tag are shown. Scale bars at 5 μm. At 2940 and 2950 is shown tunneling electron microscopy (TEM) images of gold nanoparticles (some indicated by arrows) in cells fixed ~1 s after treatment by a 10 μm-6 μm×5 device. Scale bars at 500 nm. All data points were run in triplicate and error bars represent two standard deviations.

In further experiments, cytosolic delivery potential is explored for previously challenging applications, such as protein and nanoparticle delivery. To compare the performance of the current subject matter to commercially available methods, 3 kDa and 70 kDa dextran was delivered, as a protein model, to human fibroblasts using the current subject matter and a Neon electroporation system (Invitrogen). Results indicate that rapid mechanical deformation provides a 7-fold increase or greater in delivery efficiency for such macromolecules (2910). To translate the method to protein delivery, a 30 μm-6 μm channel diameter device was used to deliver fluorescein labeled bovine serum albumin (BSA) to HeLa cells at up to 44% efficiency while maintaining viabilities above 90% (2920). Alexa Fluor 488 labeled antibodies to tubulin (BioLegend) were also delivered to HeLa cells after treatment with a 30 μm-6 μm device using a 0.25 mg/ml antibody concentration (2930). The diffuse staining indicates that the material is not trapped in endosomes and hence is suitable for live cell antibody staining of cellular structures in the cytosol. Apolipoprotein E was also delivered successfully using this technique.

For nanoparticle delivery, TEM images of cells fixed ~1 s after deformation (2940 and 2950) demonstrate the delivery of PEG1000 coated, 15 nm gold nanoparticles. The gold nanoparticles appear to be mostly un-aggregated and were not visibly sequestered into endosomes. In these images, evidence for various defects in the cell cytoplasm responsible for delivery were observed. High throughput has been demonstrated, non-cytotoxic delivery of quantum dots directly to the cell cytosol—a goal that previous techniques have struggled to achieve. In these experiments, quantum dots with a Rox dye bound to their surface were delivered by rapid mechanical deformation and observed over time. These data yielded a minimum estimated delivery efficiency of 35% and confirmed that the delivered quantum dots were in the cytosol and chemically accessible to the intracellular environment.

Transient pores are formed by rapid mechanical deformation of a cell as it passes through a microfluidic constriction. Data supports this mechanism by demonstrating diffuse cytosolic staining (FIG. 26 at 2600), siRNA functionality (FIG. 29 at 2900) and the bidirectional movement of material across the porated membrane (FIG. 26 at 2920). A number of parameters have been identified, such as constriction dimensions, number of constrictions in series and cell speed that affect delivery efficiency and viability (FIG. 25). These parameters may thus be used to optimize device design for individual applications based on cell type and the size of the delivery material.

In example 2, this technique is based on the microfluidic system, which can be incorporated into a larger integrated system consisting of multiple pre-treatment steps prior to delivery and analytical or sorting steps post-treatment. At an average throughput rate of 10,000 cells/s, the delivery device can, for example, be placed in-line with a flow cytometry machine to sort cells or perform other analytical tasks immediately after delivery.

The devices, systems, and methods described herein provide a number of potential advantages over existing methods. Similar to electroporation and microinjection, it is a poration based mechanism and hence does not rely on exogenous materials, chemical modification of payloads or endocytotic pathways. In contrast to electroporation, however, it does not rely on electrical fields which have had limited success in protein delivery, can damage some payload, or cause cytotoxicity. Indeed current results have demonstrated relatively high viability in most applications and sensitive payloads, such as quantum dots, appear to be undamaged. The current subject matter thus provides significant advantages in areas such as the labeling and tracking of cytosolic material where quantum dot damage due to electroporation can be an issue and the use of chemical delivery methods can restrict the range of available surface chemistries.

Example 2 has also demonstrated the device's ability to deliver proteins to the cell cytosol. Data and modeling estimates indicate that the current subject matter could deliver 10-100× more material per cell relative to previous practices, such as the use of cell penetrating peptides or electroporation. This improvement in delivery rates provides a powerful method for use in protein-based cell reprogramming, for example, where the delivery of transcription factors to the cell cytosol is a major hurdle to developing reliable methods of iPSC generation. One may also use the current subject matter to study disease mechanism by delivering various proteins/peptides of interest. Indeed the current subject matter can be used for high throughput screening of peptide libraries because, unlike most CPP or nanoparticle-based techniques, the current subject matter is insensitive to protein structure and chemistry, does not rely on endocytotic pathways, and does not affect protein functionality.

Because the current subject matter has demonstrated the potential for delivery to primary cells, cytosolic delivery by rapid mechanical deformation can be implemented as an ex-vivo treatment mechanism. In this approach, the patient's target cells, isolated from the blood or other tissue, are treated by the device outside of the patient's body and then re-introduced into the body. Such an approach takes advantage of the increased delivery efficiency of protein or nanoparticle therapeutics and is safer than existing techniques because, it obviates the need for potentially toxic vector particles and mitigates any potential side-effects associated with Reticuloendothelial clearance and off-target delivery.

In example 2, the silicon-based devices were fabricated at a microfabrication facility using photolithography and deep reactive ion etching techniques. In this process, 6" silicon wafers with a 450 µm thickness are treated with Hexamethyldisilazane (HMDS), spin coated with photoresist (OCG934, FujiFilm) for 60 s at 3000 rpm, exposed to UV light (EV1-EVG) through a chrome mask with the constriction channel design, and developed in AZ405 (AZ Electronic Materials) solution for 100 s. After 20 min of baking at 90° C., the wafer was etched by deep reactive ion etching (SPTS Technologies) to the desired depth (typically, in this example, 15 µm). Piranha treatment (H2O2 and H2SO4) were used to remove any remaining photoresist after the etching process was complete. To etch the access holes (i.e. inlet and outlet) the process was repeated on the opposite side of the wafer (i.e. the one not containing the etched channels) using a different mask, which contains the access hole patterns, and a thicker photoresist AZ9260 (AZ Electronic Materials).

Oxygen plasma and RCA cleaning were used to remove any remaining impurities. Wet oxidation was used to grow 100-200 nm of silicon oxide before the wafer was anodically bonded to a Pyrex wafer and diced into individual devices. Each device was individually inspected for defects prior to use.

Before each experiment, devices were mounted onto a holder with inlet and outlet reservoirs (all custom designed and produced by Firstcut). These reservoirs interface with the device using Buna-N O-rings (McMaster-Carr) to provide proper sealing. The inlet reservoir is connected to a pressure regulator system using Teflon tubing to provide the necessary driving force to push material through the device. Example 2 can accommodate pressures up to 70 psi.

Example 2 cell culture included HeLa (ATCC), GFP expressing HeLa, and DC2.4 (ATCC) cells were cultured in high glucose Dubelco's modified essential medium (DMEM, Mediatech) supplemented with 10% fetal bovine serum (FBS) (Atlanta Biologics) and 1% Penicillin Streptomycin (Mediatech). Primary human fibroblast cells (NuFF) (Globalstem) were cultured in high glucose DMEM supplemented with 15% FBS. Cells were kept in an incubator at 37° C. and 5% $CO_2$. When applicable, adherent cells were suspended by treatment with 0.05% Trypsin/EDTA (Mediatech) for 5-10 min.

Mouse embryonic stem cells (mESC) were grown on mouse embryonic fibroblasts (Chemicon) in media consisting of 85% knock out DMEM, 15% fetal bovine serum, 1 mM glutamine, 0.1 mM beta mercaptoethanol, and 1% non-essential amino acids supplanted with 1000 units/mL LIF (Millipore, USA). Cells were passaged every 2-3 days using 0.25% Trypsin/EDTA. When treated with the device, the mESCs were able to re-form colonies and retained normal morphology even 2 weeks after treatment.

To perform an experiment for example 2, cells were first suspended in the desired delivery buffer (growth medium, phosphate buffered saline (PBS), or PBS supplemented with 3% FBS and 1% F-68 Pluronics (Sigma)), mixed with the desired delivery material and placed in the device's inlet reservoir. This reservoir is connected to a compressed air line controlled by a regulator and the selected pressure (0-70 psi) was used to drive the fluid through the device. Treated cells are then collected from the outlet reservoir. Cells were incubated at room temperature in the delivery solution for 5-20 min post-treatment to ensure pore closure before being subject to any further treatment.

In example 2 experiments comparing delivery of different sized dextrans or protein vs. dextran, the molecules of interest were co-delivered i.e. they were used in the same experiment, with the same cell population, on the same device and differentiated based on their fluorescent labels. All experimental conditions were carried out in triplicate and the error bars represent two standard deviations.

To deliver fluorescently labeled dextran molecules (Invitrogen) or Apolioprotein E (Invitrogen), the example 2 experiments were conducted as described above such that the delivery buffer contained 0.1-0.3 mg/ml of dextran or 1 mg/ml of Apolioprotein E respectively.

To deliver fluorescein conjugated BSA (Invitrogen), cells were first incubated in culture media containing 5 mg/ml unlabeled BSA (Sigma) for 2 hours at 37° C. and then treated with the example 2 device using a delivery buffer containing 1 mg/ml of the fluorescein conjugated BSA. The pre-incubation step was intended to minimize non-specific binding of fluorescently labeled BSA to the cell surface.

GFP knockdown for example 2 was measured as the percentage reduction in a cell population's average fluorescence intensity relative to untreated controls. Lipofectamine 2000+siRNA particles were prepared by combining 1 μg of siRNA with 1 μl of Lipofectamine 2000 reagent in 100 μl of PBS. After 20 min of incubation at room temperature, 20 μl of this mixture was added to each experimental well containing ~20,000 cells and 100 μl of media. The cells were allowed to incubate with the particles for 18 hours prior to analysis.

In example 2, gold nanoparticles were prepared by conjugating thiol terminated, 1000 MW polyethylene glycol (PEG) to the nanoparticle surface, excess PEG was then washed four times by centrifugation (10,000 rcf for 30 min) and the resulting material suspended in PBS to a final concentration of 100 nM. To image GNP delivery to HeLa cells, the cells were suspended in PBS supplemented with 3% FBS, 1% F-68 Pluronics and 47 nM of GNP; treated by a 10 μm-6 μm×5 device and fixed in 2.5% (w/v) glutaraldehyde, 3% (w/v) paraformaldehyde, and 5.0% (w/v) sucrose in 0.1M sodium cacodylate buffer (pH 7.4). After an overnight fixation, the cells were post-fixed in 1% (w/v) OsO4 in veronal-acetate buffer for 1 h. They were then stained en bloc overnight with 0.5% uranyl acetate in veronal-acetate buffer (pH 6.0), dehydrated, and embedded in Spurr's resin. Sections were cut on a Reichert Ultracut E (Leica) at a thickness of 70 nm with a diamond knife. Sections were examined with an EM410 electron microscope (Phillips).

In example 2, a Neon electroporation system (Invitrogen) was used to transfect NuFF cells with fluorescein labeled 70 kDa and pacific blue labeled 3 kDa dextrans. Manufacturer's procedure was followed in washing cells and suspending them in the appropriate buffers. Cells were treated using a 10 μl tip at a density of $10^7$ cells/ml with a dextran concentration of 0.1 mg/ml. The three conditions used were as follows: 1) One 20 ms pulse of 1700V 2) Three 10 ms pulses of 1600V 3) Two 20 ms pulses of 1400V. Condition 1 and 3 were both recommended by the manufacturer as the optimal conditions for transfection of human fibroblast cells with eGFP plasmid delivery efficiencies of 84% and 82% respectively.

In example 2 confocal images, samples were centrifuged at 800 rcf for 4 min and washed 2-3 times with PBS prior to imaging. Confocal images were taken on live cells using the C1 confocal add-on unit on a Nikon TE2000-U inverted microscope with a 60× water-immersion lens. Fluorescence samples were excited by a 405 nm laser and detected using a standard DAPI filter (Nikon).

In example 2 fluorescence microscopy, samples were centrifuged at 800 rcf for 4 min and washed 2-3 times with PBS prior to imaging. Images were obtained using an Axiovert 200 (Zeiss) inverted microscope equipped with Neofluar lenses (Zeiss). Fluorescence excitation was provided by a X-cite 120Q mercury lamp (Lumen Dynamics). The microscope is fitted with a Hamamatsu C4742-95 camera (Hamamatsu) and images were analyzed by ImageJ (NIH).

In example 2 flow cytometry, for analysis of cells after a delivery experiment, cells were washed 2-3 times with PBS (>100 μl per well in a 96 well plate). These were then re-suspended in PBS supplemented with 3% FBS, 1% F-68 Pluronics and 10 ug/ml propidium iodide (Sigma). Cells were analyzed on an LSR Fortessa (BD Biosciences) or FACSCanto (BD Biosciences) equipped with a high throughput sampling robot. The 405 nm and 488 nm lasers were used for the excitation of the desired fluorophores. Propidium iodide (live/dead stain), fluorescein and pacific blue signals were detected using 695 nm long pass, 530/30 and 450/50 filters respectively. Data analysis was conducted using FACS Diva (BD Biosciences) and FlowJo (FlowJo) software.

Example 3—Stem Cells and Immune Cells

Proteins, nanoparticles, siRNA, DNA and carbon nanotubes were successfully delivered to eleven different cell types, including embryonic stem cells and immune cells. Indeed, the ability to deliver structurally diverse materials and its applicability to difficult to transfect primary cells indicate that the device and methods have wide applicability in research and clinical applications.

In example 3, each device consists of 45 identical, parallel microfluidic channels, containing one or more constrictions, etched onto a silicon chip and sealed by a Pyrex layer. The width and length of each constriction (described in more detail below) range from 4-8 uμm and 10-40 μm respectively. The example 3 device was typically operated at a throughput rate of 20,000 cells/s, yielding close to one million treated cells per device prior to failure, due to clogging. The parallel channel design was chosen to increase throughput, while insuring uniform treatment of cells, because any clogging or defects in one channel cannot affect the flow speed in neighboring channels (the device can be operated at constant pressure). Prior to use, the device can be first connected to a steel interface that connects the inlet and outlet reservoirs to the silicon device. A mixture of cells and the desired delivery material can be then placed into the inlet reservoir and Teflon tubing is attached at the inlet. A pressure regulator can be then used to adjust the pressure at the inlet reservoir and drive the cells through the device. Treated cells can be collected from the outlet reservoir.

Parameters that influence delivery efficiency that have been identified (see, e.g., example 2 above) can include cell speed, constriction dimensions and number of constrictions (thereby altering the shear and compression rates experienced by the cells). For example, delivery efficiency of membrane impermeable, pacific blue labeled 3 kDa dextran molecules to live HeLa cells increases monotonically with cell speed across different constriction designs (e.g., FIG. 25 at 2500). Constriction dimensions also impact delivery; increasing the constriction length from 20 μm to 40 μm almost doubled delivery efficiency at all operating speeds (e.g., FIG. 25 at 2500), with minimal effect on viability (e.g., FIG. 25 at 2510). Decreasing constriction width had a similar effect. Increasing the number of constrictions in series also increased delivery efficiency such that a device with five 10 μm length constrictions in series outperformed a single 10 μm, 20 μm or 40 μm length design across all cell speeds (e.g., FIG. 25 at 2500 and 2510). In these data, the 0 mm/s data points correspond to the control case whereby the cells undergo the same treatment as the other samples but are not passed through the device thus reflecting any endocytotic or surface binding effects.

To investigate the versatility of the technique its ability to deliver model dextran molecules to several cell types that are traditionally difficult-to-transfect was assessed, especially immune cells and stem cells. Fluorescently labeled 70 kDa and 3 kDa dextran were used for these experiments because they are similar in size to many protein and siRNA molecules respectively, easy to detect by flow cytometry, and have minimal surface binding effects as they are negatively charged.

Figure 30:
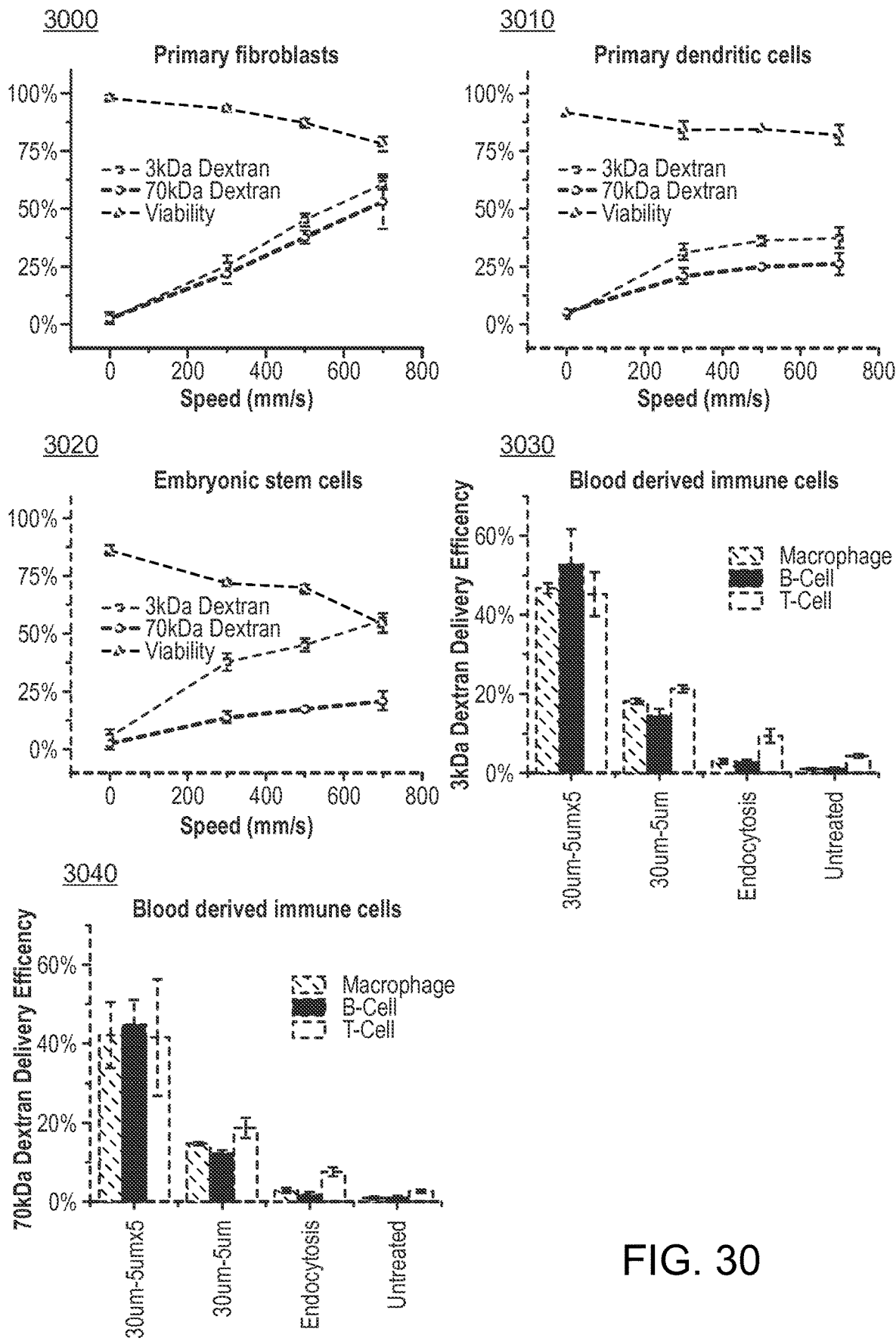
FIG. 30 illustrates applicability of the current subject matter across cell types.

FIG. 30 illustrates applicability of the current subject matter across cell types. At 3000 is shown delivery efficiency and viability of NuFF cells treated with a 30 μm-6 μm device to deliver 3 kDa and 70 kDa dextran. At 3010 is shown delivery efficiency and viability of spleen isolated, murine dendritic cells treated with a 10 μm-4 μm device to deliver 3 kDa and 70 kDa dextran. At 3020 is shown delivery efficiency and viability of murine embryonic stem cells treated with a 10 μm-6 μm device to deliver 3 kDa and 70 kDa dextran. At 3030 is shown delivery efficiency of 3 kDa and at 3040 is shown 70 kDa dextran to B-cells (CD19$^+$), T-cells (TCR-$\beta^+$) and Macrophages (CD11b) isolated from whole mouse blood by centrifugation and treated by 30 μm-5 μm and 30 μm-5 μm×5 devices at 1000 mm/s. 3 kDa and 70 kDa dextran were labeled with pacific blue and fluorescein respectively. All data points were run in triplicate and error bars represent two standard deviations.

Using various device designs dextran molecules were delivered to newborn human foreskin fibroblasts (NuFF) (3000), primary murine dendritic cells (3010), and embryonic stem cells (3020). These experiments yielded minimal loss (<25%) in cell viability (3000, 3010, and 3020) and results in murine embryonic stem cells indicate that the method does not induce differentiation. In further studies, white blood cells (buffy coat layer) were isolated from murine blood by centrifugation and treated them with the device. B cells, T cells and Macrophages, as differentiated by antibody staining, indicated successful delivery of both 3 kDa and 70 kDa dextran (3030 and 3040).

In order to illustrate the current subject matter's potential in addressing current delivery challenges, a number of experiments were conducted in possible applications ranging from cell reprogramming to carbon nanotube based sensing. In addition to the application specific materials detailed below, the current subject matter has demonstrated the successful delivery of a variety of test payloads such as Apolioprotein E, bovine serum albumin and GFP-plasmids.

FIG. 31 illustrates data from nanomaterial and antibody delivery. At 3100 is shown delivery efficiency and viability of HeLa cells treated with a 10 μm-6 μm×5 device to deliver pacific blue labeled 3 kDa dextran and Cy5 labeled, DNA wrapped, carbon nanotubes. At 3110 is shown bright-field cell images overlaid with Raman scattering in the G-band (red) to indicate delivery of carbon nanotubes in treated cells (left) vs. endocytosis (right). Scale bars at 2 μm. At 3120 is shown fluorescent micrograph of a HeLa cell 18 h after delivery of pacific blue labeled 3 kDa dextran (middle panel) and antibodies to tubulin with an Alexa Fluor 488 tag (right panel). Scale bars at 3 μm. At 3130 is shown delivery efficiency and viability of HeLa cells treated with a 10 μm-6 μm×5 device, at 500 mm/s, to deliver Alexa Fluor 488 labeled anti-tubulin antibodies. Delivery efficiency at different antibody concentrations is compared to an endocytosis control at 100 μg/ml and untreated cells Verification of successful delivery of carbon nanotubes (encapsulated by a DNA oligonucleotide) by flow cytometry (3100) and Raman spectroscopy (3110). Antibodies to tubulin were also delivered (3120 and 3130) using this technique, yielding a diffuse distribution throughout the cell that would be consistent with cytosolic delivery. The aforementioned materials are currently difficult to deliver to the cell cytosol and each material often requires a specialized modification to facilitate delivery. In example 3, all four materials were delivered to HeLa cells using the same set of conditions on a 10 μm-6 μm×5 device.

Efficient delivery of proteins to primary cells can enable several therapeutic applications. A challenge in cell reprogramming, for example, is the inefficiency of previous CPP based protein delivery methods. FIG. 32 illustrates protein delivery applications. At 3200 is shown a western blot analysis of c-Myc, Klf-4, Oct-4 and Sox-2 delivery by cell penetrating peptides versus a 10 μm-6 μm device to NuFF cells. Each of the four proteins has an additional 9 arginine (9R) groups to facilitate uptake. The lysate (Ly) columns correspond to the protein content of cells that are washed and lysed while the soup columns correspond to the protein content of the media environment. At 3210 is shown delivery efficiency and viability of spleen isolated, dendritic cells treated with a 10 μm-4 μm device to deliver pacific blue labeled 3 kDa dextran and Alexa Fluor 488 labeled ovalbumin. All data points were run in triplicate and error bars represent two standard deviations.

The ability to deliver four exemplary transcription factors (Oct4, Sox2, c-Myc, and Klf-4) to human fibroblast cells were examined and compared to a CPP method (3200). The results show that in addition to not relying on endocytosis, which can leave much material trapped in endosomes, delivery by rapid mechanical deformation yields significantly higher delivery efficiency for all 4 proteins. This result is in line with the aforementioned simulation work which indicated the current subject matter can have a 10-100× improvement in protein delivery relative to CPPs.

Antigen presentation in dendritic cells (DCs) is another area in which the current subject matter offers an advantage. Researchers have been exploring methods to express antigens on the MHC class I receptors of DCs so as to induce a potent cytotoxic T cell response. The current subject matter, which has direct clinical implications in preparation of a cancer vaccine, for example, relies on the cytosolic delivery of antigenic proteins, because MHC class I presentation is almost exclusive to cytosolic proteins. By facilitating direct cytosolic delivery of material, the current subject matter serves as a platform for generating an in vivo cytotoxic T cell response against a specific antigen. To illustrate this capability, Alexa 488 labeled ovalbumin, a model antigen protein, was successfully delivered to murine dendritic cells derived from the spleen (3210). Despite the higher rate of endocytosis in this cell type, the device produced a significant increase in delivery rates relative to the endocytosis controls (0 mm/s). Moreover, the delivered material is present in the cytoplasm by virtue of the cell deforming mechanism. This feature is particularly important for antigen delivery, because cytoplasmic pressure is a critical requirement for MHC class I antigen presentation.

The system of example 3 is an enabling research tool with its ability to deliver carbon nanotubes, gold nanoparticles and antibodies (FIG. 31)—three materials that are difficult to deliver with current techniques. The current subject matter significantly expands ability to probe intracellular processes by facilitating antibody and quantum dot staining of live cell structures/proteins and enabling the use of carbon nanotubes as a cytosolic molecular probe or chemical sensor. As a robust method of protein delivery, it can be used for high throughput screening of peptide/protein libraries because, unlike most CPP or nanoparticle-based techniques, this method is insensitive to protein structure and chemistry, does not rely on endocytotic pathways, and does not affect protein functionality.

Additionally, the current subject matter is useful for therapy (FIG. 32). For example, a patient's target cells are isolated from the blood or other tissue, treated by the device to deliver the desired therapeutic, and re-introduced into the body. Such an approach capitalizes on increased delivery efficiency of therapeutic macromolecules and is safer than existing techniques, because it obviates the need for potentially toxic vector particles and mitigates any potential side-effects associated with Reticuloendothelial clearance and off-target delivery.

Example 4—Personalized Cancer Vaccinations

Current challenges in the intracellular delivery of macromolecules are a significant barrier to better understanding disease mechanisms and the implementation of novel therapeutic approaches. Despite recent advances in delivery technology, treatment of patient-derived cells remains a challenge and current methods often rely on toxic electrical fields or exogenous materials. The microfluidic platform and related systems and methods rely on the mechanical deformation of cells to facilitate delivery. This controlled, physical approach has produces results in previously challenging areas, such as protein-based cell reprogramming and quantum dot delivery.

The most effective and direct way to influence the behavior of a cell is by delivering active agents to the cell cytoplasm. Intracellular delivery of macromolecules thus plays a critical role in research and development (R&D), with applications ranging from drug discovery to the study of biochemical processes to therapeutic applications. Current methods, however, have limitations. They often have low efficacy in patient-derived (primary) cells, rely on toxic electrical fields or exogenous material, and are ill-suited for the delivery of structurally diverse materials, such as proteins.

A robust delivery platform capable of addressing these issues enables significant advances in biological research and serves as the basis for a new generation of therapies such as personalized cancer vaccination. An effective protein delivery method for immune cells, for example, can serve as a cancer vaccination platform.

As described above, the microfluidic devices, related systems and methods described herein facilitates intracellular delivery of material by rapidly deforming a cell as it passes through a constriction. The deformation process causes transient disruption of the cell membrane and thereby enables the passive diffusion of material from the surrounding buffer into the cell cytosol. By eliminating the need for the exogenous materials and electrical fields that current methods rely on, this approach provides a simplified, robust approach to delivery with reduced toxicity. Hence, this method can serve as a broad platform to intracellular delivery of macromolecules with advantages in some research and clinical applications, such as cancer vaccination.

FIG. 34 is an illustration depicting a system in which a patient's blood is treated by a microfluidic device for the delivery of macromolecules. One embodiment of the current subject matter includes a system in which dendritic cells (DCs), isolated from a patient's blood, are treated by the device, ex vivo, to activate them against a particular cancer antigen and then reintroduced into the patient's blood stream. For example, delivered antigen is a commonly expressed protein known to be associated with a particular disease or a patient-specific one obtained from a biopsy. By delivering cancer antigens directly to the DC cytoplasm, one can exploit the MHC-I antigen presentation pathway and induce a powerful cytotoxic T lymphocyte (CTL) response in the patient. These activated T-cells then seek out and destroy any cancerous cells which express the target antigen. The platform's flexibility in using established, disease-specific antigens or those derived directly from a patient's tumor allow it to treat patients that are resistant to other therapies. Indeed this provides a personalized, targeted disease response with minimal side-effects. This embodiment can be implemented in a typical hospital laboratory (<1 hr per treatment) with a trained technician. Due to its small size and relative simplicity, a patient operated treatment system can also be used.

The cancer vaccine method has been demonstrated in a mouse model. The system has been used for the successful delivery and processing of ovalbumin, a model antigen, to murine dendritic cells and as indicated by increased presentation of the antigen, SIINFEKL peptide, on MHC class I receptors. These treated dendritic cells promote a proliferative cytotoxic T lymphocyte (CTL) response in vitro. Treated DCs are reintroduced into the animal to generate an in vivo CTL response. The devices are useful to deliver antigens to DCs isolated from human blood.

The data indicates that the device is capable of delivering material to sensitive, primary cells (including DCs) without causing excessive cell death. Thus, cell damage is not a serious issue. Immune response can be improved by increasing the number of treated cells, increasing the quantity and diversity of antigen delivered, and/or co-delivering activating factors, such as lipopolysaccharide. Little or no toxicity has been observed with cells treated with the device, thus making the methods not only feasible but advantageous for therapeutic human and veterinary applications.

Example 5—Blood Cancer Treatment

As described in example 4, rapid mechanical deformation of cells can provide a robust means of delivering antigens to dendritic cells (DCs) and thus can be a platform for cellular therapies. This system is based on the discovery that rapid mechanical deformation of cells can cause the formation of transient membrane pores that enable diffusive delivery of material from the surrounding medium. Unlike existing therapies discussed earlier, this method does not rely on custom fusion proteins, antigen cross-presentation, viral vectors, nanoparticles or endocytosis mechanisms; therefore, it provides great improvements in efficacy in vivo while reducing therapeutic costs. The flexibility and simplicity of this fundamentally different approach enables a broad platform for dendritic cell activation that can induce a CD8 response against a variety of cancer antigens. The system can target blood cancers, such as B cell lymphoma, which are more amicable to immune therapies, as well as several additional cancer types (e.g. Melanoma, Pancreatic cancer, etc.) and provides a vital, personalized new approach to combat the disease.

Cellular therapy against cancer is an attractive option due to its ability to activate the patient's immune system and drive a long-lasting antigen-specific CD8 T cell response against the disease. These therapies, such as the recently approved Provenge® for prostate cancer, have minimal side-effects relative to chemotherapies and radiation treatment. However, one of the greatest barriers to developing cellular therapies has been achieving proper antigen presentation by delivering antigens into the cell cytoplasm. Traditionally, activation of a CD8 effector response differentiates from a CD4 response by the location of the foreign protein entering the antigen presenting cell (e.g. dendritic cell). Proteins found in the cytoplasm induce a CD8 response while extracellular proteins captured by endocytosis induce a CD4 response. Since the mechanism of cross presentation within antigen presenting cells remains elusive, one must develop a reliable method of delivering the desired antigen directly to the cell cytoplasm to advance therapies utilizing the potent cytotoxic effector CD8 response. A robust, effective method of cytoplasmic delivery to dendritic cells is used as a platform to induce immune responses against a variety of cancer types.

Experiments on HeLa cells, illustrated in FIG. 8A and FIG. 11, have indicated that rapid mechanical deformation of the cell results in the formation of transient injuries/pores in the cell membrane, which enable the passive diffusion of material from the surrounding buffer into the cell cytoplasm. This previously unreported phenomenon produces cells that are viable and proliferate normally after treatment. Experiments have indicated that larger molecules exhibit lower delivery rates than smaller ones, thereby indicating a diffusive mechanism. Successful siRNA delivery and diffuse cytosol staining, as measured by confocal microscopy, also indicate that the delivered materials are in the cytosol and in an active/accessible state. Traditionally, methods of antigen delivery often show promise in cell lines but fail to translate to primary immune cells. The delivery method described herein, however, is independent of endocytotic pathways or cellular response to exogenous materials, which can vary significantly across cell types, and relies primarily on membrane bilayer properties. Hence, due to its simplicity and novel pathway, this technology is more amicable to transitioning from cell line to primary immune cell delivery and thus provides a major improvement in antigen presentation.

MHC class I presentation of antigens and dendritic cell maturation can be analyzed by antibody staining in response to delivery of ovalbumin protein. T cells harvested from OT-I and OT-II TCR transgenic mice can also be used to measure CD8 and CD4 proliferation in response to ovalbumin and/or SIINFEKL antigen loading. The system can be optimized for increased CD8 proliferation as compared to dendritic cells primed by endocytosis alone.

Primary murine dendritic cells are purified by MACS CD11c+ separation (Miltenyi Biotec, Germany) from the spleens of B6 mice. A device that contains constrictions with a 6 µm channel width capable of porating a 13 um HeLa cell's membrane can be used. Due to the smaller size of these dendritic cells, microfabrication and testing devices with channel widths of 3-5 µm can be utilized performance. Existing protocols for photolithography and deep reactive ion etching can be modified to enable efficient manufacture of these devices. Fluorescently labeled dextran molecules can be used as model molecules to assess delivery efficiency by FACS. Subsequently, ovalbumin protein can be delivered to the cells and assayed by a western blot to confirm protein uptake in primary cells.

Dendritic cell maturation can be examined by CD80 and CD86 antibody staining to show the rapid deformation method induces cell maturation. The use of extracellular TLR agonists, such as lipopolysaccharide (LPS), can be considered if it is deemed necessary to manually induce DC maturation post-delivery. Ovalbumin protein can be delivered to dendritic cells and antigen presentation can be quantified by MHC-I-SIINFEKL antibodies. Additionally, antigen presentation efficiency in response to delivery of TCR specific peptides can be assessed to show the system's ability to deliver/present antigenic proteins vs. peptides. Subsequently, CD8 and CD4 T cells can be harvested from TCR transgenic OT-I and OT-II mice respectively, stained by CFSE, and co-cultured with ovalbumin treated dendritic cells for 5 days. T cell proliferation of both subsets can be measured by FACS. Device design can be optimized to produce increased levels of functional CD8 T cell populations in comparison to conventional in vitro methods (e.g. endocytosis).

A versatile ability to induce antigen-specific CD8 responses has been a goal of cancer cellular therapies that has proved elusive thus far due to inefficient antigen presentation or inadequate flexibility of the delivery method. Existing methods have a number of drawbacks including their reliance on damaging electrical fields, the use of exogenous materials, protein sequence modification and/or endocytotic pathways to facilitate antigen delivery. The current subject matter, however, provides a fundamentally different approach to cytosolic delivery that does not suffer from any of the aforementioned problems. Moreover, by nature of its poration-diffusion mechanism, this method is broadly applicable across antigen types and could thus address a range of target cancers. The same mechanism can even be used to introduce additional signaling molecules to improve DC maturation/activation to produce a more potent T cell response. Such a broad-based platform is more versatile and robust than any existing antigen delivery/presentation mechanisms under investigation for cancer vaccines.

Example 5 can have a broad impact. Given the immense social burden of cancer across the country (estimated 570,000 deaths in the U.S. in 2011); cancer is likely to afflict a significant proportion of the population The afflicted population benefit from the development of novel cell therapies that harness the power of the patient's immune system to combat the disease. The current subject matter is a more efficient, personalized treatment platform for a variety of cancer types, such as blood cancers, e.g, leukemias, lymphomas, and multiple myelomas, as well as myeloproliferative neoplasms and myelodysplastic syndromes. The methods are also particularly useful for treatment of metastatic cancers, e.g., due to their propensity to disseminate via blood circulation. Cancers with unknown antigen epitope, for example, may be treated by digesting a tumor biopsy sample, delivering the lysate to the patient's DCs, and reintroducing the DCs into the body. This would enable one to activate the host's T cells against a broad range of cancer antigens thereby ensuring effective, multi-target treatment. This personalized aspect could be of particular interest to people who could develop rare forms of cancer, often ill-served by current treatments, due to exposure in hostile environments. By tailoring treatment to the individual's disease, this method can provide timely, effective care in even the most aggressive cases, such as multi-drug resistant cancers. This immune-based therapy can also be particularly effective at preventing metastasis (responsible for ~90% of cancer related deaths) as CD8 T cells may easily locate and destroy metastatic cells while the immunological memory provided through these treatments could prevent future relapse. In addition, as a research tool, this method can enable unprecedented mechanistic studies of antigen processing to better understand the process of antigen cross-presentation and hence improve the efficacy of existing/alternative immune activation methods.

Example 6—Cell Reprogramming

Stem cells play a critical role in current research in regenerative medicine, especially within the rapidly expanding field of tissue engineering. iPSCs are of particular interest due to their capacity for self-renewal, demonstrated ability to differentiate into any cell type, and autologous (patient specific) characteristics. Thus, iPSCs provide an opportunity to derive multi-lineage progenitor cells from a common pluripotent source, which may be combined into distinct yet interactive tissue compartments. Moreover, these cells could eventually obviate the need for human embryonic stem cells (hESCs) in clinical applications thus avoiding many of the moral and ethical debates that have plagued these cell types. Furthermore, patient-derived iPSCs avoid or minimize the immune rejection problems of hESC-derived cells. Thus, current research is largely focused on devising efficient, virus-free, protocols to produce large numbers of iPSCs.

iPSCs were originally generated by reprogramming adult murine and human fibroblasts (HFs) to a pluripotent state based on retro-viral overexpression of the 4 transcription factors Oct 3/4, Sox2, c-Myc and Klf4. These iPSCs are not only largely identical to ES cells in global gene expression, DNA methylation, and histone modification, but are also able to differentiate into cell types representing all 3 germ layers. While iPSC technology has enormous potential for biomedical research and cell-based therapy, major obstacles must be overcome to realize its full potential. For instance, most iPSC lines have been derived from various somatic cells by retroviral or lentiviral introduction of reprogramming factor-encoding genes, resulting in multiple chromosomal disruptions by viral vector integration, any of which may cause genetic dysfunction and/or tumor. In addition, reprogramming transgenes (in particular, c-Myc and Klf4) are closely associated with oncogenesis raising the possibility that its residual expression and/or reactivation may cause tumor formation. Thus, many laboratories recently explored different genome non-integrating approaches such as adenoviruses, episomal vectors, mRNAs, and microRNAs. Notably, it has been shown that iPSCs can be generated by direct delivery of the four reprogramming factors (Oct 3/4, Sox2, c-Myc and Klf4) fused to cell-penetrating peptides (CPP). While it has been reported that generation of mouse iPSCs can occur by delivery of four CPP-fused factors expressed in E. coli, it can be shown that human iPSCs can be generated by four CPP-fused factors expressed in mammalian cells. However, both studies reported that the reprogramming efficiencies of protein-based reprogramming is very low (<0.01%). Since protein-based reprogramming does not involve any type of genetic material (DNA or RNA) and vector vehicle (virus or plasmid), direct delivery of proteins provides one of safest reprogramming procedures. It has been shown that protein-based human iPSCs efficiently generated functional dopamine neurons without abnormal properties associated with viral genome integration. Since the efficiency of protein-based reprogramming can be improved by the current subject matter using the delivery platform technology, it widely opens the possibility to generate clinically viable iPS cells. Moreover, this approach enables a finer level of control over cellular function by circumventing the stochastic processes that govern translation and/or transcription in mRNA, plasmid and viral reprogramming. Direct protein delivery thus provides two fundamental advantages over alternative methods by obviating the risk of mutagenic insertion and enabling more accurate control of the highly sensitive reprogramming process. The delivery technology described herein has demonstrated its ability to deliver proteins at high efficiencies to HFs and stem cells. Experiments comparing this technique's delivery capabilities to existing cell penetrating peptide methodologies have shown a significant increase in delivery using this approach (potentially 100× higher based on simulations). Moreover, its physical poration mechanism eliminates the need for chemical modification or the use of exogenous compounds that are involved in alternative protein delivery methods. Small molecules, siRNA and other factors can also be co-delivered during reprogramming as the method is agnostic to the type of material being delivered. This system thus provides a unique tool for inducing cell reprogramming through direct protein delivery. This simple mechanism of action (i.e. diffusion through pores) also enables one to potentially predict and control delivery quantities with high accuracy, thus facilitating optimization studies to improve the understanding of reprogramming dynamics and thereby greatly increasing efficiencies. Finally, one can deploy this microfluidic technique as a medical device to generate iPSCs for clinical tissue engineering and cell therapy applications.

Moreover, the applications of this system are not confined to protein delivery. This technique can include into a universal delivery method capable of delivering a range of macromolecules (DNA, RNA, proteins, sugars, and peptides) to almost any cell type. This enables a host of applications that are underserved by current technologies. Current liposomal, nanoparticle, and electroporation-based methods, for example, often struggle to transfect certain primary cells (such as immune cells or stem cells) and can be ineffective at delivering proteins and nanoparticles (such as quantum dots). Peptide delivery for therapeutic screening and disease mechanism applications can also be addressed by this novel method whereas contemporary practices often require chemical modification or encapsulation. One can also use this method for nanoparticle-based sensing applications to deliver modified quantum dots for organelle labeling and mechanistic disease studies.

Intracellular delivery is a cornerstone of many biological research applications ranging from fundamental studies of gene expression, to disease mechanisms and, as addressed in this application, generation of iPSCs. Established delivery methods, such as liposomes, polymeric nanoparticles and electroporation often involve the use of exogenous compounds as a delivery vehicle (or electric fields in the case of electroporation) and are material and/or cell specific. For example, lipofectamine (Invitrogen) can deliver DNA and RNA molecules (to subsets of cell lines or primary cells) but cannot form the proper complex to deliver proteins or other macromolecules. Electroporation, on the other hand, although promising in its ability to target a variety of cell types, causes damage to the cell due to the high electric fields and has had limited success in protein delivery. This makes it particularly unsuitable for the multiple transfections required in iPSC generation, for example. Membrane penetrating peptides are another delivery technique that is largely specific to proteins. These peptide-based methods, however, have unpredictable effects on protein functionality and suffer from significant protein degradation in the endosome. Hence, the current subject matter describing a universal method capable of delivering a range of macromolecules (DNA, RNA, proteins, peptides, small molecules), with minimal cell death, enables unprecedented control over cellular function in a single technology platform, thereby enabling studies of disease mechanism, identification of macromolecular therapeutic candidates, guided differentiation or reprogramming of stem cells, and the development of diagnostic techniques with reporter cell lines.

The microfluidic device described herein can serve as a broad-based universal delivery platform. As a microfluidic device, it enjoys the benefits of precise control over treatment conditions on a single-cell level. The unique combination of single-cell level control and macro-scale throughput places this device in a unique position relative to existing delivery methods. Data thus far has demonstrated the system's ability to deliver material to over 11 different cell types including cancer cell lines, embryonic stem cells, primary fibroblasts, and primary lymphocytes. Its mechanical poration mechanism has also enabled the delivery of previously challenging materials such as carbon nanotubes and quantum dots.

Previous work using recombinant proteins to produce iPSCs have demonstrated prohibitively low efficiencies (<0.01%) and are thereby unsuitable for wide-spread clinical application. The device, systems, and methods mentioned herein, however, have demonstrated their ability to deliver proteins directly to the cytoplasm with high efficiency and minimal cell death thus providing a compelling opportunity to produce substantial gains in reprogramming efficiency through more effective delivery. By directly determining the quantity of available protein one can exercise accurate control over intracellular kinetics. Other reprogramming methods (e.g., viral, plasmid and mRNA expression), on the other hand, rely on stochastic effects to determine the level of protein availability and are thus unsuitable for kinetic studies. The low efficiency of current reprogramming methodologies indicates that the process is highly sensitive to stochastic variations and only a narrow range of transcription factor expression levels will result in reprogramming. By directly delivering proteins to the cytoplasm, one can exercise unprecedented control over protein availability and thus more consistently impose the exact conditions necessary for reprogramming. These conditions, once identified and optimized, can be reproduced accurately for every cell undergoing treatment and thus dramatically improve reprogramming efficiency.

This technique enables/improves upon a variety of intracellular delivery applications. In addition, the strictly mechanical nature of the technique eliminates any potential complications arising from the use of chemical agents or electric fields. Data has not revealed any substantial changes in cell behavior as a result of the treatment. Thus, this system is a robust, high-throughput, high-efficiency, universal intracellular delivery mechanism with particular utility in reprogramming applications.

Evidence indicates that the rapid deformation that occurs as a cell passes through the constriction induces the formation of transient pores in the cellular membrane enabling diffusion of macromolecules from the surrounding buffer into the cytosol. This technique has been demonstrated in 11 different cell types including cancer cell lines, primary fibroblasts, primary lymphocytes, and embryonic stem cells (without causing differentiation). One prototype is capable of treating ~20,000 cells/s and operating at a range of cell concentrations (104-108 cells/ml). Issues pertaining to clogging have also been largely mitigated by improving experimental protocols and chip design such that each device is capable of treating ~1 million cells prior to clogging, with the option of being cleaned and recycled. In addition, the multi-channel design provides significant redundancy such that the clogging of one channel does not affect the performance of the others. Pressure driven flow (at controlled constant pressure) and the parallel design of the channels ensure a consistent flow profile per channel regardless of the percentage of clogged channels in the chip.

Figure 35:
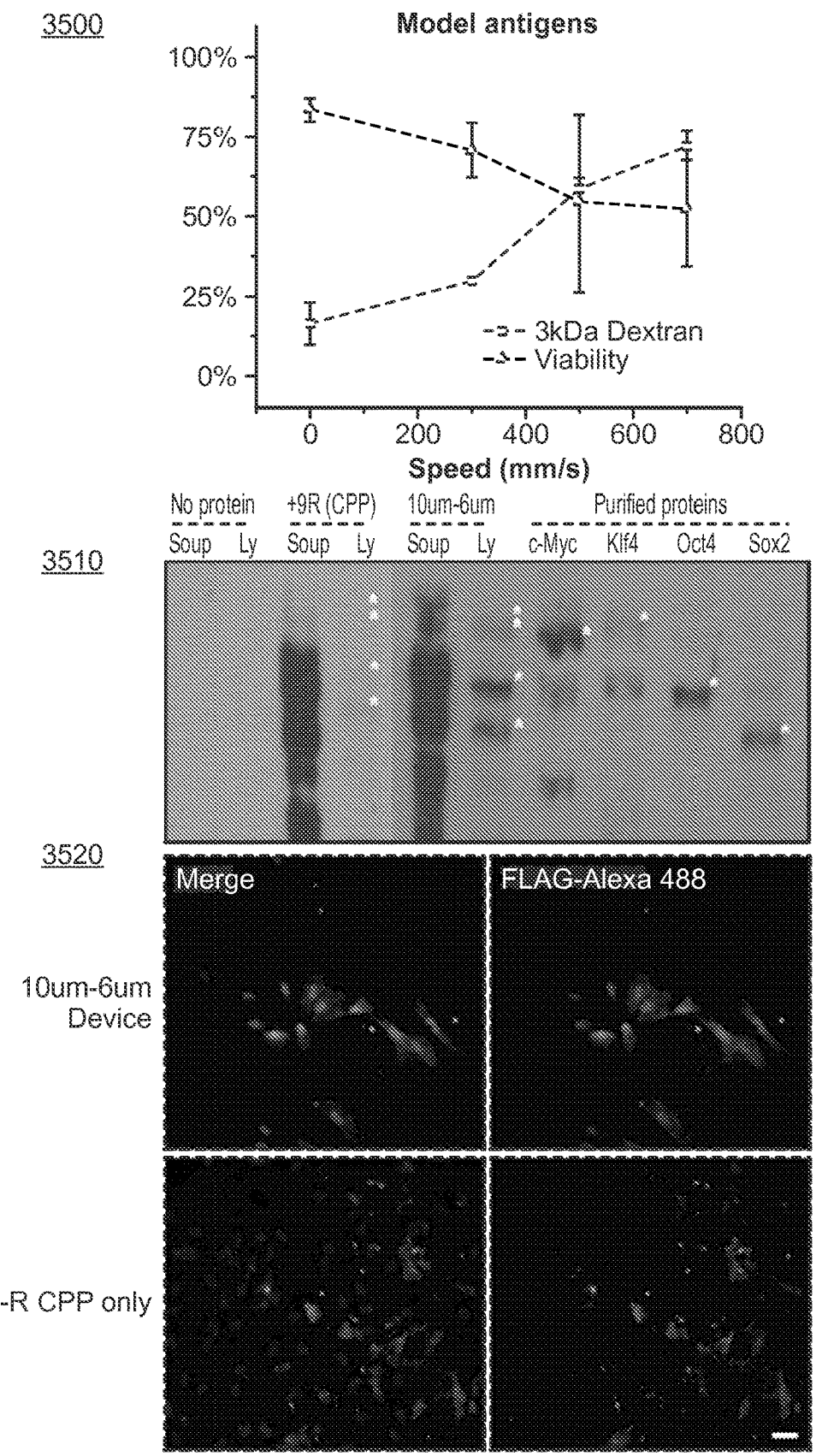
FIG. 35 illustrates delivery efficiency and viability of human embryonic stem cells treated with a 10 µm-6 µm device to deliver payload.

The device's ability to deliver dextran molecules to human fibroblasts and embryonic stem cells has been demonstrated. FIG. 35 illustrates the potential advantages of cell reprogramming. At 3500, the delivery efficiency and viability of human embryonic stem cells treated with a 10 μm-6 μm device to deliver 3 kDa dextran. At 3510, a western blot analysis of c-Myc, Klf-4, Oct-4 and Sox-2 delivery by cell penetrating peptides versus a 10 μm-6 μm device to NuFF cells. The lysate (Ly) columns correspond to the protein content of cells that are washed and lysed while the soup columns correspond to the protein content of the media environment. At 3520 confocal microscopy images of NuFF cells fixed after delivery of the reprogramming factors. The proteins are tagged using an Alexa 488 conjugated anti-FLAG antibody and the nucleus is stained by DAPI.

Moreover, the devices delivery efficiency was compared to that of a 9 arginine (CPP) method currently used for protein-based reprogramming. The results (3510) demonstrated a significant increase in the quantity of c-Myc, Klf4, Oct4 and Sox2 delivered as measured by western blot. Confocal microscopy then confirmed the successful localization of these transcription factors to the cell nucleus (3520). A simple 2-D diffusion model was developed in COMSOL to simulate the delivery mechanism based on literature values for particle diffusivities inside and outside the cell cytoplasm. Fitting this model to the experimental data it can be estimated that the technique delivers 10-40% of the delivery material present in the buffer into the cell cytosol. By comparison, CPP methods for protein delivery are estimated to deliver only 0.1% of the buffer material to the cytosol. This approach thus provides a robust increase in quantity of reprogramming material delivered (10-100 fold). Moreover, it ensures greater bioavailability of the delivered transcription factors.

FIG. 36 depicts generation and characterization of mouse and human iPSC lines by direct delivery of fused reprogramming proteins. At 3600, starting mouse hepatocyte culture (first image); morphology after 6 cycle protein treatments (second image); established iPS colonies (third image); and AP staining of established iPS colonies (fourth image). At 3610 immunostaining of ESC markers (Nanog, Oct4 and SSEA1) in p-miPSC. Nuclei were stained with DAPI (blue). At 3620 bisulfite sequencing analysis of the Oct4 promoter reveals almost complete epigenetic reprogramming in p-miPSC-1 and p-miPSC-2 lines. Open and closed circles indicate unmethylated and methylated CpG, respectively. At 3630, in vivo differentiation potential was analyzed by injecting p-miPSCs into immunodeficiency mice and by H&E staining of teratomas. The resulting teratomas contained tissues representing all three germ layers; ectoderm (neural tube or epidermis), mesoderm (cartilage or muscle), and endoderm (respiratory epithelium or intestinal-like epithelium) lineage cells. At 3640 chimeras derived from p-miPSC-1 (left panel) and p-miPSC-2 (right panel) at E13.5 fetuses show a high level of GFP from injected p-miPSCs. At 3650 to 3670, human iPSC lines, p-hiPSC-01 (3660) and p-hiPSC-02 (3670) are generated by direct delivery of CPP-fused four reprogramming factors from biopsied adult human fibroblasts (3650).

Figure 37:
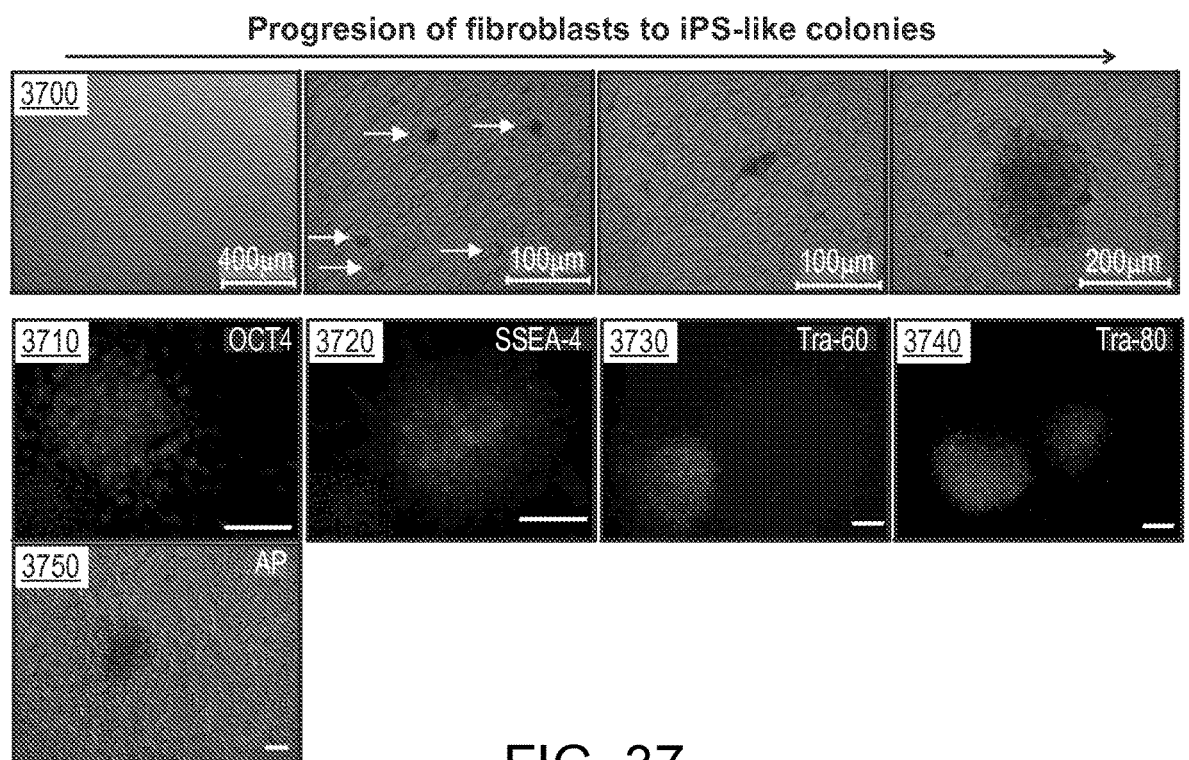
FIG. 37 depicts preliminary protein reprogramming results and depicts expression of the human embryonic stem cell marker Oct4, SSEA-4, Tra-60, Tra-80, Alkaline Phosphatase (AP) in iPSC colonies.

FIG. 37 depicts preliminary protein reprogramming results. At 3700, a progression of morphological changes from fibroblasts into colonies. White arrows indicate potential reprogrammed cells. The red arrow points towards coalescing iPSCs forming a colony. At 3710 to 3760, expression of the human embryonic stem cell marker Oct4, SSEA-4, Tra-60, Tra-80, Alkaline Phosphatase (AP) in iPSC colonies. Were appropriate, the small box represents a DAPI counter stain. Scale bars at 100 µm.

Since protein-based human iPSCs were generated and characterized, further fully reprogrammed mouse and human iPSCs were generated by the previous delivery method of CPP-fused reprogramming factors, as examined by all criteria including epigenetic analyses, in vivo pluripotency, and chimera formation (FIG. 36). However, despite the use of partially purified proteins, the reprogramming efficiency was still low (<0.1%) and took longer than viral reprogramming methods. Thus, it was attempted to use the device to deliver 4 reprogramming proteins Oct4, Sox2, Klf4, and c-Myc to human fibroblasts at a buffer concentration of 80 µg/ml. Cells were treated 4 times with a 48 hr interval between each delivery. Following 14-20 days in culture the first reprogrammed hiPSC-like colonies appeared. During this time, it was observed that the transition in fibroblast morphology as they formed iPSC colonies and they express several hESC markers (FIG. 37).

Clathrin, caveolae and macropinocytosis are the three most commonly proposed mechanisms for endocytotic internalization. To examine whether endocytosis is involved in macromolecular delivery following rapid cell deformation, it is possible to use known chemicals to block these mechanisms. Specifically, chlorpromazine can be used to inhibit clathrin mediated endocytosis; genisten to inhibit caveolae mediated endocytosis; and 5-(N-ethyl-N-isopropyl) amirolide (EIPA,) to inhibit macropinocytosis (all can be purchased from Sigma Aldrich). HeLa cells can be incubated with chlorpromazine (10 µg/ml), genisten (200 µM) and EIPA (25 µM) for 2 hour prior to treatment. Dextran, dsRED and dsRED-9R proteins can then be delivered by rapid deformation of the treated cells. The respective delivery efficiencies, as measured by FACS, can illustrate the influence of endocytosis inhibition on both CPP and device-based delivery mechanisms. Co-localization experiments with endosome markers (Invitrogen) using confocal microscopy can also help determine the percentage of material that is sequestered into endosomes.

It is possible to couple the rapid cell deformation system with other established methods of delivery, such as electroporation, to mitigate endocytotic mechanisms. Incorporating electrodes near the constriction can couple deformation and electroporation to enable delivery effects to yield enhanced system performance relative to either individual method. In addition, co-delivery of chemical agents such as Chloroquine (Sigma), various polymers or endosome escape peptides, can be used to assist endosome escape of delivered materials in the rapid cell deformation system.

As a cell passes through the constriction, it experiences brief (~10-100 us) but rapid shearing and compression. Tangential shearing has been previously shown to induce pore formation. However, the system also induces mechanical compression. To evaluate these parameters, HeLa and HF cells can be incubated in 0.1 µg/ml Lantrunculin A (Invitrogen) for 1 hour prior to delivery to depolymerize the actin cytoskeleton. Fluorescently labeled dextran (Invitrogen) can then be delivered to the treated cell population using the rapid deformation device. These experiments can also be repeated with cells that have been incubated in 10 µM Colchicine (Sigma) for 2 hours prior to delivery to depolymerize the microtubule network. FACS analysis can be used to measure delivery efficiencies of toxin treated cells relative to untreated controls. Pore formation is believed to correlate to the deformation rate of a cell in response to a given geometry. The cytoskeleton's role in resisting deformation was previously investigated using a device that probes cell deformability to provide quantitative measurements of deformation rates. In this method, electrodes are placed on either side of a constriction and the change in capacitance between the two electrodes is measured as a cell passes through. Changes in capacitance across the constriction are then correlated to cell transit time i.e. its deformation rate. The device's delivery performance, in the experiments mentioned above, can be correlated to these prior deformation studies to produce a quantitative relationship between deformation rate and poration efficiency.

Similar to published studies characterizing sonoporation, scanning electron microscopy (SEM) and transmission electron microscopy (TEM) techniques can be employed on samples fixed at defined time intervals after treatment to directly measure the size and distribution of the proposed pores over time. Cell fixation can be done at room temperature using a 25% Gluteraldehyde solution (Sigma). The cell samples can then be dehydrated through successive ethanol washes prior to imaging. Environmental SEM (ESEM) techniques can be used to directly image fixed samples. Due to its relatively low resolution (~200 nm), however, this technique is suitable for detecting 1-0.5 µm scale morphological changes or injuries. Should ESEM fail in detecting any morphological changes, the cells can be coated with a 1-10 nm layer of gold using a vacuum evaporator to enhance resolution down to the nanometer scale necessary to directly observe finer pore structures using SEM. TEM can also be used as an alternative imaging technique should SEM fail to produce the desired results. These techniques enable one to distinguish between a local injury and uniform poration mechanism of delivery and measure the average pore size and distribution. Pore size and distribution in cells that underwent rapid cell deformation can be compared to untreated cells. A localized pore distribution on the membrane surface indicates an injury model while a more uniform distribution supports the uniform poration model.

COMSOL multiphysics software can be used to construct a 3D model of the porated cell. Using published data on cytoplasm and buffer diffusivities, combined with the appropriate pore models from mechanistic studies it is possible to produce a predictive model of delivery. The model emulates a porous membrane separating a low diffusivity cytoplasm from a high diffusivity buffer region. Under the model's assumptions the pores have a fixed size for a fixed amount of time before instantaneous resealing. Dynamic pore behavior, such as changes in shape and diameter, can be incorporated into complex models through coupling with MatLab or other software. Simulated predictions of delivery quantity can be verified using experimental data based on FACS and gel electrophoresis (e.g. western blots). These comparisons can be used to fine-tune the model and hence enable it to predict the quantity of material delivered. This model's predictive capabilities can simulate the effects of varying pore size, pore opening time and buffer concentrations and hence be used as a guide to future studies.

Multi-physics simulations (e.g. COMSOL or CFD-ACE) can also be used to model fluid flow throughout the device. These models can be used to more accurately predict flow speeds and sheer stresses in the inlet, outlet, and constriction regions. This data can be used to elucidate links between sheer stress and flow speed to delivery efficiency across constriction designs. Moreover, by constructing a broad model of the device it is possible to study the consistency of pressure drops between different channels and adjust the inlet and outlet designs to ensure that all channels operate under near-identical conditions so as to improve treatment uniformity across the cell population.

The delivery phenomenon can be optimized primarily for increasing delivery efficiency and cell viability. Population uniformity (i.e. delivering a similar amount of material to each cell) can be used as a secondary optimization parameter. Initial results have identified cell speed, constriction length, constriction width, and entry region shape as sensitive parameters. Media composition, on the other hand, does not appear to be a major factor. It is possible to construct a series of devices, which systematically vary constriction length and width between 5-50 μm and 4-8 μm respectively. Different taper angles as the main channel narrows to form the constriction are possible. The experimental efficiency and viability data from these devices, as measured by FACS, can be correlated to the aforementioned modeling data to better understand the effects of sheer stress and constriction dimensions. This process can be repeated for different cell lines, which may respond differently to the treatment. This data can be used to develop devices with optimized geometries and operating parameters for specific (or specific subsets of) cell types.

Figure 38:
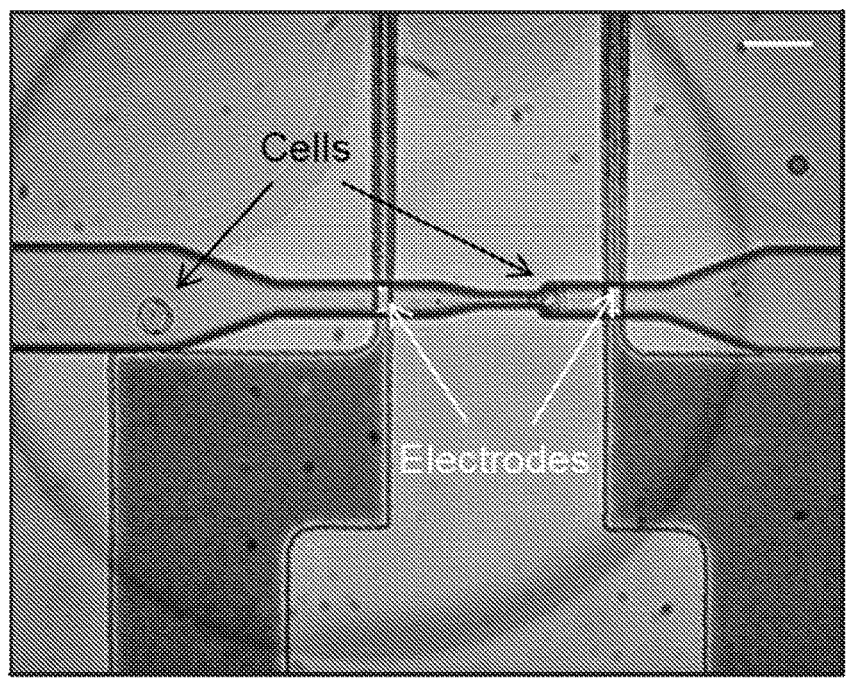
FIG. 38 depicts micrographs illustrating a device modified by incorporated electrodes on either side of the constriction by photolithographic patterning and Au deposition to introduce a localized electrical field into the channel thereby combining cell deformation with electroporation.

FIG. 38 depicts micrographs illustrating alternate device structures. Bright field micrograph of preliminary work combining a constriction and electrodes (scale bar 30 μm). As illustrated in FIG. 38, the device can be modified by coupling the rapid deformation phenomenon with electroporation. Gold electrodes can be incorporated on either side of the constriction by photolithographic patterning and Au deposition to introduce a localized electrical field into the channel. Subsequent experiments can identify operating parameter values (electric field strength, frequency, and operating speed) that demonstrate an improved performance over current methods. By coupling two independent poration mechanisms, one can exercise finer control over the system and manipulate multiple parameters to optimize system performance for each cell type. Additionally, electric fields can be used as a driving force to deliver larger charged molecules, such as DNA, that suffer from low diffusion rates.

A streamlined, disposable version of the system suitable for use by potential collaborators is possible. Injection molding or hot embossing of PMMA and polycarbonate can be used for implementing a polymer-based version of the device. The subsequent reduction in costs would enable these devices to be used as a disposable tool hence improving sterility and ease-of-use. In addition, by simplifying the tubing connections, mounting system and pressure regulator setup, it is feasible to supply a user-friendly system.

Protein-based reprogramming of fibroblasts into iPS cells and optimization studies of the reprogramming parameter space is possible. Previous studies have shown that iPSCs can be generated by direct delivery of CPP-fused reprogramming factors from both human and mouse tissues (FIG. 36) and that these protein-iPSCs can differentiate into functional cells (e.g., dopamine neurons) without abnormal phenotypes associated with viral iPSCs. However, due to many factors including protein degradation in culture, delivery inefficiencies, and degradation inside the cells' endosomes, the reprogramming efficiencies by direct protein delivery are too low (<0.01%) for any practical use. The microfluidic devices described herein can significantly increase the efficiency of protein-based reprogramming by allowing efficient protein delivery directly to the cytoplasm thus avoiding the harsh endosomal environment and the cumbersome endosomal escape process usually encountered in free or encapsulated protein delivery methods.

Generation of human iPSCs is facilitated by microfluidic-based delivery. The device is used to deliver one or more, e.g., 4 reprogramming proteins (c-Myc (protein, Genbank Accession NP_002458.2; DNA, Genbank Accession NM_002467.4), Klf4 (protein, Genbank Accession AAH30811.1; DNA, Genbank Accession NM_004235.4), Oct4 (protein, Genbank Accession ADW77326.1; DNA, Genbank Accession HQ122675.1), and Sox2 (protein, Genbank Accession NP_003097.1; DNA, Genbank Accession NM_003106.3);) to embryonic human fibroblasts (HFs). In addition to Yamanaka four factor (MKOS being c-Myc-Klf4-Oct4-Sox2), several additional factors (e.g., Lin28 (protein, Genbank Accession AAH28566.1; DNA, Genbank Accession NM_024674.4) and Nanog (protein, Genbank Accession AAP49529.1; DNA, Genbank Accession NM_024865.2), Esrrb (protein, Genbank Accession AAI31518.1; DNA, Genbank Accession NM_004452.3), Glis1 (protein, Genbank Accession NP_671726.2; DNA, Genbank Accession NM_147193.2), and PRDM14 (protein, Genbank Accession NP_078780.1; DNA, Genbank Accession NM_024504.3)) have been identified to enhance reprogramming efficiency. It has been fully established that mammalian expression and purification of 6 factors (MKOS+Lin28 and Nanog; MKOSLN) and established the bioactivity of each factor using reporter assays. These factors can be expressed either in E. coli or in mammalian cells. Since E. coli-expressed proteins lack post-translational modifications such as phosphorylation, acetylation and ubiquitination, purified proteins can be used following expression in mammalian cells (HEK293 and CHO). E. coli-expressed proteins (commercially available from Stemgent, Cambridge, Mass.) can be used for comparison. First, FLAG-tagged reprogramming factors expressed in HEK293 cells by transfection can be resuspened in a NP40 cell lysis buffer containing 50 mM Tris-HCl, pH 7.4, 250 mM NaCl, 5 mM EDTA, 1% NP-40, and protease inhibitors. Following centrifugation, collected soluble fraction can be added with equilibrated anti-FLAG M2 agarose affinity gel. After washing with PBS twice, retained FLAG-tagged proteins can be eluted by adding 0.1 mg/ml of FLAG peptide (Sigma). Suspended solution of human fibroblasts and 4 or 6 purified proteins can be applied to the device and treated cells can be plated on to 0.1% gelatin coated plates with conditioned hESC media for 1, 2, or 3 days before the next delivery cycle. After repeating protein delivery cycles (6-16) with the microfluidic device, treated cells will be plated on mitomycin C treated mouse embryonic fibroblast (MEF) and grown for 3-4 weeks with regular hESC media. IPSC colonies can become visible within 3 weeks after seeding on the MEF. The efficiency of iPSC generation can be compared to that by protein delivery using our original CPP-fused recombinant proteins. These iPSC candidates can be thoroughly examined for all criteria of authentic iPSCs, including molecular and cellular properties as well as in vitro and in vivo pluripotency, as previously described. Using 4 or 6 factors will generate iPSC lines with much improved efficiency. It is also possible to further express additional factors such as Esrrb, Glis1, and PRDM14 and use these factors in reprogramming experiments.

Reprogramming proteins and mRNAs and/or microRNAs can be delivered in combination. The microfluidic device can be used to deliver not only proteins but also any other macromolecules. To take advantage of this unique property for optimal non-genome integrating reprogramming, it is possible to combine the use of reprogramming factors and mRNAs and/or microRNAs. In particular, it is of great interest that iPSC lines can be successfully generated by using only microRNAs. Indeed, lipofectamine-based transfection of microRNAs can generate iPSC-like colonies. Since microRNAs likely induce reprogramming in a different mechanism than the reprogramming factors, appropriate combination of both reprogramming proteins and microRNAs via the microfluidic device can further enhance the reprogramming efficiency. The combined delivery of proteins and mRNAs can significantly facilitate the reprogramming efficiencies. Thus, an optimal combined treatment of proteins, mRNAs, and/or microRNAs can be delivered using the microfluidic device. Although microRNA/mRNA may not offer the equivalent level of control as proteins, the device capacity for high-throughput optimization studies still provides significant gains in efficiency relative to previous approaches.

The unique features of the microfluidic device can enable delivery of various quantified amounts of each factor, in a controlled, repeatable manner. Optimization of the current subject matter facilitates the development of a reliable, high efficiency tool for protein delivery to HFs. It is possible to elucidate the optimal delivery quantities and frequencies of each reprogramming factor. Unlike mRNA, plasmid or viral methods, the system does not rely on the stochastic nature of gene expression and/or translation to determine the effective intracellular concentration of transcription factors. Thus, the device's ability to deliver protein directly to the cytosol places it in a unique position to exercise accurate control over the intracellular environment. A series of delivery schedules are possible that vary the treatment frequency (once every 1, 2, or 3 days) and protein concentration of each of the four factors independently. In particular, based on several reports indicating that higher levels of Oct4 is critical for efficient reprogramming, it is possible to test the effect of using different concentrations of Oct4 while keeping other factors' concentrations the same. Different concentrations of c-Myc may be evaluated for a given cell type because it has been found that its high levels generate mostly transformed colonies instead of iPSCs in some situations. Furthermore, it is possible to test the effect of more frequent treatment of c-Myc due to its extremely short half-life (~30 min) with appropriate concentration.

Optimization of temporal treatment of reprogramming factors is facilitated using the described methods. Each factor has a functional role and participates in the reprogramming process. At least one and in some cases, combinations of factors are necessary to achieve the desired reprogramming result. For instance, c-Myc is known to suppress the expression of differentiation genes. In addition, Klf4 is known to repress the microRNA let-7, which is related to differentiation pathways and inhibition of pluripotency. Thus, temporally regulated reprogramming can be possible by treating c-Myc and/or Klf4 for initial period, based on a suboptimal condition. In addition, although Nanog is not required for iPSC generation, it is known to be crucial for final establishment and maintenance of pluripotency. Thus, the effect of adding Nanog at the later stage of reprogramming process can be tested. Furthermore, the sequential treatment of microRNAs and proteins can be tested and compared the reprogramming efficiency to those by each treatment or simultaneous treatment. This temporally regulated reprogramming is feasible due to a unique feature of the microfluidic device and may be important to further optimize the protein reprogramming. Reprogramming efficiency can be calculated by dividing the number of colonies at day 28 by the number of treated HF cells. Once completed, regression analysis can be used to deduce the relative importance of each reprogramming factor, its optimal concentration, optimal delivery frequency/timing and, as a result, the optimal protocol to generate iPSCs. The ability to control the amount and timing of protein delivered into each cell can shed light on the functional significance of each factor in the reprogramming process, thereby further enhancing the understanding of cell reprogramming process and pluripotency establishment. In addition, the results of this work can be used to further improve device design to meet the specific demands of reprogramming and enable the eventual development of clinically applicable versions.

Using the optimized protein reprogramming procedure as described above, the protocol can be generally applied to patient-specific adult human fibroblast cells. Since the efficient differentiation of ESCs and iPSCs into functional dopamine neurons and the effects of transplantation has been studied, it is possible to generate iPSCs or iPSC lines from human fibroblasts derived from Parkinson's patients. Once iPSC lines are generated and characterized, they are induced to differentiate into dopamine neurons and characterize their cellular, molecular, physiological, and electrophysiological properties. The dopamine neurons are tested for in vivo functionality following transplantation into animal models of Parkinson's disease such as the genetic PD model, aphakia mice.

Microfluidic-based protein delivery can be used for direct cell conversion, e.g., the direct conversion of fibroblasts into other cell types such as functional neurons, hepatocytes, and blood cells. In the past, the manipulations used viral expression of key transcription factors, causing significant chromosomal disruptions and gene mutations, thereby highlighting the need to develop non-viral, genome non-integrating conversion methods such as direct protein delivery using the methods described here. Thus, the device can be used for microfluidic-based protein delivery for direct cell conversion. Since mammalian expression of certain transcription factors are sometimes challenging, it may be more feasible to test the conversion by one or two protein factors. However, it is possible to convert fibroblasts to another cell fate using a single factor e.g., Oct4 or Sox2 to generate blood or neural precursors respectively. These proteins are readily available in a purified form, for cell conversions using the microfluidic-based protein delivery.

Figure 44:
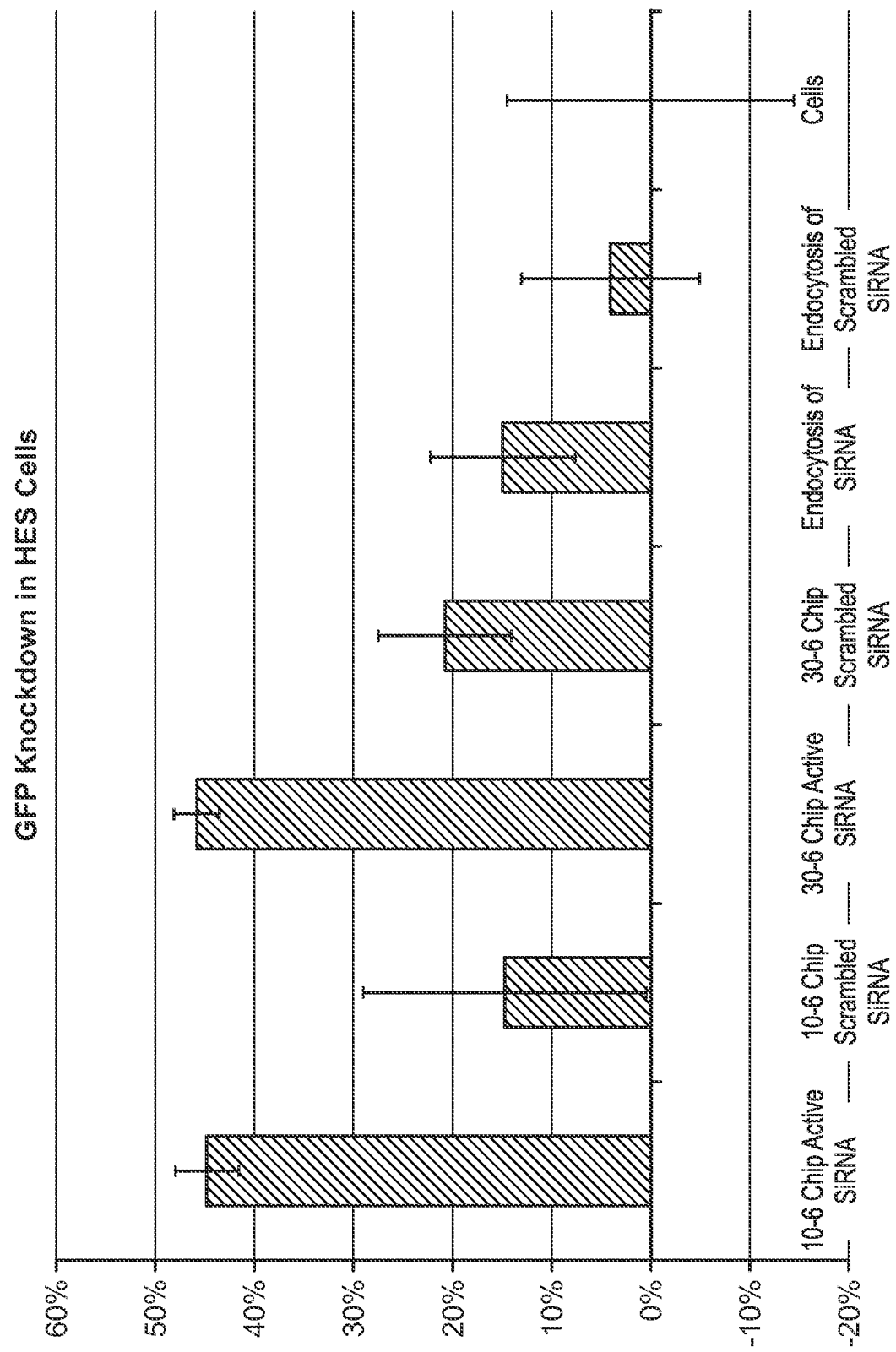
FIG. 44 is a bar graph illustrating GFP knockdown in human embryotic stem cells after treatment using the microfluidic device and related methods.
Figure 45A:
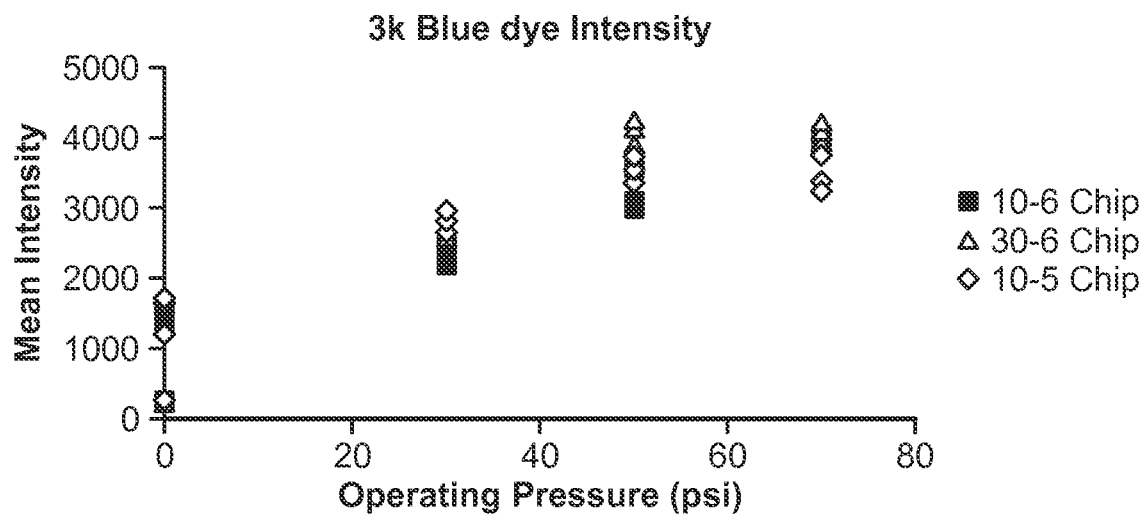
FIGS. 45A and 45B are two plots illustrating the dye intensity and viability of human embryotic stems cells after delivery of a 3 kDa blue dye.
Figure 45B:
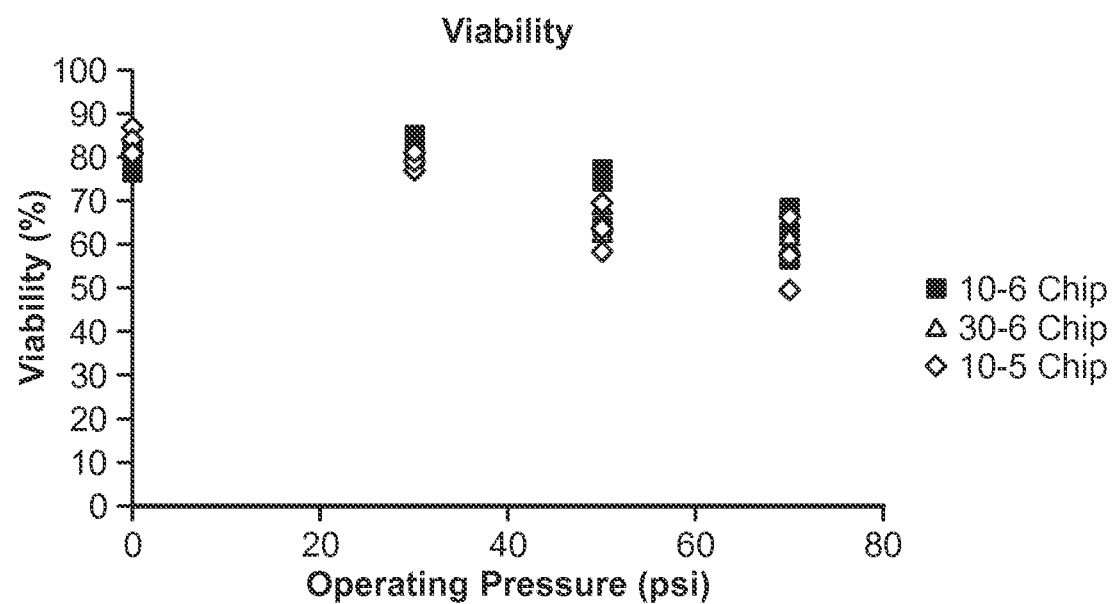

FIG. 44 is a bar graph illustrating GFP knockdown in HESCs as measured by GFP intensity 48 hours after treatment with active siRNA sequences and scrambled controls using the microfluidic device and related methods. FIGS. 45A and 45B are two plots illustrating the dye intensity and viability of human embryotic stems cells after delivery of a 3 kDa blue dye.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

It is noted that one or more references are incorporated herein. To the extent that any of the incorporated material is inconsistent with the present disclosure, the present disclosure shall control. Furthermore, to the extent necessary, material incorporated by reference herein should be disregarded if necessary to preserve the validity of the claims.

Further, while the description above refers to the invention, the description may include more than one invention.

What is claimed is:

1. A method for delivering a payload into a cell, the method comprising:
   providing a cell in a suspension solution;
   passing the solution through a microfluidic channel that includes a cell-deforming constriction, wherein a diameter of the constriction is 20-99% of a diameter of the cell in the suspension solution such that a deforming force is applied to the cell as it passes through the constriction thereby causing perturbations of the cell large enough for a payload to pass through, wherein the cell in solution is passed through the constriction at a speed between 10 mm/s and 10 m/s, and wherein the cell is viable following its passage through the constriction; and
   incubating the cell in a payload-containing solution for a predetermined time after it passes through the constriction.

2. The method of claim 1, wherein a diameter of the constriction is 20 to 60% of the diameter of the cell.

3. The method of claim 1 wherein a cross-section of the microfluidic channel is selected from the group consisting of circular, elliptical, an elongated slit, square, hexagonal, and triangular.

4. The method of claim 1 wherein passing the solution includes passing the solution through an entrance portion, a centerpoint, and an exit portion of the constriction.

5. The method of claim 4 further comprising reducing clogging of the microfluidic channel by adjusting a constriction angle of the entrance portion.

6. The method of claim 4 further comprising improving delivery and cell viability by adjusting the constriction angle of the entrance portion.

7. The method of claim 4, wherein a constriction angle of the entrance portion is 90 degrees.

8. The method of claim 1 wherein passing the solution includes passing the solution through a plurality of microfluidic channels arranged in one of series and/or parallel.

9. The method of claim 1 wherein incubating includes incubating the cell for 0.0001 second to 20 minutes.

10. The method of claim 1 wherein the deformation force comprises compression or compression and shear.

11. A method for delivering a payload into a cell, the method comprising:
    suspending a cell in a solution containing a payload;
    passing the solution through a microfluidic channel that includes a cell-deforming constriction, wherein a diameter of the constriction is 20-99% of a diameter of the cell in the solution such that a deforming force is applied to the cell as it passes through the constriction thereby causing perturbations of the cell, wherein the cell in solution is passed through the constriction at a speed between 10 mm/s and 10 m/s, and wherein the cell is viable following its passage through the constriction; and
    incubating the cell in the solution containing a payload for a predetermined time after it passes through the constriction, wherein the perturbations are large enough for the payload to pass through.

12. The method of claim 11, wherein a diameter of the constriction is 20 to 60% of the diameter of the cell.

13. The method of claim 9 wherein a cross-section of the microfluidic channel is selected from the group consisting of circular, elliptical, an elongated slit, square, hexagonal, and triangular.

14. The method of claim 11 wherein passing the solution includes passing the solution through an entrance portion, a centerpoint, and an exit portion of the constriction.

15. The method of claim 14 further comprising reducing clogging of the microfluidic channel by adjusting a constriction angle of the entrance portion.

16. The method of claim 14 further comprising improving delivery and cell viability by adjusting the constriction angle of the entrance portion.

17. The method of claim 14, wherein a constriction angle of the entrance portion is 90 degrees.

18. The method of claim 11 wherein passing the solution includes passing the solution through a plurality of microfluidic channels arranged in one of series and/or parallel.

19. The method of claim 11 wherein incubating includes incubating the cell for 0.0001 seconds to 20 minutes.

20. The method of claim 11 wherein incubating includes incubating the cell for greater than 0.0001 seconds.

21. The method of claim 11 wherein the deformation force comprises compression or compression and shear.

22. The method as described in claim 1, wherein the method is used to deliver antigen or RNA to immune cells.

23. A method for delivering a payload into a plurality of target cells, the method comprising:
    providing a plurality of target cells in a suspension solution;
    passing the solution containing the plurality of target cells through a plurality of microfluidic channels, each channel including at least one cell-deforming constriction, wherein a diameter of the constriction is 20-99% of a diameter of the cell in the suspension solution such that a deformation of each of the plurality of target cells is induced thereby causing perturbations of the cells large enough for the payload to pass through, wherein the plurality of cells in solution are passed through the constrictions at a speed between 10 mm/s and 10 m/s, and wherein the plurality of target cells are viable following their passage through the constrictions; and
    incubating the plurality of target cells in a payload-containing solution for a predetermined time after it passes through the channels.

24. The method of claim 22, wherein the immune cells are primary immune cells.

25. The method as described in claim 1, wherein the method is used to deliver DNA, RNA, siRNA or protein to primary fibroblasts and stem cells for cell reprogramming.

26. The method as described in claim 1, wherein the method is used to deliver at least one of quantum dots and carbon nanotubes to the cell to aid in imaging the cell.

27. The method as described in claim 1, wherein the method is used to deliver drugs to the cell, and wherein the cell is a tumor cell.

28. The method of claim 1 wherein incubating includes incubating the cell for greater than 0.0001 seconds.

29. The method of claim 1, wherein the suspension solution comprises the cell and the payload before, during, and after passing through the constriction.

30. The method of claim 23, wherein the suspension solution comprises the cell and the payload before, during, and after passing through the constriction.

31. The method of claim 1 wherein deforming the cell includes deforming the cell for 1 µs to 1 ms.

32. The method of claim 3, wherein the cross-section of the microfluidic channel is an elongated slit.

33. The method of claim 8, wherein the plurality of microfluidic channels is arranged in parallel.

34. The method of claim 1, wherein the microfluidic channel comprises a plurality of constrictions.

35. The method of claim 34, wherein the plurality of constrictions is arranged in series and/or parallel.

36. The method of claim 35, wherein the plurality of constrictions is arranged in parallel.

37. The method of claim 11 wherein deforming the cell includes deforming the cell for 1 µs to 1 ms.

38. The method of claim 13, wherein the cross-section of the microfluidic channel is an elongated slit.

39. The method of claim 18, wherein the plurality of microfluidic channels is arranged in parallel.

40. The method of claim 11, wherein the microfluidic channel comprises a plurality of constrictions.

41. The method of claim 40, wherein the plurality of constrictions is arranged in series and/or parallel.

42. The method of claim 40, wherein the plurality of constrictions is arranged in parallel.

43. The method of claim 11, wherein the method is used to deliver antigen or RNA to immune cells.

44. The method of claim 43, wherein the immune cells are primary immune cells.

45. The method of claim 11, wherein the method is used to deliver DNA, RNA, siRNA or protein to primary fibroblasts and stem cells for cell reprogramming.

46. The method of claim 11, wherein the method is used to deliver at least one of quantum dots and carbon nanotubes to the cell to aid in imaging the cell.

47. The method of claim 11, wherein the method is used to deliver drugs to the cell, and wherein the cell is a tumor cell.

48. The method of claim 23, wherein a diameter of the constriction is 20 to 60% of the diameter of the cell.

49. The method of claim 23 wherein a cross-section of the microfluidic channel is selected from the group consisting of circular, elliptical, an elongated slit, square, hexagonal, and triangular.

50. The method of claim 23, wherein the cross-section of the microfluidic channel is an elongated slit.

51. The method of claim 23, wherein passing the solution includes passing the solution through a plurality of microfluidic channels arranged in one of series and/or parallel.

52. The method of claim 23, wherein the plurality of microfluidic channels is arranged in parallel.

53. The method of claim 23, wherein the microfluidic channel comprises a plurality of constrictions.

54. The method of claim 53, wherein the plurality of constrictions is arranged in series and/or parallel.

55. The method of claim 54, wherein the plurality of constrictions is arranged in parallel.

56. The method of claim 23, wherein incubating includes incubating the cell for 0.0001 second to 20 minutes.

57. The method of claim 23, wherein the deformation force comprises compression or compression and shear.

58. The method as described in claim 23, wherein the method is used to deliver antigen or RNA to immune cells.

59. The method of claim 58, wherein the immune cells are primary immune cells.

60. The method of claim 58, wherein the immune cells are primary immune cells.

61. The method of claim 23, wherein the method is used to deliver DNA, RNA, siRNA or protein to primary fibroblasts and stem cells for cell reprogramming.

62. The method of claim 23, wherein the method is used to deliver at least one of quantum dots and carbon nanotubes to the target cell to aid in imaging the target cell.

63. The method of claim 23, wherein the method is used to deliver drugs to the target cell, and wherein the target cell is a tumor cell.

64. The method of claim 1, wherein the suspension solution comprises the cell and the payload after passing through the constriction.

65. The method of claim 23, wherein the suspension solution comprises the cell and the payload after passing through the constriction.

66. The method of claim 1, wherein the suspension solution comprises the cell and the payload during its passage through the constriction.

67. The method of claim 23, wherein the suspension solution comprises the cell and the payload during its passage through the constriction.

* * * * *

UNITED STATES PATENT AND TRADEMARK OFFICE
CERTIFICATE OF CORRECTION

PATENT NO. : 10,696,944 B2  
APPLICATION NO. : 14/352354  
DATED : June 30, 2020  
INVENTOR(S) : Armon R. Sharei et al.

Page 1 of 1

It is certified that error appears in the above-identified patent and that said Letters Patent is hereby corrected as shown below:

On the Title Page

Item (71), please replace:
"(71) Applicants: Massachusetts Institute of Technology, Cambridge, MA (US); Armon R. Sharei, Watertown, MA (US); Andrea Adamo, Cambridge, MA (US); Robert S. Langer, Newton, MA (US); Klavs F. Jensen, Lexington, MA (US)"
With:
--(71) Applicant: Massachusetts Institute of Technology, Cambridge, MA (US)--.

In the Drawings

FIG. 1A: "Cells exposed to delivery material post-construction" should read --Cells exposed to delivery material post-constriction--.

In the Claims

At Column 50, Claim 13, Line 5, "The method of claim 9" should read --The method of claim 11--.

Signed and Sealed this  
Tenth Day of November, 2020

Andrei Iancu  
*Director of the United States Patent and Trademark Office*